(12) United States Patent
Jolidon et al.

(10) Patent No.: US 7,220,744 B2
(45) Date of Patent: May 22, 2007

(54) MONOCYCLIC SUBSTITUTED PHENYL METHANONES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/324,990

(22) Filed: Jan. 3, 2006

(65) Prior Publication Data

US 2006/0167009 A1 Jul. 27, 2006

(30) Foreign Application Priority Data

Jan. 7, 2005 (EP) ................ 051100077

(51) Int. Cl.
*A61K 31/5377* (2006.01)
*A61K 31/496* (2006.01)
*C07D 417/04* (2006.01)
*C07D 417/14* (2006.01)

(52) U.S. Cl. ............... 514/235.8; 514/254.02; 514/254.03; 544/121; 544/367; 544/369

(58) Field of Classification Search ........ 544/367, 544/369, 121
See application file for complete search history.

(56) References Cited

U.S. PATENT DOCUMENTS

| 3,933,802 A | 1/1976 | Ferrini et al. |
| 4,244,871 A | 1/1981 | Kosary et al. |
| 2005/0059668 A1 | 3/2005 | Alberati-Giani et al. |
| 2005/0070539 A1 | 3/2005 | Alberati-Giani et al. |
| 2005/0209241 A1 | 9/2005 | Jolidon et al. |

FOREIGN PATENT DOCUMENTS

| EP | 0 171 636 | 2/1985 |
| EP | 0 624 584 | 11/1994 |
| GB | 867 273 | 5/1961 |
| WO | WO 99/44596 | 9/1999 |
| WO | WO 99/45011 | 9/1999 |
| WO | WO 02/22612 | 3/2002 |
| WO | WO 03/004480 | 1/2003 |
| WO | WO 03/035602 | 5/2003 |
| WO | WO 2004/037800 | 5/2004 |
| WO | WO 2005/014563 A1 | 2/2005 |
| WO | WO 2005/023260 A1 | 3/2005 |
| WO | WO 2005/023261 A1 | 3/2005 |

OTHER PUBLICATIONS

Petigra, R.B., et al., Journal of Medicinal Chemistry, 11(2), pp. 332-336 (1968), XP000590800.
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148 Chemcats No. 2004:3653471 (2004).
Caulfield W. L. et al., Journal of Med. Chem. vol. 44(17) pp. 2679-2682 (2001).
Chem. Abstract XP-002299149 Chemcats No. 2004:2179871 (2004).
Chemical Abstracts Service, Apr. 23, 2003, XP002308402, Database accession No. 2003: 2142911 Chemcats & Catalog: AsInExpress Gold.
Chemical Abstracts Service, Jun. 6, 2003, XP002308481 & Database Chemcats.

(Continued)

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to compounds of formula I

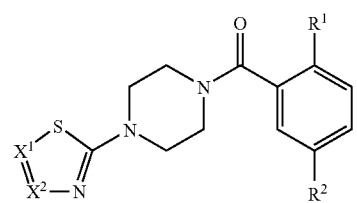

I wherein
$R^1$,
$R^2$, $X^1$, and $X^2$ are as defined in the specification
and to pharmaceutically acceptable acid addition salts thereof. Such compounds are inhibitors of the glycine transporter 1 (GlyT-1) and can be used in the treatment of schizophrenia, cognitive impairment, and Alzheimer's disease.

22 Claims, No Drawings

OTHER PUBLICATIONS

Chemical Abstracts Service, Jan. 1, 2004, XP002308405, Database accession No. 2003:2872406 Chemcats & Catalog: Ambinter Stock Screening Collection.

Chemical Abstracts Service, Jan. 1, 2004, XP002308403, Database accession No. 2004:591813 & Catalog: Ambinter Stock Screening Collection.

Chemical Abstracts Service, Jan. 1, 2004, XP002308404, Database accession No. 2004:660630 & Catalog: Ambinter Screening Library.

Chemical Abstracts Service, XP002308978 Chemcats No. 2002:330684 (2003).

Chemical Abstracts Service, XP002308979, CHEMCATS No. 2003:1026314 (2004).

Chemical Abstracts Service, XP002308980; CHEMCATS No. 2001;2814605 (2003).

Chemical Abstracts Service, XP002308981; CHEMCATS No. 2002:2063001 (2004).

Chemical Abstracts Service, XP002308983; CHEMCATS No. 2003:1026533 (2004).

Chemical Abstracts Service, XP002308984; CHEMCATS No. 2002:2288893 (2004).

Chemical Abstracts Service, XP002308985; CHEMCATS No. 2003:709504 (2004).

Chemical Abstracts Service, XP002308986; CHEMCATS No. 2003:709503 (2004).

Chemical Abstracts Service, XP002308987; CHEMCATS No. 2003:709505 (2004).

Chemical Abstracts Service, XP002308988; CHEMCATS No. 2004:1498769 (2004).

Chemical Abstracts Service, XP002308989; CHEMCATS No. 2002:2386068 (2004).

Chemical Abstracts Service, XP002308990; CHEMCATS No. 2002:2894607 (2004).

Chemical Abstracts Service, XP002308991; CHEMCATS No. 2003:3342164 (2004).

Chemical Abstracts Service, XP002308992; CHEMCATS No. 2003:3345505 (2004).

Chemical Abstracts Service, XP002308993; CHEMCATS No. 2003:3346187 (2004).

Chemical Abstracts Service, XP002309007; CHEMCATS No. 2004:660630.

Abstract corresponding to Document B5—WO 03/035602 (2003).

Cabiddu et al., Journal of Organometallic Chemistry, 1991, 419(1-2) 1-8.

Collins, et al., J. Med. Chem. 1998, 41, p. 5037-5054.

MONOCYCLIC SUBSTITUTED PHENYL METHANONES

PRIORITY DATA

This application claims the benefit of European Application No. 05100077.6, filed Jan. 7, 2005, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325–33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507–518, 2001; Nakazato A and Okuyama S, et al., Exp. Opin. Ther. Patents, 10(1): 75–98, 2000). This pharmacological approach poorly address negative and cognitive symptoms which are the best redictors of functional outcome (Sharma T., Br. J. Psychiatry, 174(suppl. 28): 44–51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., Biol. Psychiatry, 45: 668–679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., Cell, 98: 427–236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N.Y; Bliss T V and Collingridge G L, Nature, 361: 31–39, 1993). Transgenic mice overexpressing the NMDA NR2B subunit exhibit enhanced synaptic plasticity and superior ability in learning and memory (Tang J P et al., Natur, 401–63–69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, Trends in Pharm. Sci., 23(8): 367–373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., Mol. Mem. Biol., 18: 13–20, 2001). Thus, one strategy to enhance NMDA receptor activity is to elevate the glycine concentration in the local microenvironment of synaptic NMDA receptors by inhibition of GlyT-1 transporter (Bergereon R. et al., Proc. Natl. Acad. Sci. USA, 95: 15730–15734, 1998; Chen L. et al., J. Neurophysiol., 89(2): 691–703, 2003).

Glycine transporter inhibitors are suitable for the treatment of neurological and neuropsychiatric disorders. The majority of diseases states implicated are psychoses, schizophrenia (Armer R E and Miller D J, Exp. Opin. Ther. Patents, 11 (4): 563–572, 2001), psychotic mood disorders such as severe major depressive disorder, mood disorders associated with psychotic disorders such as acute mania or depression, associated with bipolar disorders and mood disorders, associated with schizophrenia, (Pralong E T et al., Prog. Neurobiol., 67: 173–202, 2002), autistic disorders (Carlsson M L, J. Neural Trans, 105: 525–535, 1998), cognitive disorders such as dementias, including age related dementia and senile dementia of the Alzheimer type, memory disorders in a mammal, including a human, attention deficit disorders and pain (Armer R E and Miller D J, Exp. Opin. Ther. Patents, 11 (4): 563–572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

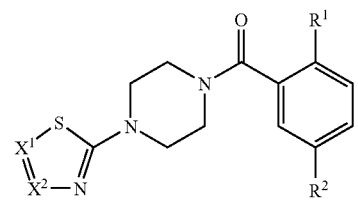

wherein

R$^1$ is —OR$^{1'}$, —SR$^{1'}$, or a heterocycloalkyl group;

R$^{1'}$ is lower alkyl, lower alkyl substituted by halogen, or —(CH$_2$)$_n$-cycloalkyl;

R$^2$ is —S(O)$_2$-lower alkyl, —S(O)$_2$NH-lower alkyl, NO$_2$, or CN;

X$^1$ is CR$^3$ or N;

X$^2$ is CR$^{3'}$ or N;

R$^3$ and R$^{3'}$ are each independently hydrogen, halogen, lower alkyl, CN, NO$_2$, —S(O)$_2$-phenyl, —S(O)$_2$-lower alkyl, —S(O)$_2$-pyridin-2, 3 or 4-yl, phenyl optionally substituted by one or two substituents selected from the group consisting of NO$_2$ and halogen, lower alkyl substituted by halogen, or —C(O)-lower alkyl;

n is 0, 1 or 2;

and pharmaceutically acceptable acid addition salts thereof.

The present invention also provides pharmaceutical compositions containing compounds of the invention and methods for the manufacture of such compounds and compositions.

Compounds of the invention are inhibitors of the glycine transporter 1 (GlyT-1) and have a good selectivity to glycine transporter 2 (GlyT-2) inhibitors. The invention further provides methods for the treatment of diseases related to activation of NMDA receptors via Glyt-1 inhibition. In particular, the invention provides methods for the treatment of neurological and neuropsychiatric disorders, for example, psychoses, dysfunction in memory and learning, schizophrenia, dementia and other diseases in which cognitive processes are impaired, such as attention deficit disorders or Alzheimer's disease. The preferred indications of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-carbon chain containing from 1 to 7 carbon atoms, for example, methyl, ethyl, propyl, isopropyl, n-butyl, i-butyl, 2-butyl, t-butyl and the like. Preferred alkyl groups are those with 1–4 carbon atoms.

As used herein, the term "cycloalkyl" denotes a saturated carbon ring, containing from 3 to 7 carbon atoms, for example cyclopropyl, cyclopentyl or cycloheptyl.

The term "lower alkyl substituted by halogen" denotes a saturated straight- or branched-carbon chain containing from 1 to 7 carbon atoms as defined above, wherein one or more hydrogen atoms are replaced by halogen, for example —CF$_3$, —CH$_2$CF$_3$, —CH$_2$CF$_2$CF$_3$, —CH(CH$_3$)CF$_3$, —C(CH$_3$)$_2$CF$_3$ or —CH(CF$_3$)CH$_2$CH$_3$;

The term "halogen" denotes chlorine, iodine, fluorine and bromine.

The term "heterocycloalkyl" denotes a non aromatic hydrocarbon radical, for example oxetanyl, tetrahydrofuranyl, tetrahydropyranyl, azetidinyl, pyrrolidinyl, piperidinyl, piperazinyl, morpholinyl or thiomorpholinyl. Preferred is morpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of the formula I

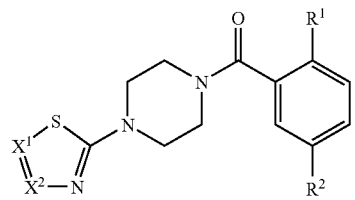

wherein

R$^1$ is —OR$^{1'}$, —SR$^{1'}$, or a heterocycloalkyl group;

R$^{1'}$ is lower alkyl, lower alkyl substituted by halogen, or —(CH$_2$)$_n$-cycloalkyl;

R$^2$ is —S(O)$_2$-lower alkyl, —S(O)$_2$NH-lower alkyl, NO$_2$, or CN;

X$^1$ is CR$^3$ or N;

X$^2$ is CR$^{3'}$ or N;

R$^3$ and R$^{3'}$ are each independently hydrogen, halogen, lower alkyl, CN, NO$_2$, —S(O)$_2$-phenyl, —S(O)$_2$-lower alkyl, —S(O)$_2$-pyridin-2, 3 or 4-yl, phenyl optionally substituted by one or two substituents selected from the group consisting of NO$_2$ and halogen, lower alkyl substituted by halogen, or —C(O)-lower alkyl;

n is 0, 1 or 2;

and pharmaceutically acceptable acid addition salts thereof.

Encompassed by the present invention are compounds of the following structures

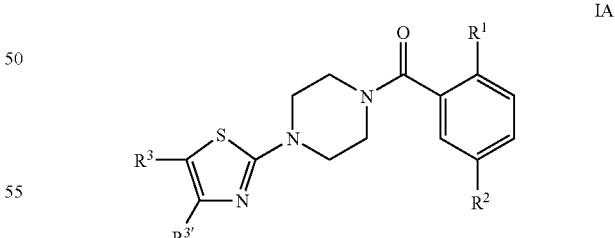

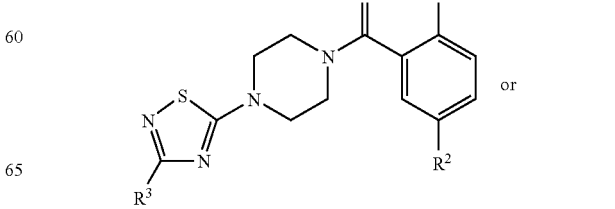

or

-continued

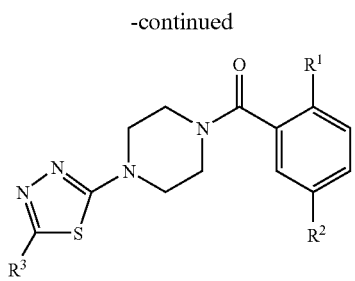

IC wherein the substituents are as described above.

Preferred compounds of the present application are compounds of formula IA.

Further preferred are compounds of formula IA, wherein $R^1$ is $OR^{1'}$.

Especially preferred compounds of formula IA are those, wherein $R^1$ is $OR^{1'}$ and $R^{1'}$ is lower alkyl, for example the following compounds

[4-(5-benzenesulfonyl-thiazol-2-yl)-piperazin-1-yl]-(2-isopropoxy-5-methanesulfonyl-phenyl)-methanone, 2-[4-(2-isobutoxy-5-methanesulfonyl-benzoyl)-piperazin-1-yl]-thiazole-5-carbonitrile, 2-{4-[2-(2,2-dimethyl-propoxy)-5-methanesulfonyl-benzoyl]-piperazin-1-yl}-thiazole-5-carbonitrile,

[4-(5-benzenesulfonyl-thiazol-2-yl)-piperazin-1-yl]-[2-(2,2-dimethyl-propoxy)-5-methanesulfonyl-phenyl]-methanone,

[4-(5-benzenesulfonyl-thiazol-2-yl)-piperazin-1-yl]-(2-isobutoxy-5-methanesulfonyl-phenyl)-methanone, {4-[5-(butane-1-sulfonyl)-thiazol-2-yl]-piperazin-1-yl}-[2-(2,2-dimethyl-propoxy)-5-methanesulfonyl-phenyl]-methanone, (2-((R)-sec-butoxy)-5-methanesulfonyl-phenyl)-[4-(5-trifluoromethyl-thiazol-2-yl)-piperazin-1-yl]-methanone, (2-((S)-sec-butoxy)-5-methanesulfonyl-phenyl)-[4-(5-trifluoromethyl-thiazol-2-yl)-piperazin-1-yl]-methanone and (2-isopropoxy-5-methanesulfonyl-phenyl)-[4-(4-methyl-5-trifluoromethyl-thiazol-2-yl)-piperazin-1-yl]-methanone.

Further preferred compounds of formula IA are those, wherein $R^1$ is $OR^{1'}$ and $R^{1'}$ is lower alkyl substituted by halogen, for example the following compounds:

2-{4-[5-methanesulfonyl-2-(2,2,2-trifluoro-1-methyl-ethoxy)-benzoyl]-piperazin-1-yl}-thiazole-5-carbonitrile, {4-[5-(butane-1-sulfonyl)-thiazol-2-yl]-piperazin-1-yl}-[5-methanesulfonyl-2-(2,2,2-trifluoro-1-methyl-ethoxy)-phenyl]-methanone,

[5-methanesulfonyl-2-(2,2,2-trifluoro-1-methyl-ethoxy)-phenyl]-[4-(5-methyl-4-trifluoromethyl-thiazol-2-yl)-piperazin-1-yl]-methanone,

[5-methanesulfonyl-2-(2,2,2-trifluoro-1-methyl-ethoxy)-phenyl]-[4-(5-trifluoromethyl-thiazol-2-yl)-piperazin-1-yl]-methanone,

[5-methanesulfonyl-2-(2,2,2-trifluoro-1,1-dimethyl-ethoxy)-phenyl]-[4-(5-trifluoromethyl-thiazol-2-yl)-piperazin-1-yl]-methanone,

[5-methanesulfonyl-2-((S)-2,2,2-trifluoro-1-methyl-ethoxy)-phenyl]-[4-(5-trifluoromethyl-thiazol-2-yl)-piperazin-1-yl]-methanone,

[5-methanesulfonyl-2-((R)-2,2,2-trifluoro-1-methyl-ethoxy)-phenyl]-[4-(5-trifluoromethyl-thiazol-2-yl)-piperazin-1-yl]-methanone,

[5-methanesulfonyl-2-(2,2,2-trifluoro-1-methyl-ethoxy)-phenyl]-{4-[5-(2,2,2-trifluoro-ethyl)-thiazol-2-yl]-piperazin-1-yl}-methanone,

[5-methanesulfonyl-2-((S)-2,2,2-trifluoro-1-methyl-ethoxy)-phenyl]-{4-[5-(2,2,2-trifluoro-ethyl)-thiazol-2-yl]-piperazin-1-yl}-methanone,

[5-methanesulfonyl-2-((R)-2,2,2-trifluoro-1-methyl-ethoxy)-phenyl]-{4-[5-(2,2,2-trifluoro-ethyl)-thiazol-2-yl]-piperazin-1-yl}-methanone,

[5-ethanesulfonyl-2-(2,2,2-trifluoro-1-methyl-ethoxy)-phenyl]-[4-(5-trifluoromethyl-thiazol-2-yl)-piperazin-1-yl]-methanone,

[5-methanesulfonyl-2-((S)-2,2,2-trifluoro-1-methyl-ethoxy)-phenyl]-[4-(4-methyl-5-trifluoromethyl-thiazol-2-yl)-piperazin-1-yl]-methanone,

[5-methanesulfonyl-2-((R)-2,2,2-trifluoro-1-methyl-ethoxy)-phenyl]-[4-(4-methyl-5-trifluoromethyl-thiazol-2-yl)-piperazin-1-yl]-methanone and

[5-methanesulfonyl-2-(2,2,3,3,3-pentafluoro-propoxy)-phenyl]-[4-(5-trifluoromethyl-thiazol-2-yl)-piperazin-1-yl]-methanone.

Further preferred compounds of formula IA are those, wherein $R^1$ is $OR^{1'}$ and $R^{1'}$ is —$(CH_2)_n$-cycloalkyl, for example the following compounds:

2-[4-(2-cyclobutylmethoxy-5-methanesulfonyl-benzoyl)-piperazin-1-yl]-thiazole-5-carbonitrile,

[4-(5-benzenesulfonyl-thiazol-2-yl)-piperazin-1-yl]-(2-cyclopentyloxy-5-methanesulfonyl-phenyl)-methanone, {4-[5-(butane-1-sulfonyl)-thiazol-2-yl]-piperazin-1-yl}-(2-cyclopentyloxy-5-methanesulfonyl-phenyl)-methanone, 3-[4-(5-cyano-thiazol-2-yl)-piperazine-1-carbonyl]-4-cyclopentyloxy-N-methyl-benzenesulfonamide and 4-cyclopentyloxy-N-methyl-3-[4-(5-trifluoromethyl-[1,3,4]thiadiazol-2-yl)-piperazine-1-carbonyl]-benzenesulfonamide.

Further preferred compounds of formula IA are those, wherein $R^1$ is $SR^{1'}$, for example the following compound (2-isopropylsulfanyl-5-methanesulfonyl-phenyl)-[4-(5-trifluoromethyl-thiazol-2-yl)-piperazin-1-yl]-methanone.

Preferred compounds of formula IB are those in which $R^1$ is $OR^{1'}$.

A compound of formula IB, wherein $R^1$ is $OR^{1'}$ for $R^{1'}$ being lower alkyl is (2-isopropoxy-5-methanesulfonyl-phenyl)-[4-(3-phenyl-[1,2,4]thiadiazol-5-yl)-piperazin-1-yl]-methanone.

A compound of formula IB, wherein $R^1$ is $OR^{1'}$ for $R^{1'}$ being $(CH_2)_n$-cycloalkyl is 4-cyclopentyloxy-N-methyl-3-[4-(3-phenyl-[1,2,4]thiadiazol-5-yl)-piperazine-1-carbonyl]-benzenesulfonamide.

Compounds of formula IC, wherein $R^1$ is $OR^{1'}$ are, for example the following (2-isopropoxy-5-methanesulfonyl-phenyl)-[4-(5-trifluoromethyl-[1,3,4]thiadiazol-2-yl)-piperazin-1-yl]-methanone, (2-cyclopropylmethoxy-5-methanesulfonyl-phenyl)-[4-(5-trifluoromethyl-[1,3,4]thiadiazol-2-yl)-piperazin-1-yl]-methanone, (2-isobutoxy-5-methanesulfonyl-phenyl)-[4-(5-trifluoromethyl-[1,3,4]thiadiazol-2-yl)-piperazin-1-yl]-methanone, (5-methanesulfonyl-2-morpholin-4-yl-phenyl)-[4-(5-trifluoromethyl-[1,3,4]thiadiazol-2-yl)-piperazin-1-yl]-methanone and

[5-methanesulfonyl-2-((S)-2,2,2-trifluoro-1-methyl-ethoxy)-phenyl]-[4-(5-trifluoromethyl-[1,3,4]thiadiazol-2-yl)-piperazin-1-yl]-methanone.

The present compounds of formula I and their pharmaceutically acceptable salts can be prepared by methods known in the art, for example, by the process described below, which process comprises reacting a compound of formula

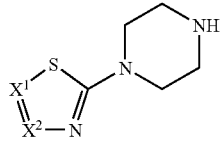

II with a compound of formula

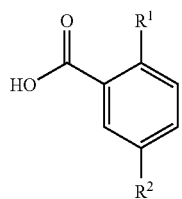

III in the presence of an activating agent, such as TBTU (2-(1H-benzotriazole-1-yl)-1,1,3,3-tetramethyluroniumtetrafluoroborate), to produce a compound of formula

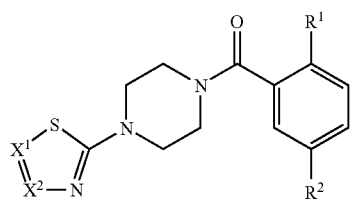

I wherein $X^1$ and $X^2$ and the substituents $R^1$ and $R^2$ are as defined above, and if desired, converting the compounds obtained into pharmaceutically acceptable acid addition salts.

The compounds of formula I can be prepared in accordance with the process variant as described above and with the following schemes 1–7. The starting materials are either commercially available, are otherwise known in the chemical literature, or can be prepared in accordance with methods well known in the art.

Scheme 1

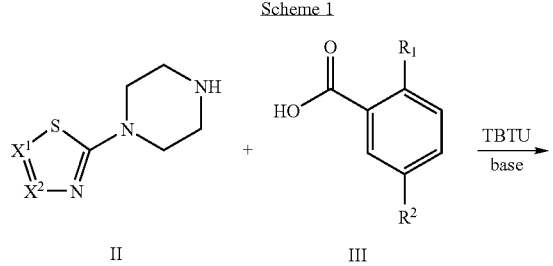

-continued

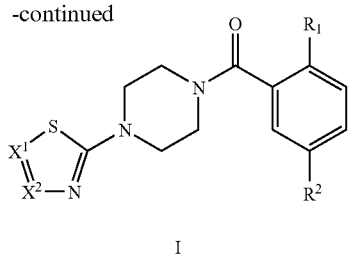

I

Compounds of general formula I can be prepared by reacting piperazine derivatives of formula II with an appropriately substituted acid of formula III in the presence of an activating agent, like TBTU (2-(H-benzotriazole-1-yl)-1,1,3,3-tetramethyluroniumtetrafluoroborate), and a base, such as N-ethyldiisopropylamine (Scheme 1).

The acids of formula III can be prepared by various routes as shown in Schemes 2–5.

Scheme 2

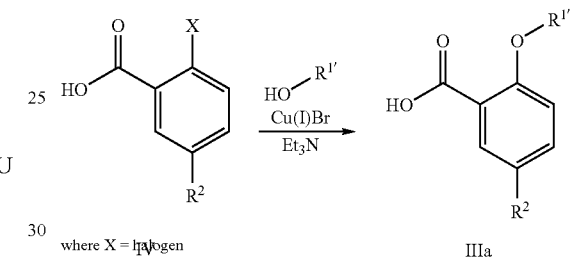

where X = halogen

For example, compounds of formula IIIa where $R^{1'}$ is lower alkyl, lower alkyl substituted by halogen or —(CH$_2$)$_n$-cycloalkyl, can be prepared by reaction of a halogen compound of formula IV with an alcohol of formula $R^{1'}$OH, optionally in the presence of a copper salt, like Cu(I)Br, and a base, such as triethylamine (Scheme 2), at elevated temperature.

Scheme 3

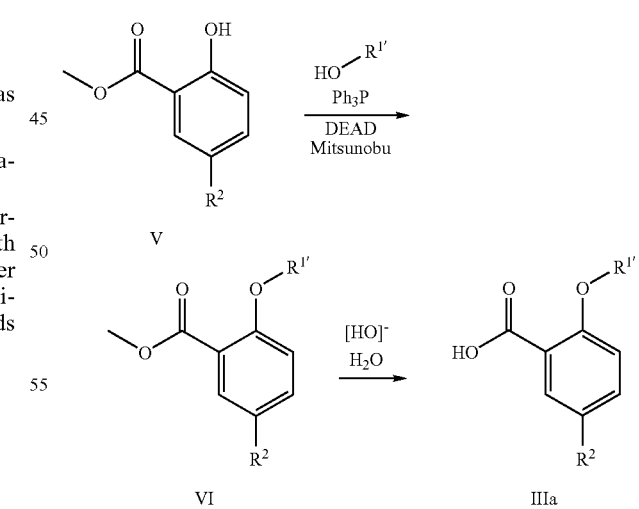

Alternatively, compounds of formula IIIa, where $R^{1'}$ is lower alkyl, lower alkyl substituted by halogen or —(CH$_2$)$_n$-cycloalkyl can be prepared by reacting a hydroxy compound of formula V with an alcohol of formula $R^{1'}$OH, under Mitsunobu reaction conditions in the presence of a phosphine like triphenylphosphine or diphenyl-2-pyridylphosphine, and a dialkylazadicarboxylate like diethylazadicarboxylate or di-tert-butyl azodicarboxylate, to afford intermediate compounds of formula VI, followed by hydrolysis in the presence of an aqueous base such as potassium hydroxide, sodium hydroxide or lithium hydroxide (Scheme 3).

Scheme 4

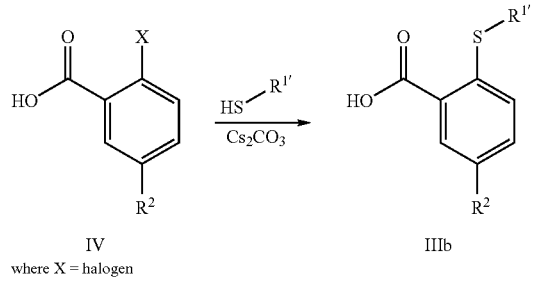

IV
where X = halogen

IIIb

Compounds of formula IIIb where $R^{1'}$ is lower alkyl, lower alkyl substituted by halogen or $-(CH_2)_n$-cycloalkyl can be prepared by reaction of a halogen compound of formula IV with a thiol of formula $R^{1'}SH$, optionally in the presence of a base, such as caesium carbonate, potassium carbonate or sodium carbonate (Scheme 4), at elevated temperature.

Scheme 5

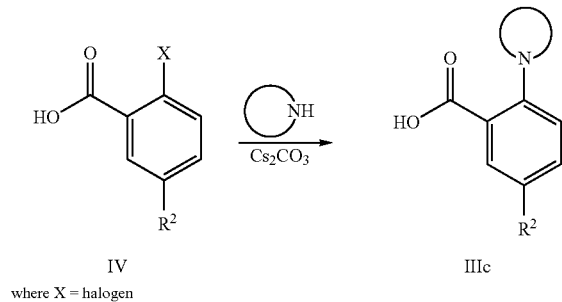

IV
where X = halogen

IIIc

Compounds of formula IIIc where $R^1$ is a heterocycloalkyl group, containing a N atom, can be prepared by reaction of a halogen compound of formula IV with an amine of formula

optionally in the presence of a base, such as caesium carbonate, potassium carbonate or sodium carbonate (Scheme 5), at elevated temperature.

The halogen-substituted and hydroxyl-substituted starting materials of formula IV and V (as shown in Schemes 2–5) are either commercially available, are otherwise known in the chemical literature, or can be prepared using a variety of methods well known in the art.

Scheme 6

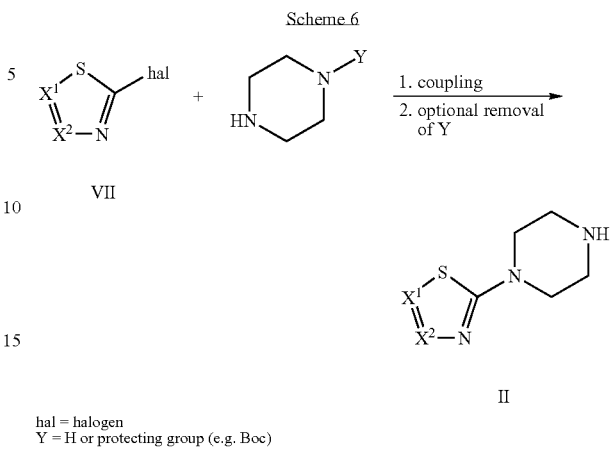

hal = halogen
Y = H or protecting group (e.g. Boc)

Piperazine derivatives of formula II can be prepared by heating of piperazine with the analogous halogen-substituted heterocyclic compound of formula VII, optionally in the presence of an organopalladium catalyst (Scheme 6). Alternatively, piperazine derivatives of formula II can also be prepared by heating of N-protected piperazine with the analogous halogen-substituted heterocyclic compound of formula VII, optionally in the presence of an organopalladium catalyst, followed by cleavage of the protective group (Scheme 6). The protective group is typically tert-butoxycarbonyl (Boc).

The halogen-substituted heterocyclic compounds of formula VII are either commercially available, are otherwise known in the chemical literature, or can be prepared using a variety of methods well known in the art.

Scheme 7

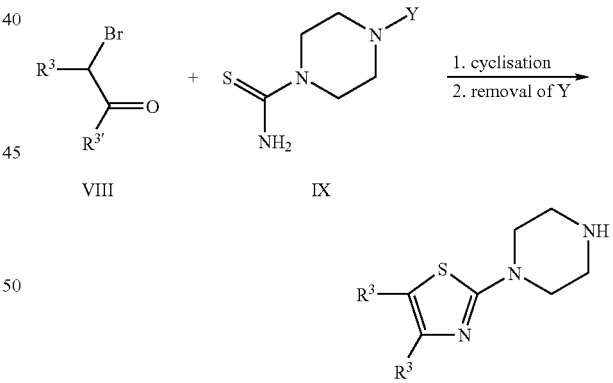

Y = protecting group (e.g. Boc)

In the case where the heterocyclic compound of formula II is a thiazole derivative, the compounds can be prepared by an alternative route as shown in Scheme 7. An appropriately substituted alpha-bromo-ketone compound of formula VIII is condensed with an N-protected piperazine-1-carbothioic acid amide compound of formula IX. The nitrogen protecting group (e.g. Boc) is then removed to afford the thiazole-substituted piperazine compound of formula II.

In the case where compounds of formula II contain reactive functionality (e.g. halogen substituents, hydroxyl substituents, or carbonyl substituents) or masked reactive functionality (e.g. masked carbonyl group or masked hydroxyl group) in $R^3$, further reactions can be performed on either the compounds of formula II or on the compounds of formula I so as to modify the substitiuent $R^3$. Examples of such reactions include functional group interconversions (e.g. change of oxidation state in $R^3$, such as from hydroxy to carbonyl substituent, or from thioether to sulphone substituent), nucleophilic substitution reactions (e.g. in case where there is a reactive halogen substituent in $R^3$), coupling reactions mediated by organometallic catalysts (e.g. Stille or Suzuki coupling reactions, in case where there is a reactive halogen substituent in $R^3$) or coupling reactions mediated by stoichiometric reagents, (e.g. Wittig reaction, in case where there is a reactive carbonyl substituent in $R^3$, or halogen-metal exchange followed by reaction with an electrophile, in case where there is a reactive halogen substituent in $R^3$). Such reactions can be performed using a variety of methods well known in the art and specific examples can be had by reference to the Examples hereunder described.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of formula I

The compounds of formula I can be basic, for example in cases where the residue $R^1$ or $R^3/R^{3'}$ contain a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11–16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (μM) at GlyT-1 in the range of 0.006–0.100. Representative examples are shown in the table below.

| Example No. | $IC_{50}$ (μM) |
|---|---|
| 4 | 0.061 |
| 10 | 0.082 |
| 14 | 0.083 |
| 16 | 0.065 |
| 19 | 0.043 |
| 29 | 0.017 |
| 30 | 0.023 |
| 31 | 0.024 |
| 39 | 0.070 |
| 41 | 0.018 |
| 42 | 0.046 |
| 55 | 0.073 |
| 59 | 0.098 |
| 66 | 0.061 |
| 67 | 0.046 |
| 68 | 0.082 |
| 69 | 0.056 |
| 70 | 0.057 |
| 71 | 0.069 |
| 74 | 0.031 |
| 77 | 0.100 |
| 78 | 0.089 |
| 79 | 0.067 |
| 80 | 0.046 |
| 81 | 0.044 |
| 84 | 0.076 |
| 93 | 0.075 |
| 99 | 0.021 |

-continued

| Example No. | IC$_{50}$ (µM) |
|---|---|
| 100 | 0.055 |
| 101 | 0.026 |
| 103 | 0.006 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salt thereof and, if desired, one or more other therapeutically valuable substances into a galenical administration form together with one or more therapeutically inert carriers. Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope. The following abbreviations were used in the examples:

n-Boc-piperazine: tert-Butyl 1-piperazinecarboxylate,

Oxone®: (potassium peroxymonosulfate) $2KHSO_5.KHSO_4.K_2SO_4$,

TBTU: 2-(1H-benzotriazole-1-yl)-1,1,3,3-tetramethyluroniumtetrafluoroborate;

Synthesis of Intermediates of formula III

EXAMPLE A1

2-Isopropoxy-5-methanesulfonyl-benzoic acid (a) 2-Chloro-5-methanesulfonyl-benzoic acid

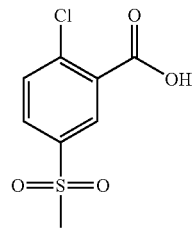

To 99 mmol 2-chloro-5-(methylthio)benzoic acid (purchased from Aldrich) in 400 ml methanol at 0° C. was added 296 mmol Oxone® and the mixture was allowed to stir at RT for 3.5 h. The precipitate was filtered off and the filtrate was concentrated under reduced pressure. The residue was extracted 3 times with 400 ml ethyl acetate and the combined organic phases washed twice with 300 ml 1 N HCl and with 300 ml saturated aqueous NaCl solution and dried with MgSO$_4$. Evaporation under reduced pressure yielded the title compound which was used in the next step without further purification.

(b) 2-Isopropoxy-5-methanesulfonyl-benzoic acid

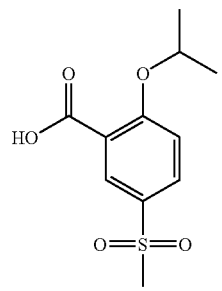

A mixture of 2.13 mmol 2-chloro-5-methanesulfonyl-benzoic acid, 0.64 mmol Cu(I)Br in 5 ml triethylamine and 25 ml isopropanol was heated to 120° C. for 16 h in a sealed tube. The volatiles were removed in vacuo and the residue was taken up in 70 ml 1 N HCl. Extraction with ethyl acetate, drying of the combined organic fractions and evaporation yielded a residue which was purified by reversed phase preparative HPLC eluting with an acetonitrile/water gradient. Evaporation of the product fractions yielded the title compound. MS (m/e): 257.0 ([M–H]$^-$, 100%)

EXAMPLE A2

Rac-5-Methanesulfonyl-2-(2,2,2-trifluoro-1-methyl-ethoxy)-benzoic acid

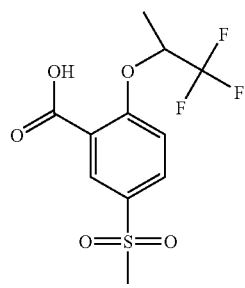

Prepared in analogy to Example A1 (b) from 2-chloro-5-methanesulfonyl-benzoic acid (Example A1(a)) and rac-1,1,1-trifluoro-propan-2-ol. The crude material was purified by preparative HPLC to yield the title compound as a white solid. MS (m/e): 311.3 ([M–H]$^-$, 100%).

EXAMPLE A3

5-Methanesulfonyl-2-(2,2,2-trifluoro-ethoxy)-benzoic acid

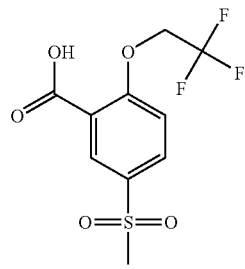

Prepared in analogy to Example A1 (b) from 2-chloro-5-methanesulfonyl-benzoic acid (Example A1(a)) and 2,2,2-trifluoro-ethanol. The crude material was purified by preparative HPLC to yield the title compound as a white solid. MS (m/e): 297.0 ([M–H]$^-$, 100%).

EXAMPLE A4

2-Cyclopentyloxy-5-methanesulfonyl-benzoic acid

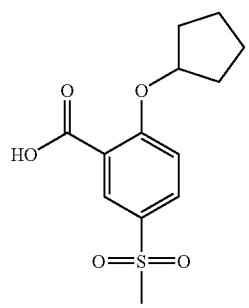

Prepared in analogy to Example A1 (b) from 2-chloro-5-methanesulfonyl-benzoic acid (Example A1(a)) and cyclopentanol. The crude material was purified by flash chromatography to yield the title compound as a yellow solid. MS (m/e): 282.9 ([M–H]$^-$, 100%).

EXAMPLE A5

2-Cyclopropylmethoxy-5-methanesulfonyl-benzoic acid

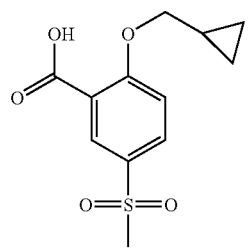

Prepared in analogy to Example A1 (b) from 2-chloro-5-methanesulfonyl-benzoic acid (Example A1(a)) and cyclopropyl-methanol. The crude material was purified by flash chromatography to yield the title compound as a white solid. MS (m/e): 269.1 ([M–H]$^-$, 100%).

EXAMPLE A6

2-Cyclobutylmethoxy-5-methanesulfonyl-benzoic acid (a) 2-Cyclobutylmethoxy-5-methanesulfonyl-benzoic acid methyl ester

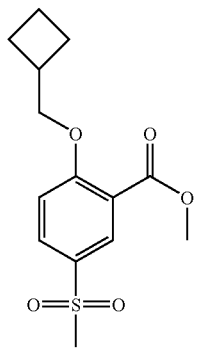

A solution of 6.51 mmol 2-hydroxy-5-methanesulfonyl-benzoic acid methyl ester (WO 2002074774), 9.77 mmol triphenylphosphine, 7.17 mmol cyclobutyl methanol and 7.17 mmol di-tert-butyl azodicarboxylate in 20 ml THF was stirred at 60° C. for 2 hours. The reaction mixture was then concentrated in vacuo and purified by column chromatography ($SiO_2$) to yield the title compound as a light yellow oil.

(b) 2-Cyclobutylmethoxy-5-methanesulfonyl-benzoic acid

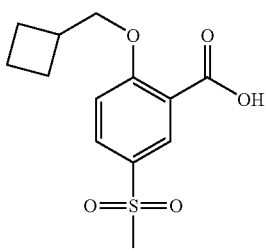

To 6.51 mmol 2-cyclobutylmethoxy-5-methanesulfonyl-benzoic acid methyl ester in 20 ml tetrahydrofuran was added 40 mmol 2 N aq NaOH solution and the reaction mixture was stirred at 60° C. for 2 hours. After such time the reaction mixture was acidified by addition of concentrated HCl and extracted twice with dichloromethane. The combined organic phases were dried over sodium sulfate and concentrated in vacuo. The residue was triturated in ether to give the title compound as a white solid (40% over 2 steps). MS (m/e): 283.3 ([M–H]$^-$, 100%).

EXAMPLE A7

2-Cyclohexyloxy-5-methanesulfonyl-benzoic acid

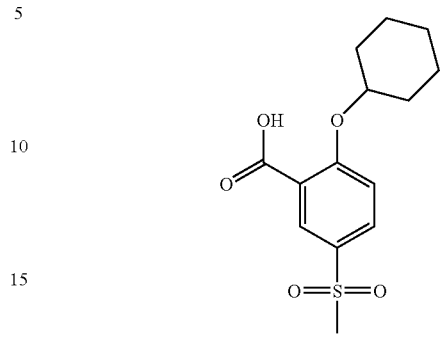

Prepared in analogy to Example A1 (b) from 2-chloro-5-methanesulfonyl-benzoic acid (Example A1(a)) and cyclohexanol. The crude material was purified by preparative HPLC to yield the title compound as a white solid. MS (m/e): 297.3 ([M–H]$^-$, 100%).

EXAMPLE A8

2-Isobutoxy-5-methanesulfonyl-benzoic acid

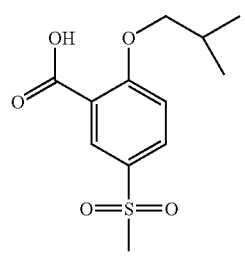

Prepared in analogy to Example A1 (b) from 2-chloro-5-methanesulfonyl-benzoic acid (Example A1(a)) and isobutanol. The crude material was purified by flash chromatography to yield the title compound as a white solid. MS (m/e): 271.1 ([M–H]$^-$, 100%).

EXAMPLE A9

2-Cyclobutoxy-5-methanesulfonyl-benzoic acid

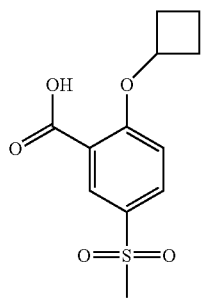

Prepared in analogy to Example A1 (b) from 2-chloro-5-methanesulfonyl-benzoic acid (Example A1(a)) and cyclobutanol. The crude material was purified by preparative HPLC to yield the title compound as a white solid. MS (m/e): 269.3 ([M–H]$^-$, 100%).

EXAMPLE A10

Rac-2-sec-Butoxy-5-methanesulfonyl-benzoic acid

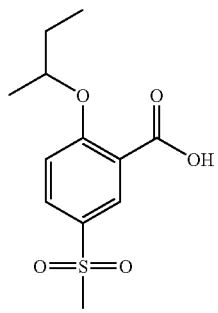

Prepared in analogy to Example A1 (b) from 2-chloro-5-methanesulfonyl-benzoic acid (Example A1(a)) and rac-butan-2-ol. The crude material was purified by preparative HPLC to yield the title compound as a white solid. MS (m/e): 271.4 ([M–H]⁻, 100%).

EXAMPLE A11

2-(2,2-Dimethyl-propoxy)-5-methanesulfonyl-benzoic acid

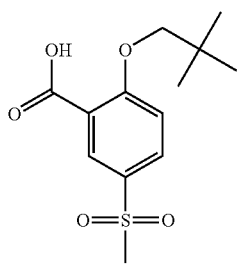

Prepared in analogy to Example A1 (b) from 2-chloro-5-methanesulfonyl-benzoic acid (Example A1(a)) and 2,2-dimethyl-propan-1-ol. The crude material was purified by preparative HPLC to yield the title compound as a white solid. MS (m/e): 285.1 ([M–H]⁻, 100%).

EXAMPLE A12

2-tert-Butoxy-5-methanesulfonyl-benzoic acid (a) 2-tert-Butoxy-5-methanesulfonyl-benzoic acid methyl ester

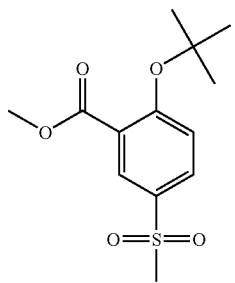

To a solution of 2.17 mmol methyl 5-(methanesulfonyl)-salicylate (WO 2002074774) in 5 ml toluene was added 4.78 mmol N,N-dimethylformamide-di-tert-butylacetal and the reaction mixture was stirred at 80° C. for 1 hour. After such time the reaction mixture was concentrated in vacuo and purified by column chromatography to yield the title compound as colourless oil. MS (m/e): 304.4 (M+NH$_4^+$, 100%).

(b) 2-tert-Butoxy-5-methanesulfonyl-benzoic acid

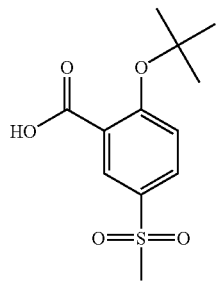

To 5.52 mmol 2-tert-butoxy-5-methanesulfonyl-benzoic acid methyl ester in 25 ml THF was added a solution of 8.34 mmol lithium hydroxide monohydrate in 25 ml water and the reaction mixture was stirred at room temperature for 4 hours. After such time the THF was removed in vacuo and to the remaining aqueous solution was added 8 ml of 1 N aq HCl leading to precipitation of the compound. The precipitate was filtered off and washed several times with water to yield the title compound (67%) as a white solid. MS (m/e): 289.9 (M+NH$_4^+$).

EXAMPLE A13

5-Methanesulfonyl-2-morpholin-4-yl-benzoic acid

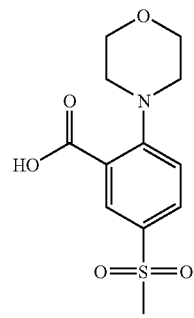

A mixture of 4.26 mmol 2-chloro-5-methanesulfonyl-benzoic acid (Example A1(a)) in 8 ml morpholine was heated at 110° C. for 15 h. After evaporation of all volatiles the residue was acidified by addition of 1 N HCl and extracted three times with ethyl acetate. The combined organic extracts were washed sequentially with 1 N HCl and saturated brine, dried over sodium sulphate, and concentrated in vacuo to afford the title compound as a light yellow amorphous solid (58%). MS (m/e): 284.1 ([M–H]⁻, 100%).

EXAMPLE A14

5-Methanesulfonyl-2-(2,2,2-trifluoro-1,1-dimethyl-ethoxy)-benzoic acid a) 2-Fluoro-5-methylsulfanyl-benzoic acid

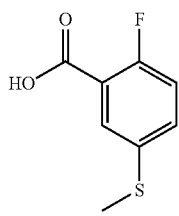

The title compound was prepared by following the procedure described in: Journal of Organometallic Chemistry 1991, 419(1–2), 1–8.

b) 2-Fluoro-5-methanesulfonyl-benzoic acid

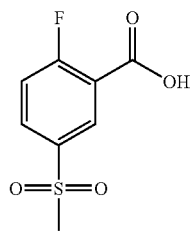

To 2.68 mmol 2-fluoro-5-methanesulfanyl-benzoic acid in 5 ml methanol at 0° C. was added 8.05 mmol Oxone® and the mixture was allowed to stir at RT for 72 h. The precipitate was filtered off and the filtrate was concentrated under reduced pressure. The residue was treated with water and extracted 3 times with 400 ml dichloromethane. The combined organic phases were dried over sodium sulfate. Evaporation under reduced pressure yielded the title compound as a white crystalline solid (yield 79%). MS (m/e): 217.2 (M–H$^+$, 100%).

c) 5-Methanesulfonyl-2-(2,2,2-trifluoro-1,1-dimethyl-ethoxy)-benzoic acid

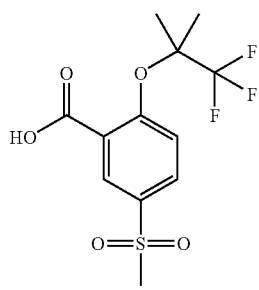

To a solution of 2.75 mmol 2-fluoro-5-methanesulfonyl-benzoic acid in 10 ml N,N-dimethylacetamide were added 14.7 mmol 1,1,1-trifluoro-2-methyl-propan-2-ol and 8.29 mmol cesium carbonate and the mixture was stirred at 170° C. for 72 hours. The reaction mixture was then cooled to room temperature, acidified by addition of formic acid, and then concentrated in vacuo. The residue was purified by preparative HPLC to afford the title compound as a light brown solid (yield 99%). MS (m/e): 325.3. ([M–H]$^-$, 100%)

EXAMPLE A15

5-Methanesulfonyl-2-((S)-2,2,2-trifluoro-1-methylethoxy)-benzoic acid (a) rac-5-Methanesulfonyl-2-(2,2,2-trifluoro-1-methyl-ethoxy)-benzoic acid methyl ester

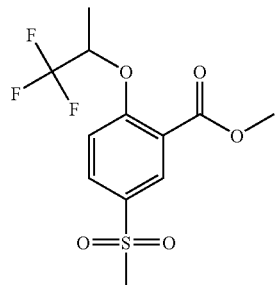

A mixture of 21.7 mmol 2-hydroxy-5-methanesulfonyl-benzoic acid methyl ester (WO 2002074774), 32.5 mmol rac-trifluoro-methanesulfonic acid 2,2,2-trifluoro-1-methyl-ethyl ester [212556-43-9] and 43.4 mmol potassium carbonate in 87 ml DMF was stirred at 80° C. for 48 hours. After cooling to room temperature, the mixture was concentrated in vacuo, resuspended in water and stirred for 1 hour. Filtration yielded the title compound.

(b) 5-Methanesulfonyl-2-((S)-2,2,2-trifluoro-1-methyl-ethoxy)-benzoic acid methyl ester

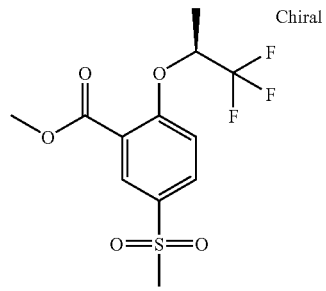

The title compound was obtained by separation of rac-5-methanesulfonyl-2-(2,2,2-trifluoro-1-methyl-ethoxy)-benzoic acid methyl ester by chiral HPLC (Chiralcel OD, 15% ethanol/heptane, flow 35 ml min$^{-1}$, 220 nm, retention time: 86 min.).

(c) 5-Methanesulfonyl-2-((S)-2,2,2-trifluoro-1-methyl-ethoxy)-benzoic acid

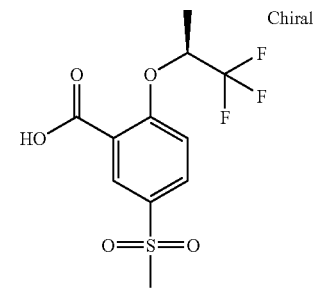

Prepared in analogy to Example A6(b) from 5-methanesulfonyl-2-((S)-2,2,2-trifluoro-1-methyl-ethoxy)-benzoic acid methyl ester. MS (m/e): 311.0 ([M–H]$^-$, 100%)

EXAMPLE A16

5-Methanesulfonyl-2-((R)-2,2,2-trifluoro-1-methyl-ethoxy)-benzoic acid (a) 5-Methanesulfonyl-2-((R)-2,2,2-trifluoro-1-methyl-ethoxy)-benzoic acid methyl ester

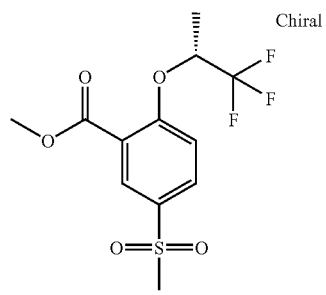

The title compound was obtained by separation of rac-5-methanesulfonyl-2-(2,2,2-trifluoro-1-methyl-ethoxy)-benzoic acid methyl ester (Example A15(a)) by chiral HPLC (Chiralcel OD, 15% ethanol/Heptane, flow 35 ml min$^{-1}$, 220 nm, retention time: 74 min.).

(b) 5-Methanesulfonyl-2-((R)-2,2,2-trifluoro-1-methyl-ethoxy)-benzoic acid

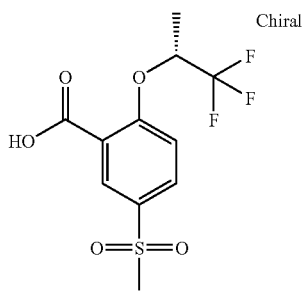

Prepared in analogy to Example A6(b) from 5-methanesulfonyl-2-((R)-2,2,2-trifluoro-1-methyl-ethoxy)-benzoic acid methyl ester. MS (m/e): 311.0 ([M−H]⁻, 100%)

EXAMPLE A17

Rac-5-Ethanesulfonyl-2-(2,2,2-trifluoro-1-methyl-ethoxy)-benzoic acid (a) 5-Ethanesulfonyl-2-fluoro-benzoic acid ethyl ester

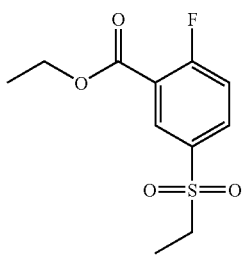

To a solution of 1.98 mol sodium sulfite in 1 l water was added portionwise during 20 min, 0.264 mol 5-chlorosulfonyl-2-fluoro-benzoic acid (CAS: 37098-75-2). The reaction mixture was stirred at room temperature for 2.5 hours then cooled to 0° C. and acidified with 230 ml sulfuric acid (20%) to pH 2. Water was evaporated, and residue was taken up in 200 ml DMF. 73 mmol potassium carbonate and 86 mmol iodoethane were added and the reaction mixture was stirred at room temperature for 50 hours. The solvent was removed in vacuo. The white solid was dissolved in 100 ml water. The aqueous phase was extracted with ethylacetate. The combined extracts were dried over sodium sulfate. Evaporation under reduced pressure and flash chromatography (SiO₂, heptane/ethylacetate1/1) yielded the title compound as a colorless oil (yield 37%). MS (m/e): 261.1 (M+H⁺, 100%).

(b) 5-Ethanesulfonyl-2-fluoro-benzoic acid

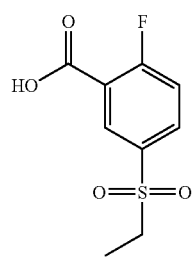

To 10.8 mmol 5-ethanesulfonyl-2-fluoro-benzoic acid ethyl ester in 26 ml tetrahydrofuran was added 26 ml water and 16.1 mmol lithium hydroxide monohydrate and the reaction mixture was stirred at room temperature for 45 minutes. After such time, the reaction mixture was acidified with 1N HCl, tetrahydrofuran was evaporated and the aqueous phase was extracted twice with dichloromethane. The combined organic phases were dried over sodium sulfate and concentrated in vacuo to give the title compound as a white solid (96%). MS (m/e): 232.1 ([M⁺, 100%).

(c) rac-5-Ethanesulfonyl-2-(2,2,2-trifluoro-1-methyl-ethoxy)-benzoic acid

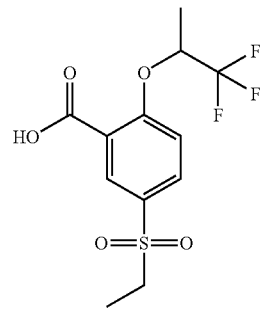

Prepared in analogy to Example A14(c) from 5-ethanesulfonyl-2-fluoro-benzoic acid and rac-1,1,1-trifluoro-propan-2-ol. MS (m/e): 325.1 ([M−H]⁻, 100%)

EXAMPLE A18

5-Ethanesulfonyl-2-isopropoxy-benzoic acid

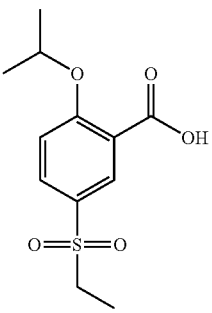

Prepared in analogy to Example A14(c) from 5-ethanesulfonyl-2-fluoro-benzoic acid (Example A17(b)) and isopropanol. MS (m/e): 271.1 ([M−H]⁻, 100%)

EXAMPLE A19

Rac-5-Methanesulfonyl-2-(1-trifluoromethyl-propoxy)-benzoic acid

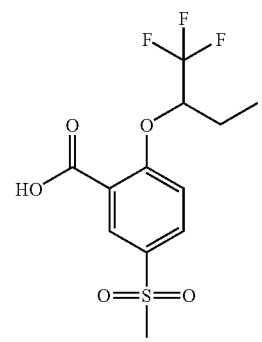

Prepared in analogy to Example A14(c) from 2-fluoro-5-methanesulfonyl-benzoic acid (Example A14(b)) and rac-1,1,1-trifluoro-butan-2-ol. MS (m/e): 325.0 ([M−H]⁻, 100%)

EXAMPLE A20

2-((R)-sec-Butoxy)-5-methanesulfonyl-benzoic acid

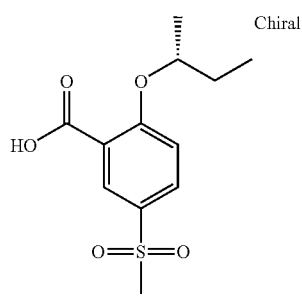

Prepared in analogy to Example A14(c) from 2-fluoro-5-methanesulfonyl-benzoic acid (Example A14(b)) and (R)-butan-2-ol. MS (m/e): 271.1 ([M−H]⁻, 100%)

EXAMPLE A21

2-((S)-sec-Butoxy)-5-methanesulfonyl-benzoic acid

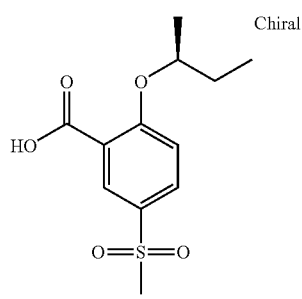

Prepared in analogy to Example A14(c) from 2-fluoro-5-methanesulfonyl-benzoic acid (Example A14(b)) and (S)-butan-2-ol. MS (m/e): 271.1 ([M−H]⁻, 100%)

EXAMPLE A22

2-Isopropylsulfanyl-5-methanesulfonyl-benzoic acid

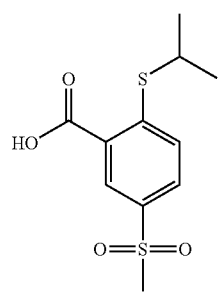

To a solution of 4.58 mmol 2-fluoro-5-methanesulfonyl-benzoic acid (Example A14(b)) in 6 ml N,N-dimethylacetamide were added 15.2 mol cesium carbonate and 10.1 mmol 2-propanethiol and the mixture was stirred at 90° C. for 3 h. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a light yellow liquid which was used in the next step without further purification (yield 99%). EI-MS (m/e): 274.1 (M⁺, 35%), 232.1 ([M−C₃H₆]⁺, 30%, 214.1 (M−C₃H₆−H₂O)⁺, 100%).

EXAMPLE A23

2-Ethylsulfanyl-5-methanesulfonyl-benzoic acid

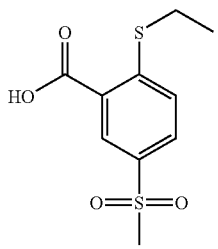

To a solution of 4.58 mmol 2-fluoro-5-methanesulfonyl-benzoic acid (Example A14(b)) in 6 ml N,N-dimethylformamide were added 13.8 mol cesium carbonate and 9.25 mmol ethanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a white solid which was used in the next step without further purification (yield 99%). MS (m/e): 259.0 ([M−H]⁻, 100%).

EXAMPLE A24

5-Methanesulfonyl-2-(2,2,2-trifluoro-ethylsulfanyl)-benzoic acid

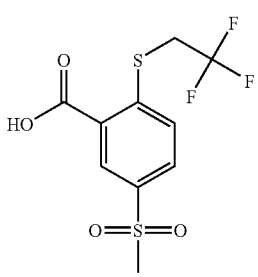

To a solution of 4.58 mmol 2-fluoro-5-methanesulfonyl-benzoic acid (Example A14(b)) in 6 ml N,N-dimethylformamide were added 13.8 mol cesium carbonate and 9.16 mmol 2,2,2-trifluoro-ethanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a red-brown solid which was used in the next step without further purification (yield 99%). MS (m/e): 312.9 ([M−H]⁻, 100%).

EXAMPLE A25

2-Isobutylsulfanyl-5-methanesulfonyl-benzoic acid

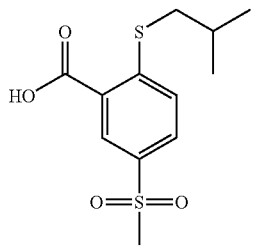

To a solution of 4.58 mmol 2-fluoro-5-methanesulfonyl-benzoic acid (Example A14(b)) in 6 ml N,N-dimethylformamide were added 13.8 mol cesium carbonate and 9.97 mmol 2-methyl-1-propanethiol and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a white solid which was used in the next step without further purification (yield 99%). MS (m/e): 287.0 ([M-H]$^-$, 100%).

EXAMPLE A26

5-Methanesulfonyl-2-methylsulfanyl-benzoic acid

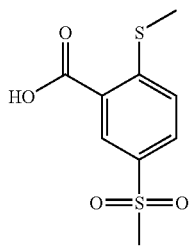

To a solution of 4.58 mmol 2-fluoro-5-methanesulfonyl-benzoic acid (Example A14(b)) in 6 ml N,N-dimethylformamide were added 13.8 mol cesium carbonate and 10.0 mmol sodium methanethiolate and the mixture was stirred at 90° C. for 30 min. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a colourless oil which was used in the next step without further purification (yield 99%). MS (m/e): 244.9 ([M-H]$^-$, 100%).

EXAMPLE A27

2-Morpholin-4-yl-5-nitro-benzoic acid

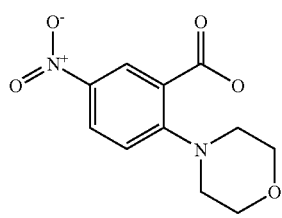

To a solution of 12.2 mmol 2-fluoro-5-nitrobenzoic acid (CAS 7304-32-7; commercially available, e.g. from Fluorochem) in 40 ml THF was added 18.2 mmol morpholine and the mixture was stirred at room temperature for 16 h. The volatiles were removed in vacuo and the residue was resuspended in 25 ml water and acidified to pH 4 by dropwise addition of aqueous HCl. The resulting mixture was stirred at room temperature for 30 min, and the resulting crystals were then collected by filtration and dried in vacuo at 50° C. to afford the title compound as a yellow solid (yield 32%). MS (m/e): 251.0 ([M-H]$^-$, 100%)

EXAMPLE A28

5-Cyano-2-isopropoxy-benzoic acid

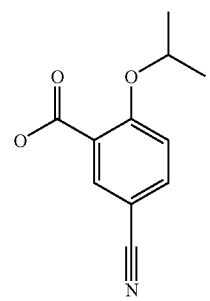

To 198 mmol isopropanol was added 19.8 mmol sodium and the mixture was then heated at 100° C. until all the sodium was dissolved (30 min.). Susbsequently, 6.59 mmol 5-cyano-2-iodobenzoic acid [CAS: 219841-92-6; WO9901455] and 1.32 mmol copper (I) bromide were added and the reaction mixture heated at 120° C. for 2 h. The reaction mixture was then cooled to room temperature and concentrated in vacuo. The residue was suspended in 50 ml 1 M aq HCl and extracted 3× with ethyl acetate. The combined organic extracts were washed with brine, dried over Na$_2$SO$_4$ and concentrated in vacuo. Flash chromatography on silica gel (eluant: heptane/ethyl acetate) provided the title compound as a white solid (yield 55%). MS (m/e): 204.1 ([M-H]$^-$, 100%).

EXAMPLE A29

2-Cyclopentyloxy-5-methylsulfamoyl-benzoic acid (a) 5-Chlorosulfonyl-2-hydroxy-benzoic acid

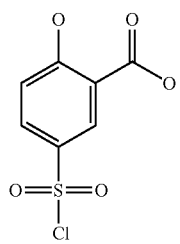

To 3.26 mol chlorosulfonic acid at 0° C. was added 652 mmol salicylic acid in small portions and the mixture was then allowed to stir at RT for 1 h, then at 50° C. for 1 h, and finally at 70° C. for 1 h. The mixture was then added dropwise to 1000 ml ice-water with stirring and stirring continued for an additional 30 min. The ensuing white crystals were collected by filtration, washed three times with water, and then dried in vacuo at 45° C. for 16 h to yield the title compound. MS (m/e): 236.8 ([{$^{37}$Cl}M-H]$^-$, 33%), 235.0 ([{$^{37}$Cl}M-H]$^-$, 100%)

(b) 2-Hydroxy-5-methylsulfamoyl-benzoic acid

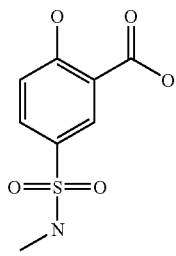

To 63 mmol 5-chlorosulfonyl-2-hydroxy-benzoic acid in 120 ml dichloromethane at RT was added dropwise 317 mmol methylamine (8 M solution in ethanol) and the mixture was allowed to stir at RT for 1 h. The mixture was then concentrated in vacuo. The residue was suspended in 1 M aq NaOH solution and extracted twice with ether. The aqueous phase was acidified with 5 M aq HCl, saturated with NaCl, and extracted 3 times with THF. The combined THF extracts were washed twice with saturated aqueous NaCl solution and dried with $Na_2SO_4$. Evaporation in vacuo yielded the title compound. MS (m/e): 249.0 ($M+NH_4^+$, 100%), 231.9 ($M+H^+$, 63%)

(c) 2-Hydroxy-5-methylsulfamoyl-benzoic acid methyl ester

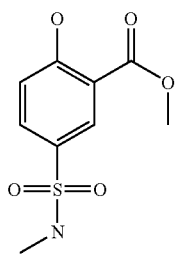

To 77 mmol 2-hydroxy-5-methylsulfamoyl-benzoic acid in 300 ml THF was added 85 mmol CDI and the mixture heated at 70° C. for 1 h. 770 mmol methanol was then added and the mixture was heated at 70° C. for 16 h. The mixture was then cooled to room temperature and concentrated in vacuo. The residue was chromatographed on silica gel (eluant: ethyl acetate/heptane/dichloromethane 45:45:10) to afford the title compound. MS (m/e): 244.1 ([M−H]⁻, 100%)

(d) 2-Cyclopentyloxy-5-methylsulfamoyl-benzoic acid methyl ester

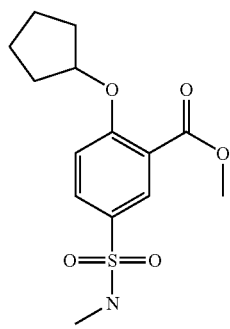

To 2.85 mmol 2-hydroxy-5-methylsulfamoyl-benzoic acid methyl ester, 3.14 mmol cyclopentanol and 3.28 mmol triphenylphosphine in 10 ml THF was added 3.14 mmol di-tert-butyl azodicarboxylate and the mixture was stirred at RT for 2 h. The mixture was then concentrated in vacuo. The residue was chromatographed on silica gel (eluant: ethyl acetate/heptane 2:3) to afford the title compound as a colourless oil. MS (m/e): 312.1 ([M−H]⁻, 100%)

(e) 2-Cyclopentyloxy-5-methylsulfamoyl-benzoic acid

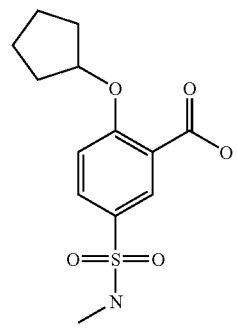

To 2.68 mmol 2-cyclopentyloxy-5-methylsulfamoyl-benzoic acid methyl ester in 10 ml THF was added 20 mmol 2 M aq NaOH and the mixture was stirred at RT for 2 h. The mixture was then extracted twice with ether. The aqueous phase was acidified with 10% aq citric acid and extracted 3 times with ethyl acetate. The combined organic phases were dried with $Na_2SO_4$. Evaporation in vacuo followed by trituration in ether afforded the title compound as a white solid. MS (m/e): 298.3 ([M−H]⁻, 100%)

EXAMPLE A30

5-Methanesulfonyl-2-(2,2,3,3,3-pentafluoro-propoxy)-benzoic acid

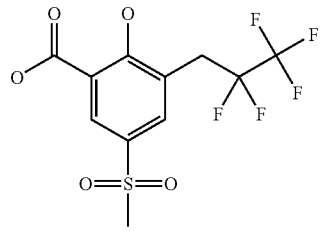

Prepared in analogy to Example A14(c) from 2-fluoro-5-methanesulfonyl-benzoic acid (Example A14(b)) and 2,2,3,3,3-pentafluoro-1-propanol. MS (m/e): 346.9 ([M−H]⁻, 100%)

Synthesis of Compounds of Formula I According to the Invention

EXAMPLE 1

[4-(5-Bromo-thiazol-2-yl)-piperazin-1-yl]-(2-isopropoxy-5-methanesulfonyl-phenyl)-methanone a) 1-(5-Bromo-thiazol-2-yl)-piperazine

A mixture of 2.06 mmol 2,5-dibromothiazole, 6.17 mmol piperazine and 6.17 mmol triethylamine in 6 ml tetrahydrofuran in a sealed tube was heated at 160° C. for 10 min under microwave irradiation. The reaction mixture was concentrated and the residue was purified by chromatography (SiO2, methanol/dichloromethane) to afford the title compound as a white crystalline solid (yield 94%). MS (m/e): 250.0 ({$^{81}$Br}M+H$^+$, 100%), 248.0 ({$^{79}$Br}M+H$^+$, 76%).

b) [4-(5-Bromo-thiazol-2-yl)-piperazin-1-yl]-(2-isopropoxy-5-methanesulfonyl-phenyl)-methanone

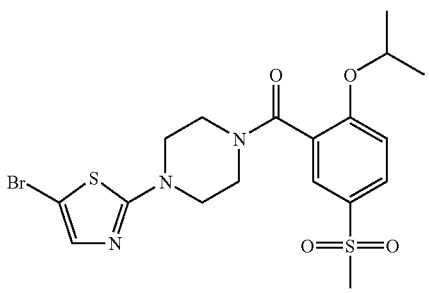

To a solution of 0.31 mmol 2-isopropoxy-5-methanesulfonyl-benzoic acid (Example A1) in 7 ml tetrahydrofuran were added successively 0.46 mmol TBTU, 1.24 mmol N-ethyldiisopropylamine and 0.34 mmol 1-(5-bromo-thiazol-2-yl)-piperazine. The reaction mixture was stirred at RT for 16 h and then concentrated in vacuo. Chromatography (SiO$_2$, ethyl acetate/heptane) afforded the title compound as a white foam (yield 87%). MS (m/e): 490.3 ({$^{81}$Br}M+H$^+$, 100%), 488.3 ({$^{79}$Br}M+H$^+$, 84%).

EXAMPLE 2

(2-Isopropoxy-5-methanesulfonyl-phenyl)-[4-(4-methyl-thiazol-2-yl)-piperazin-1-yl]-methanone a) 2-Iodo-4-methyl-thiazole To a solution of 21.7 mmol diisopropylamine in 50 ml tetrahydrofuran was added dropwise 19.7 mmol butylmagnesium chloride solution (2 M in tetrahydrofuran) and the mixture was stirred at room temperature overnight. 10.1 mmol 4-methylthiazole was then added and stirring continued for 1 hour at room temperature. Finally, a solution of 25.7 mol iodine in 50 ml tetrahydrofuran was added dropwise and stirring continued for a further 1 h. The reaction mixture was then quenched by addition of 20% aqueous sodium thiosulphate solution and the mixture was extracted three times with ethyl acetate. The combined organic phases were dried over sodium sulphate and concentrated in vacuo. Chromatography (SiO$_2$, ether/heptane) afforded the title compound as a brown solid (yield 83%). MS (m/e): 226.1 (M+H$^+$, 100%).

b) 1-(4-Methyl-thiazol-2-yl)-piperazine

A mixture of 1.33 mmol 2-iodo-4-methyl-thiazole, 4.00 mmol piperazine and 4.00 mmol triethylamine in 4 ml tetrahydrofuran in a sealed tube was heated at 160° C. for 2 h under microwave irradiation. The reaction mixture was concentrated and the residue was purified by chromatography (SiO2, methanol/dichloromethane) to afford the title compound as a yellow oil (yield 65%). MS (m/e): 184.3 (M+H$^+$, 100%).

c) (2-Isopropoxy-5-methanesulfonyl-phenyl)-[4-(4-methyl-thiazol-2-yl)-piperazin-1-yl]-methanone

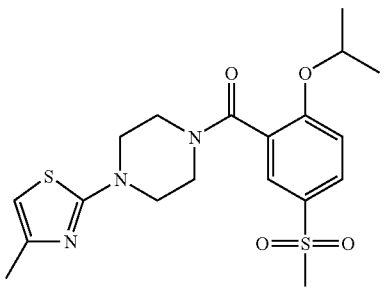

Prepared in analogy to example 1 (b) from 2-isopropoxy-5-methanesulfonyl-benzoic acid (Example A1) and 1-(4-methyl-thiazol-2-yl)-piperazine. The crude material was purified by chromatography (SiO$_2$, ethyl acetate/heptane) to yield the title compound as an amorphous yellow solid (yield 87%). MS (m/e): 424.1 (M+H$^+$, 100%).

EXAMPLE 3

(2-Isopropoxy-5-methanesulfonyl-phenyl)-[4-(5-methyl-thiazol-2-yl)-piperazin-1-yl]-methanone a) 2-Iodo-5-methyl-thiazole Prepared in analogy to example 2 (a) from 5-methylthiazole. The crude material was purified by chromatography (SiO$_2$, ether/heptane) to yield the title compound as a brown oil (yield 69%). MS (m/e): 226.3 (M+H$^+$, 100%).

b) 1-(5-Methyl-thiazol-2-yl)-piperazine

Prepared in analogy to example 2 (b) from 2-iodo-5-methyl-thiazole and piperazine. The crude material was purified by chromatography (SiO$_2$, methanol/dichloromethane) to yield the title compound as a yellow oil (yield 32%). MS (m/e): 184.3 (M+H$^+$, 100%).

c) (2-Isopropoxy-5-methanesulfonyl-phenyl)-[4-(5-methyl-thiazol-2-yl)-piperazin-1-yl]-methanone

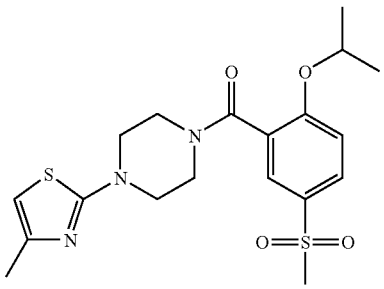

Prepared in analogy to example 1 (b) from 2-isopropoxy-5-methanesulfonyl-benzoic acid (Example A1) and 1-(5-methyl-thiazol-2-yl)-piperazine. The crude material was purified by chromatography (SiO$_2$, ethyl acetate/heptane) to yield the title compound as an off-white foam (yield 75%). MS (m/e): 424.3 (M+H$^+$, 100%).

EXAMPLE 4

[4-(5-Benzenesulfonyl-thiazol-2-yl)-piperazin-1-yl]-(2-isopropoxy-5-methanesulfonyl-phenyl)-methanone a) 4-(5-Bromo-thiazol-2-yl)-piperazine-1-carboxylic acid tert-butyl ester

A mixture of 24.7 mmol 2,5-dibromothiazole, 49.4 mmol tert-butyl 1-piperazinecarboxylate and 74.1 mmol triethylamine in 24 ml tetrahydrofuran in a sealed tube was heated at 160° C. for 30 min under microwave irradiation. The reaction mixture was concentrated and the residue was purified by chromatography (SiO2, ethyl acetate/heptane) to afford the title compound as a white crystalline solid (yield 68%). MS (m/e): 350.2 ($\{^{81}Br\}M+H^+$, 100%), 348.2 ($\{^{79}Br\}M+H^+$, 98%).

b) 4-(5-Phenylsulfanyl-thiazol-2-yl)-piperazine-1-carboxylic acid tert-butyl ester To a solution of 1.44 mmol 4-(5-bromo-thiazol-2-yl)-piperazine-1-carboxylic acid tert-butyl ester in 6 ml tetrahydrofuran at −78° C. was added dropwise 1.44 mmol n-butyllithium solution (1.6 M in hexane) and the mixture was stirred at −78° C. for 10 min. A solution of 1.58 mmol diphenyl disulphide in 1 ml tetrahydrofuran was then added dropwise over 15 min and the reaction mixture was then allowed to warm to room temperature. The reaction mixture was then poured onto saturated brine and the mixture was extracted three times with ethyl acetate/tetrahydrofuran (1:1). The combined organic phases were dried over sodium sulphate and concentrated in vacuo. Chromatography (SiO$_2$, ethyl acetate/heptane) afforded the title compound as a yellow crystalline solid (yield 76%). MS (m/e): 378.3 (M+H$^+$, 100%).

c) 4-(5-Benzenesulfonyl-thiazol-2-yl)-piperazine-1-carboxylic acid tert-butyl ester To a solution of 1.06 mmol 4-(5-phenylsulfanyl-thiazol-2-yl)-piperazine-1-carboxylic acid tert-butyl ester in 10 ml dichloroethane was added 2.65 mmol meta-chloroperbenzoic acid and the mixture was stirred at room temperature for 16 h. The reaction mixture was then diluted with dichloromethane and was washed with saturated aqueous sodium bicarbonate solution and then with water. The organic phase was dried over sodium sulfate and concentrated in vacuo to afford the title compound as a yellow crystalline solid (yield 77%). MS (m/e): 410.3 (M+H+, 100%).

d) 1-(5-Benzenesulfonyl-thiazol-2-yl)-piperazine hydrochloride

To a solution of 0.73 mmol 4-(5-benzenesulfonyl-thiazol-2-yl)-piperazine-1-carboxylic acid tert-butyl ester in 10 ml dioxane was added dropwise 7.32 mmol hydrogen chloride solution (4 M in dioxane) and the mixture was stirred at 80° C. for 2.5 h. The reaction mixture was then cooled to 0° C. and diluted with ether. The resulting crystals were collected by filtration and washed with ether to afford the title compound as a light brown crystalline solid (yield 81%). MS (m/e): 309.9 (M+H+, 100%).

e) [4-(5-Benzenesulfonyl-thiazol-2-yl)-piperazin-1-yl]-(2-isopropoxy-5-methanesulfonyl-phenyl)-methanone

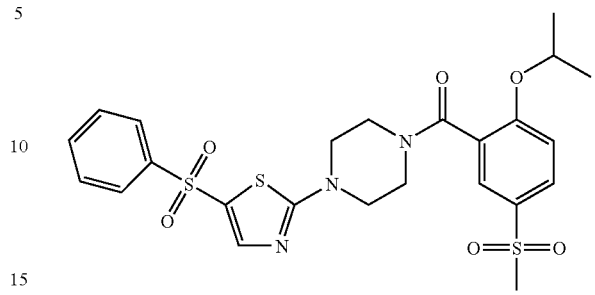

Prepared in analogy to example 1 (b) from 2-isopropoxy-5-methanesulfonyl-benzoic acid (Example A1) and 1-(5-benzenesulfonyl-thiazol-2-yl)-piperazine hydrochloride. The crude material was purified by chromatography (SiO$_2$, methanol/dichloromethane) to yield the title compound as a white crystalline solid (yield 47%). MS (m/e): 550.2 (M+H$^+$, 100%), 567.2 (M+NH$_4^+$, 100%).

EXAMPLE 5

(2-Isopropoxy-5-methanesulfonyl-phenyl)-{4-[4-(2-nitro-phenyl)-thiazol-2-yl]-piperazin-1-yl}-methanone

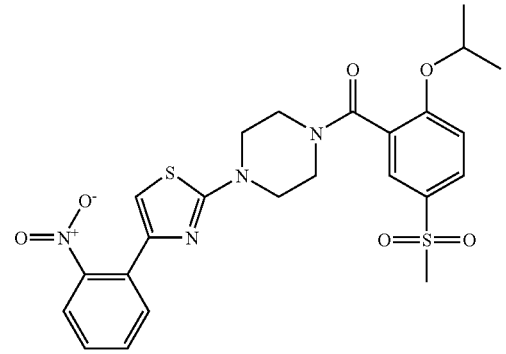

Prepared in analogy to example 1 (b) from 2-isopropoxy-5-methanesulfonyl-benzoic acid (Example A1) and 1-[4-(2-nitro-phenyl)-thiazol-2-yl]-piperazine dihydrochloride. The crude material was purified by chromatography (SiO$_2$, ethyl acetate/heptane) followed by trituration in ether to yield the title compound as a yellow crystalline solid (yield 61%). MS (m/e): 531.3 (M+H$^+$, 100%).

EXAMPLE 6

2-[4-(2-Isopropoxy-5-methanesulfonyl-benzoyl)-piperazin-1-yl]-thiazole-5-carbonitrile a) 2-piperazin-1-yl-thiazole-5-carbonitrile

Prepared in analogy to example 2 (b) from 2-chloro-1,3-thiazole-5-carbonitrile and piperazine. The crude material was purified by chromatography (SiO$_2$, methanol/dichloromethane) to yield the title compound as a white crystalline solid (yield 86%). MS (m/e): 194.9 (M+H$^+$, 100%).

b) 2-[4-(2-Isopropoxy-5-methanesulfonyl-benzoyl)-piperazin-1-yl]-thiazole-5-carbonitrile

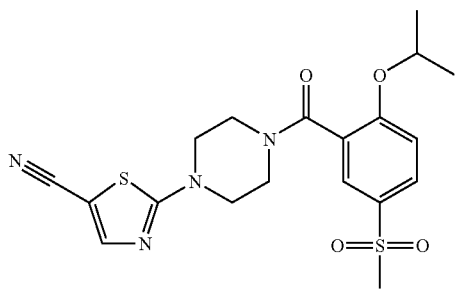

Prepared in analogy to example 1 (b) from 2-isopropoxy-5-methanesulfonyl-benzoic acid (Example A1) and 2-piperazin-1-yl-thiazole-5-carbonitrile. The crude material was purified by chromatography (SiO$_2$, ethyl acetate/heptane) followed by trituration in ether to yield the title compound as a white crystalline solid (yield 69%). MS (m/e): 435.4 (M+H$^+$, 100%).

EXAMPLE 7

{4-[4-(2,4-Dichloro-phenyl)-thiazol-2-yl]-piperazin-1-yl}-(2-isopropoxy-5-methanesulfonyl-phenyl)-methanone

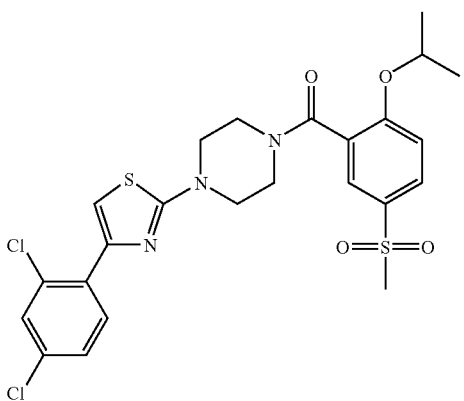

Prepared in analogy to example 1 (b) from 2-isopropoxy-5-methanesulfonyl-benzoic acid (Example A1) and 1-[4-(2,4-dichloro-phenyl)-thiazol-2-yl]-piperazine dihydrochloride. The crude material was purified by chromatography (SiO$_2$, methanol/dichloromethane) (yield 17%). MS (m/e): 558.1 ({$^{37}$Cl}M+H$^+$, 19%), 555.9 ({$^{37}$Cl$^{35}$Cl}M+H$^+$, 58%), 554.1 ({$^{35}$Cl}M+H$^+$, 100%).

EXAMPLE 8

(2-Isopropoxy-5-methanesulfonyl-phenyl)-[4-(5-nitro-thiazol-2-yl)-piperazin-1-yl]-methanone Prepared in analogy to example 2 (b) from 2-bromo-5-nitrothiazole and piperazine. The crude material was purified by chromatography (SiO$_2$, methanol/dichloromethane) to yield the title compound as a light yellow crystalline solid (yield 50%). MS (m/e): 215.3 (M+H$^+$, 100%).

b) (2-Isopropoxy-5-methanesulfonyl-phenyl)-[4-(5-nitro-thiazol-2-yl)-piperazin-1-yl]-methanone

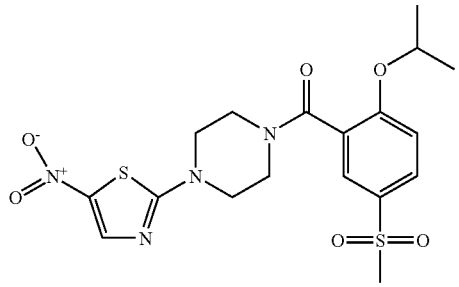

Prepared in analogy to example 1 (b) from 2-isopropoxy-5-methanesulfonyl-benzoic acid (Example A1) and 1-(5-nitro-thiazol-2-yl)-piperazine. The crude material was purified by chromatography (SiO$_2$, ethyl acetate/heptane) followed by trituration in ether to yield the title compound as a yellow crystalline solid (yield 67%). MS (m/e): 455.4 (M+H$^+$, 100%), 472.0 (M+NH$_4^+$, 100%).

EXAMPLE 9

(2-Isopropoxy-5-methanesulfonyl-phenyl)-[4-(3-phenyl-[1,2,4]thiadiazol-5-yl)-piperazin-1-yl]-methanone

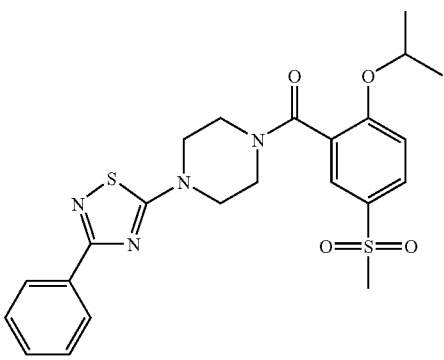

Prepared in analogy to example 1 (b) from 2-isopropoxy-5-methanesulfonyl-benzoic acid (Example A1) and 3-phenyl-5-piperazino-1,2,4-thiadiazole. The crude material was purified by chromatography (SiO$_2$, ethyl acetate/heptane) to yield the title compound as a white crystalline solid (yield 69%). MS (m/e): 487.3 (M+H$^+$, 100%).

EXAMPLE 10

2-{4-[5-Methanesulfonyl-2-(2,2,2-trifluoro-1-methyl-ethoxy)-benzoyl]-piperazin-1-yl}-thiazole-5-carbonitrile

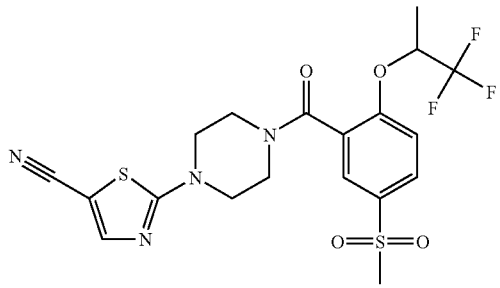

Prepared in analogy to example 1 (b) from 5-methanesulfonyl-2-(2,2,2-trifluoro-1-methyl-ethoxy)-benzoic acid (Example A2) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 59%). MS (m/e): 489.1 (M+H$^+$, 100%), 506.1 (M+NH$_4^+$, 78%).

EXAMPLE 11

2-{4-[5-Methanesulfonyl-2-(2,2,2-trifluoro-ethoxy)-benzoyl]-piperazin-1-yl}-thiazole-5-carbonitrile

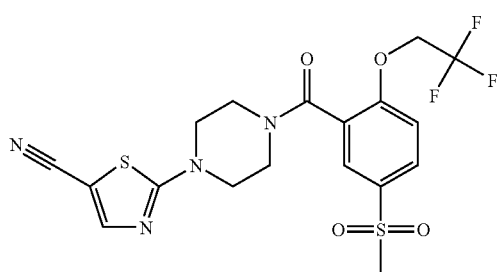

Prepared in analogy to example 1 (b) from 5-methanesulfonyl-2-(2,2,2-trifluoro-ethoxy)-benzoic acid (Example A3) and 2-piperazin-1-yl-thiazole-5-carbonitrile (Example 6(a)). The crude material was purified by chromatography (SiO$_2$, ethyl acetate/heptane) followed by trituration in ether to yield the title compound as a light brown crystalline solid (yield 57%). MS (m/e): 475.0 (M+H$^+$, 100%), 492.3 (M+NH$_4^+$, 90%).

EXAMPLE 12

2-[4-(2-Cyclopentyloxy-5-methanesulfonyl-benzoyl)-piperazin-1-yl]-thiazole-5-carbonitrile

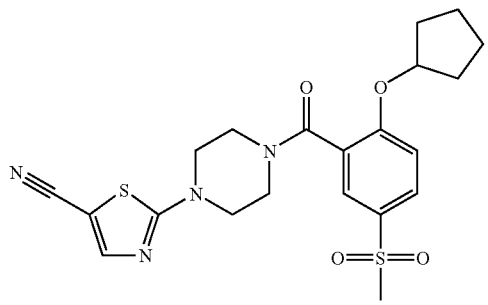

Prepared in analogy to example 1 (b) from 2-cyclopentyloxy-5-methanesulfonyl-benzoic acid (Example A4) and 2-piperazin-1-yl-thiazole-5-carbonitrile (Example 6(a)). The crude material was purified by chromatography (SiO$_2$, ethyl acetate/heptane) followed by trituration in ether to yield the title compound as an off-white crystalline solid (yield 64%). MS (m/e): 461.3 (M+H$^+$, 100%).

EXAMPLE 13

2-[4-(2-Cyclopropylmethoxy-5-methanesulfonyl-benzoyl)-piperazin-1-yl]-thiazole-5-carbonitrile

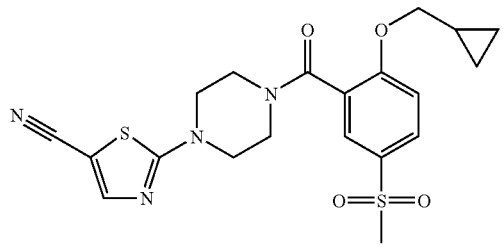

Prepared in analogy to example 1 (b) from 2-cyclopropylmethoxy-5-methanesulfonyl-benzoic acid (Example A5) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 75%). MS (m/e): 447.3 (M+H$^+$, 100%).

EXAMPLE 14

2-[4-(2-Cyclobutylmethoxy-5-methanesulfonyl-benzoyl)-piperazin-1-yl]-thiazole-5-carbonitrile

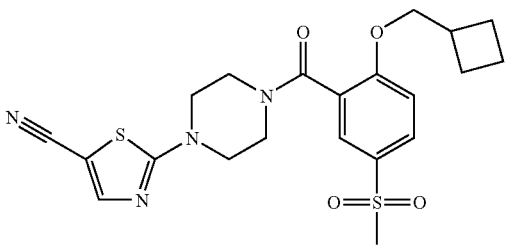

Prepared in analogy to example 1 (b) from 2-cyclobutylmethoxy-5-methanesulfonyl-benzoic acid (Example A6) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 61%). MS (m/e): 461.3 (M+H$^+$, 100%).

EXAMPLE 15

2-[4-(2-Cyclohexyloxy-5-methanesulfonyl-benzoyl)-piperazin-1-yl]-thiazole-5-carbonitrile

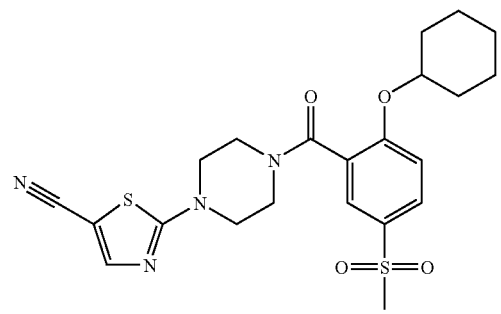

Prepared in analogy to example 1 (b) from 2-cyclohexyloxy-5-methanesulfonyl-benzoic acid (Example A7) and

EXAMPLE 16

2-[4-(2-Isobutoxy-5-methanesulfonyl-benzoyl)-piperazin-1-yl]-thiazole-5-carbonitrile

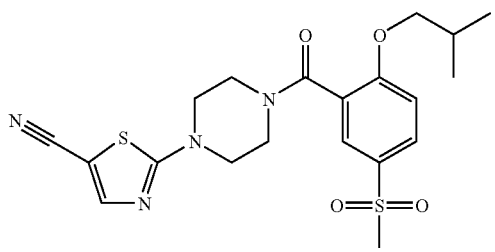

Prepared in analogy to example 1 (b) from 2-isobutoxy-5-methanesulfonyl-benzoic acid (Example A8) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 61%). MS (m/e): 449.4 (M+H$^+$, 100%).

EXAMPLE 17

2-[4-(2-Cyclobutoxy-5-methanesulfonyl-benzoyl)-piperazin-1-yl]-thiazole-5-carbonitrile

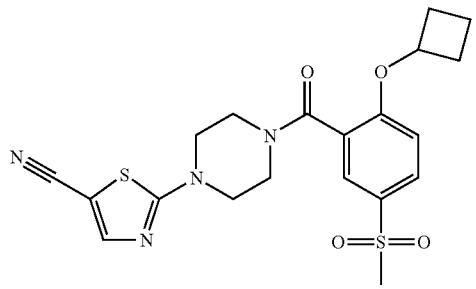

Prepared in analogy to example 1 (b) from 2-cyclobutoxy-5-methanesulfonyl-benzoic acid (Example A9) and 2-piperazin-1-yl-thiazole-5-carbonitrile (Example 6(a)). The crude material was purified by chromatography (SiO$_2$, ethyl acetate/heptane) followed by trituration in ether to yield the title compound as an off-white crystalline solid (yield 54%). MS (m/e): 447.2 (M+H$^+$, 100%).

EXAMPLE 18

2-[4-(2-sec-Butoxy-5-methanesulfonyl-benzoyl)-piperazin-1-yl]-thiazole-5-carbonitrile

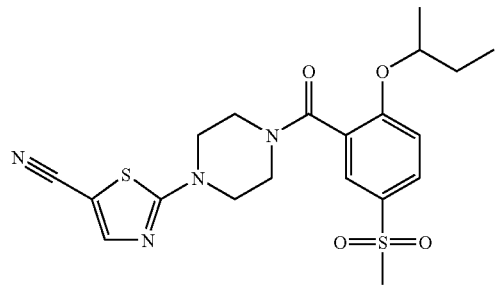

Prepared in analogy to example 1 (b) from 2-sec-butoxy-5-methanesulfonyl-benzoic acid (Example A10) and 2-piperazin-1-yl-thiazole-5-carbonitrile (Example 6(a)). The crude material was purified by chromatography (SiO$_2$, ethyl acetate/heptane) followed by trituration in ether to yield the tide compound as a white crystalline solid (yield 34%). MS (m/e): 449.4 (M+H$^+$, 100%).

EXAMPLE 19

2-{4-[2-(2,2-Dimethyl-propoxy)-5-methanesulfonyl-benzoyl]-piperazin-1-yl}-thiazole-5-carbonitrile

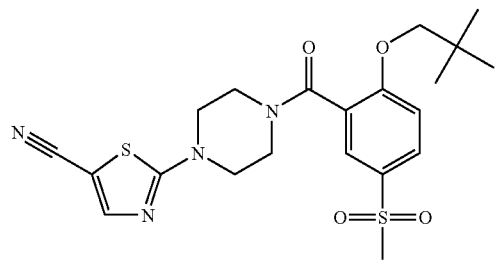

Prepared in analogy to example 1 (b) from 2-(2,2-dimethyl-propoxy)-5-methanesulfonyl-benzoic acid (Example A11) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 68%). MS (m/e): 463.3 (M+H$^+$, 100%).

EXAMPLE 20

2-[4-(2-tert-Butoxy-5-methanesulfonyl-benzoyl)-piperazin-1-yl]-thiazole-5-carbonitrile

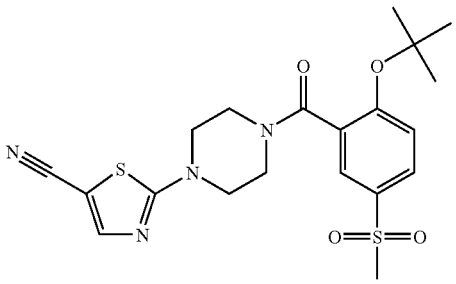

Prepared in analogy to example 1 (b) from 2-tert-butoxy-5-methanesulfonyl-benzoic acid (Example A12) and 2-piperazin-1-yl-thiazole-5-carbonitrile (Example 6(a)). The crude material was purified by chromatography (SiO$_2$, ethyl acetate/heptane) followed by trituration in ether to yield the title compound as a white crystalline solid (yield 52%). MS (m/e): 449.3 (M+H$^+$, 50%), 466.4 (M+NH$_4^+$, 100%).

EXAMPLE 21

(2-Isopropoxy-5-methanesulfonyl-phenyl)-[4-(5-methanesulfonyl-thiazol-2-yl)-piperazin-1-yl]-methanone a) 4-(5-Methylsulfanyl-thiazol-2-yl)-piperazine-1-carboxylic acid tert-butyl ester Prepared in analogy to example 4 (b) from 4-(5-bromothiazol-2-yl)-piperazine-1-carboxylic acid tert-butyl ester (Example 4(a)) and dimethyl disulphide. The crude material was purified by chromatography (SiO$_2$, ethyl acetate/heptane) to afford the title compound as a yellow crystalline solid (yield 78%). MS (m/e): 316.3 (M+H$^+$, 100%).

b) 4-(5-Methanesulfonyl-thiazol-2-yl)-piperazine-1-carboxylic acid tert-butyl ester Prepared in analogy to example 4 (c) from 4-(5-methylsulfanyl-thiazol-2-yl)-piperazine-1-carboxylic acid tert-butyl ester and meta-chloroperbenzoic acid. The title compound was obtained as a yellow crystalline solid (yield 86%). MS (m/e): 348.3 (M+H+, 100%).

c) 1-(5-Methanesulfonyl-thiazol-2-yl)-piperazine hydrochloride

Prepared in analogy to example 4 (d) from 4-(5-methanesulfonyl-thiazol-2-yl)-piperazine-1-carboxylic acid tert-butyl ester and hydrogen chloride solution. The crude material was purified by recrystallisation from ether to afford the title compound as a light brown crystalline solid (yield 99%). MS (m/e): 248.1 (M+H+, 100%).

d) (2-Isopropoxy-5-methanesulfonyl-phenyl)-[4-(5-methanesulfonyl-thiazol-2-yl)-piperazin-1-yl]-methanone

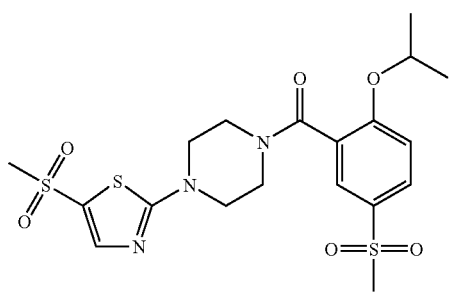

Prepared in analogy to example 1 (b) from 2-isopropoxy-5-methanesulfonyl-benzoic acid (Example A1) and 1-(5-methanesulfonyl-thiazol-2-yl)-piperazine hydrochloride. The crude material was purified by chromatography (SiO$_2$, methanol/dichloromethane) to yield the title compound as a white crystalline solid (yield 43%). MS (m/e): 488.1 (M+H$^+$, 100%), 505.0 (M+NH$_4^+$, 75%).

EXAMPLE 22

[4-(5-Methanesulfonyl-thiazol-2-yl)-piperazin-1-yl]-[5-methanesulfonyl-2-(2,2,2-trifluoro-1-methyl-ethoxy)-phenyl]-methanone

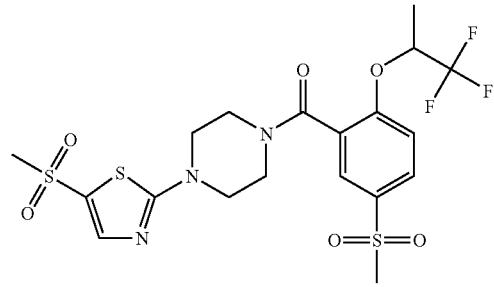

Prepared in analogy to example 1 (b) from 5-methanesulfonyl-2-(2,2,2-trifluoro-1-methyl-ethoxy)-benzoic acid (Example A2) and 1-(5-methanesulfonyl-thiazol-2-yl)-piperazine hydrochloride (Example 21(c)). The crude material was purified by chromatography (SiO$_2$, ethyl acetate/heptane) followed by trituration in ether to yield the title compound as a white crystalline solid (yield 29%). MS (m/e): 542.2 (M+H$^+$, 100%), 559.2 (M+NH$_4^+$, 65%).

EXAMPLE 23

(2-Cyclopropylmethoxy-5-methanesulfonyl-phenyl)-[4-(5-methanesulfonyl-thiazol-2-yl)-piperazin-1-yl]-methanone

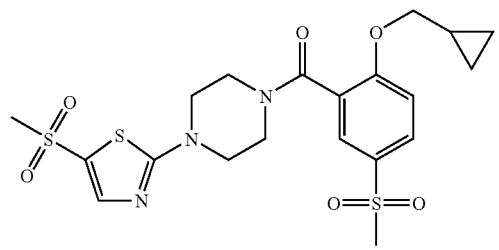

Prepared in analogy to example 1 (b) from 2-cyclopropylmethoxy-5-methanesulfonyl-benzoic acid (Example A5) and 1-(5-methanesulfonyl-thiazol-2-yl)-piperazine hydrochloride (Example 21(c)). The crude material was purified by chromatography (SiO$_2$, ethyl acetate/heptane) followed by trituration in ether to yield the title compound as a yellow crystalline solid (yield 36%). MS (m/e): 500.1 (M+H$^+$, 100%), 517.2 (M+NH$_4^+$, 69%).

EXAMPLE 24

(2-Isobutoxy-5-methanesulfonyl-phenyl)-[4-(5-methanesulfonyl-thiazol-2-yl)-piperazin-1-yl]-methanone

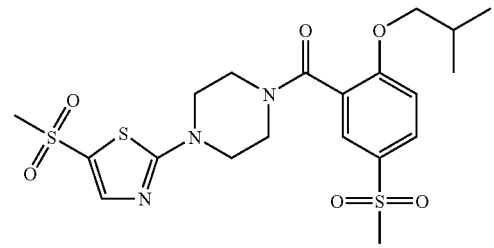

Prepared in analogy to example 1 (b) from 2-isobutoxy-5-methanesulfonyl-benzoic acid (Example A8) and 1-(5- methanesulfonyl-thiazol-2-yl)-piperazine hydrochloride (Example 21(c)). The crude material was purified by chromatography (SiO₂, ethyl acetate/heptane) followed by trituration in ether to yield the title compound as a white crystalline solid (yield 40%). MS (m/e): 502.0 (M+H⁺, 100%).

EXAMPLE 25

Rac-(2-sec-Butoxy-5-methanesulfonyl-phenyl)-[4-(5-methanesulfonyl-thiazol-2-yl)-piperazin-1-yl]-methanone

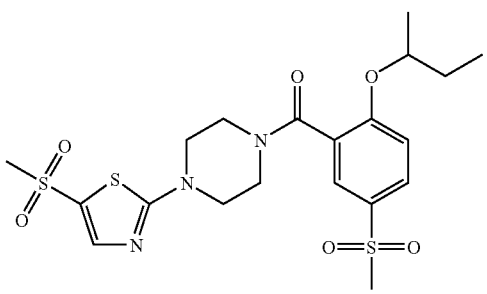

Prepared in analogy to example 1 (b) from rac-2-sec-butoxy-5-methanesulfonyl-benzoic acid (Example A10) and 1-(5-methanesulfonyl-thiazol-2-yl)-piperazine hydrochloride (Example 21(c)). The crude material was purified by chromatography (SiO₂, ethyl acetate/heptane) followed by trituration in ether to yield the title compound as an off-white crystalline solid (yield 44%). MS (m/e): 502.1 (M+H⁺, 99%), 519.3 (M+NH₄⁺, 100%).

EXAMPLE 26

[2-(2,2-Dimethyl-propoxy)-5-methanesulfonyl-phenyl]-[4-(5-methanesulfonyl-thiazol-2-yl)-piperazin-1-yl]-methanone

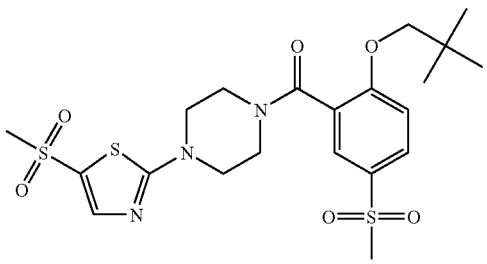

Prepared in analogy to example 1 (b) from 2-(2,2-dimethyl-propoxy)-5-methanesulfonyl-benzoic acid (Example A11) and 1-(5-methanesulfonyl-thiazol-2-yl)-piperazine hydrochloride (Example 21(c)). The crude material was purified by chromatography (SiO₂, ethyl acetate/heptane) followed by trituration in ether to yield the title compound as a white crystalline solid (yield 36%). MS (m/e): 516.2 (M+H⁺, 100%).

EXAMPLE 27

(2-Cyclohexyloxy-5-methanesulfonyl-phenyl)-[4-(5-methanesulfonyl-thiazol-2-yl)-piperazin-1-yl]-methanone

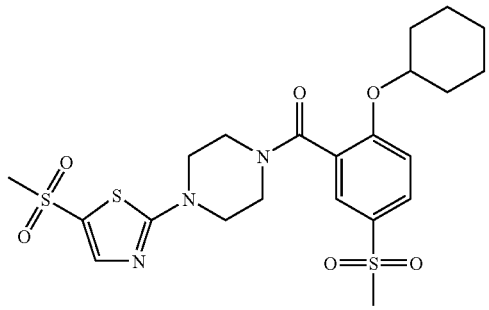

Prepared in analogy to example 1 (b) from 2-cyclohexyloxy-5-methanesulfonyl-benzoic acid (Example A7) and 1-(5-methanesulfonyl-thiazol-2-yl)-piperazine hydrochloride (Example 21(c)). The crude material was purified by chromatography (SiO₂, ethyl acetate/heptane) followed by trituration in ether to yield the title compound as a light red crystalline solid (yield 38%). MS (m/e): 528.3 (M+H⁺, 100%).

EXAMPLE 28

(2-Cyclopentyloxy-5-methanesulfonyl-phenyl)-[4-(5-methanesulfonyl-thiazol-2-yl)-piperazin-1-yl]-methanone

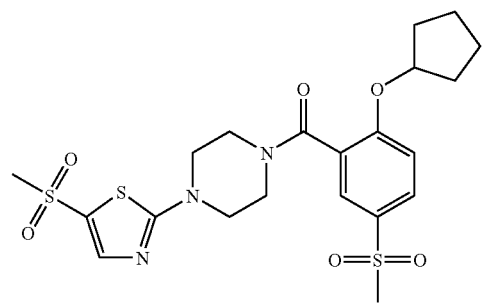

Prepared in analogy to example 1 (b) from 2-cyclopentyloxy-5-methanesulfonyl-benzoic acid (Example A4) and 1-(5-methanesulfonyl-thiazol-2-yl)-piperazine hydrochloride (Example 21(c)). The crude material was purified by chromatography (SiO₂, ethyl acetate/heptane) followed by trituration in ether to yield the title compound as an off-white crystalline solid (yield 38%). MS (m/e): 514.3 (M+H⁺, 100%).

EXAMPLE 29

[4-(5-Benzenesulfonyl-thiazol-2-yl)-piperazin-1-yl]-[2-(2,2-dimethyl-propoxy)-5-methanesulfonyl-phenyl]-methanone

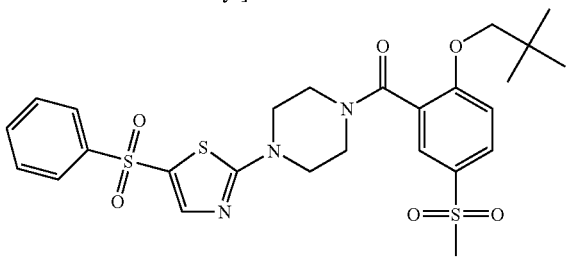

Prepared in analogy to example 1 (b) from 2-(2,2-dimethyl-propoxy)-5-methanesulfonyl-benzoic acid (Example A11) and 1-(5-benzenesulfonyl-thiazol-2-yl)-piperazine hydrochloride (Example 4(d)). The crude material was purified by chromatography (SiO$_2$, ethyl acetate/heptane) followed by trituration in ether to yield the title compound as a white crystalline solid (yield 57%). MS (m/e): 578.2 (M+H$^+$, 100%), 595.3 (M+NH$_4^+$, 92%).

EXAMPLE 30

[4-(5-Benzenesulfonyl-thiazol-2-yl)-piperazin-1-yl]-(2-cyclopentyloxy-5-methanesulfonyl-phenyl)-methanone

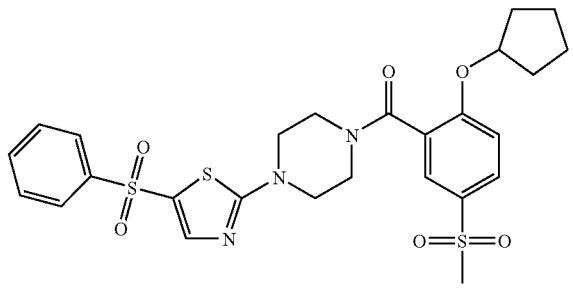

Prepared in analogy to example 1 (b) from 2-cyclopentyloxy-5-methanesulfonyl-benzoic acid (Example A4) and 1-(5-benzenesulfonyl-thiazol-2-yl)-piperazine hydrochloride (Example 4(d)). The crude material was purified by chromatography (SiO$_2$, ethyl acetate/heptane) followed by trituration in ether to yield the title compound as an off-white crystalline solid (yield 57%). MS (m/e): 576.0 (M+H$^+$, 100%), 593.3 (M+NH$_4^+$, 94%).

EXAMPLE 31

[4-(5-Benzenesulfonyl-thiazol-2-yl)-piperazin-1-yl]-(2-isobutoxy-5-methanesulfonyl-phenyl)-methanone

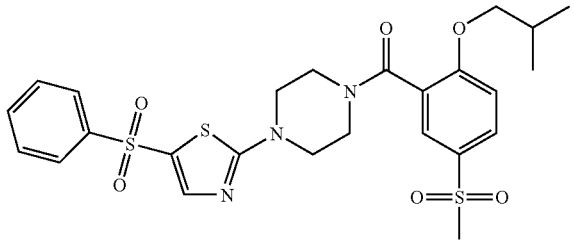

Prepared in analogy to example 1 (b) from 2-isobutoxy-5-methanesulfonyl-benzoic acid (Example A8) and 1-(5-benzenesulfonyl-thiazol-2-yl)-piperazine hydrochloride (Example 4(d)). The crude material was purified by chromatography (SiO$_2$, ethyl acetate/heptane) followed by trituration in ether to yield the title compound as an off-white crystalline solid (yield 45%). MS (m/e): 564.3 (M+H$^+$, 100%), 581.3 (M+NH$_4^+$, 94%).

EXAMPLE 32

[2-(2,2-Dimethyl-propoxy)-5-methanesulfonyl-phenyl]-[4-(5-ethanesulfonyl-thiazol-2-yl)-piperazin-1-yl]-methanone a) 4-(5-Ethylsulfanyl-thiazol-2-yl)-piperazine-1-carboxylic acid tert-butyl ester Prepared in analogy to example 4 (b) from 4-(5-bromothiazol-2-yl)-piperazine-1-carboxylic acid tert-butyl ester (Example 4(a)) and diethyl disulphide. The crude material was purified by chromatography (SiO$_2$, ethyl acetate/heptane) to afford the title compound as a white crystalline solid (yield 86%). MS (m/e): 330.3 (M+H$^+$, 100%).

b) 4-(5-Ethanesulfonyl-thiazol-2-yl)-piperazine-1-carboxylic acid tert-butyl ester Prepared in analogy to example 4 (c) from 4-(5-ethylsulfanyl-thiazol-2-yl)-piperazine-1-carboxylic acid tert-butyl ester and meta-chloroperbenzoic acid. The title compound was obtained as a yellow crystalline solid (yield 99%). MS (m/e): 362.3 (M+H$^+$, 100%), 362.3 (M+NH$_4^+$, 70%).

c) 1-(5-Ethanesulfonyl-thiazol-2-yl)-piperazine hydrochloride

Prepared in analogy to example 4 (d) from 4-(5-ethanesulfonyl-thiazol-2-yl)-piperazine-1-carboxylic acid tert-butyl ester and hydrogen chloride solution. The crude material was purified by recrystallisation from ether to afford the title compound as a light brown crystalline solid (yield 86%). MS (m/e): 262.0 (M+H$^+$, 100%).

d) [2-(2,2-Dimethyl-propoxy)-5-methanesulfonyl-phenyl]-[4-(5-ethanesulfonyl-thiazol-2-yl)-piperazin-1-yl]-methanone

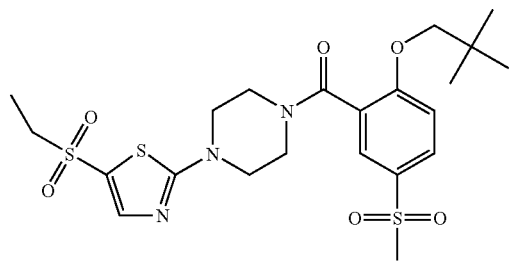

Prepared in analogy to example 1 (b) from 2-(2,2-dimethyl-propoxy)-5-methanesulfonyl-benzoic acid (Example A11) and 1-(5-ethanesulfonyl-thiazol-2-yl)-piperazine hydrochloride. The crude material was purified by chromatography (SiO$_2$, ethyl acetate/heptane) followed by trituration in ether to yield the title compound as a white crystalline solid (yield 63%). MS (m/e): 530.2 (M+H$^+$, 64%), 547.2 (M+NH$_4^+$, 100%).

EXAMPLE 33

[4-(5-Ethanesulfonyl-thiazol-2-yl)-piperazin-1-yl]-(2-isopropoxy-5-methanesulfonyl-phenyl)-methanone

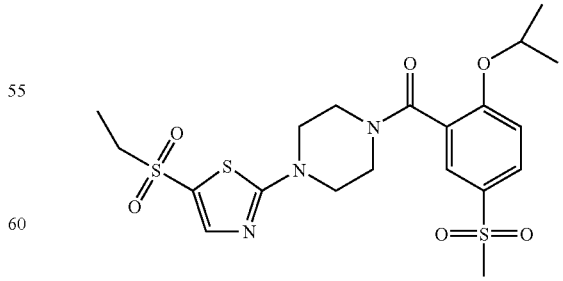

Prepared in analogy to example 1 (b) from 2-isopropoxy-5-methanesulfonyl-benzoic acid (Example A1) and 1-(5-ethanesulfonyl-thiazol-2-yl)-piperazine hydrochloride (Example 32(c)). The crude material was purified by chromatography (SiO₂, ethyl acetate/heptane) followed by trituration in ether to yield the title compound as a white crystalline solid (yield 71%). MS (m/e): 502.3 (M+H⁺, 100%), 519.3 (M+NH₄⁺, 82%).

EXAMPLE 34

[4-(4,5-Dimethyl-thiazol-2-yl)-piperazin-1-yl]-(2-isopropoxy-5-methanesulfonyl-phenyl)-methanone a) 2-Iodo-4,5-dimethyl-thiazole

Prepared in analogy to example 2 (a) from 4,5-dimethylthiazole. The crude material was purified by chromatography (SiO2, ethyl acetate/heptane) to yield the title compound as a light brown crystalline solid (yield 66%). MS (m/e): 240.1 (M+H⁺, 100%).

b) 1-(4,5-Dimethyl-thiazol-2-yl)-piperazine

Prepared in analogy to example 2 (b) from 2-iodo-4,5-dimethyl-thiazole and piperazine. The crude material was purified by chromatography (SiO2, methanol/dichloromethane) to yield the title compound as a yellow crystalline solid (yield 25%). MS (m/e): 198.3 (M+H⁺, 100%).

c) [4-(4,5-Dimethyl-thiazol-2-yl)-piperazin-1-yl]-(2-isopropoxy-5-methanesulfonyl-phenyl)-methanone

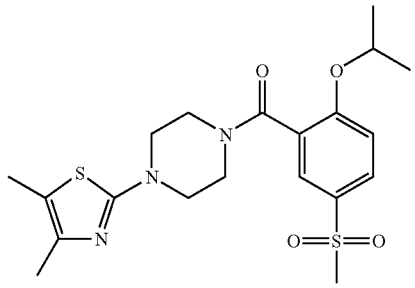

Prepared in analogy to example 1 (b) from 2-isopropoxy-5-methanesulfonyl-benzoic acid (Example A1) and 1-(4,5-dimethyl-thiazol-2-yl)-piperazine. The crude material was purified by chromatography (SiO₂, ethyl acetate/heptane) followed by trituration in ether to yield the title compound as an off-white crystalline solid (yield 65%). MS (m/e): 584.3 (M+H⁺, 100%), 601.4 (M+NH₄⁺, 60%).

EXAMPLE 35

(2-Cyclopentyloxy-5-methanesulfonyl-phenyl)-[4-(5-ethanesulfonyl-thiazol-2-yl)-piperazin-1-yl]-methanone

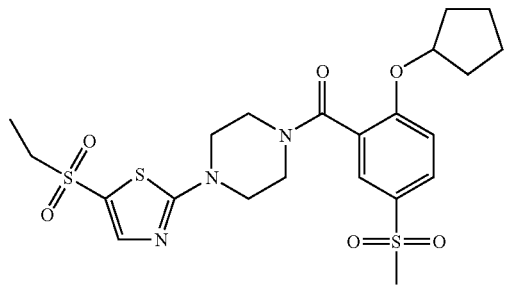

Prepared in analogy to example 1 (b) from 2-cyclopentyloxy-5-methanesulfonyl-benzoic acid (Example A4) and 1-(5-ethanesulfonyl-thiazol-2-yl)-piperazine hydrochloride (Example 32(c)). The crude material was purified by chromatography (SiO₂, ethyl acetate/heptane) followed by trituration in ether to yield the title compound as a white crystalline solid (yield 77%). MS (m/e): 528.3 (M+H⁺, 35%), 545.4 (M+NH₄⁺, 100%).

EXAMPLE 36

[4-(5-Ethanesulfonyl-thiazol-2-yl)-piperazin-1-yl]-[5-methanesulfonyl-2-(2,2,2-trifluoro-1-methyl-ethoxy)-phenyl]-methanone

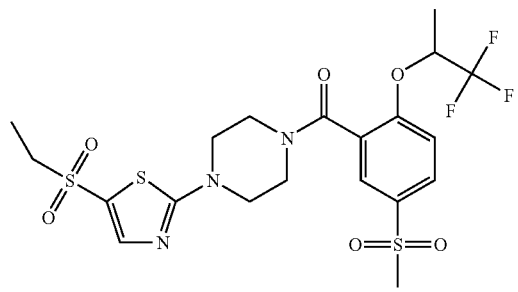

Prepared in analogy to example 1 (b) from 5-methanesulfonyl-2-(2,2,2-trifluoro-1-methyl-ethoxy)-benzoic acid (Example A2) and 1-(5-ethanesulfonyl-thiazol-2-yl)-piperazine hydrochloride (Example 32(c)). The crude material was purified by chromatography (SiO₂, ethyl acetate/heptane) followed by trituration in ether to yield the title compound as a white crystalline solid (yield 61%). MS (m/e): 556.3 (M+H⁺, 100%), 573.3 (M+NH₄⁺, 55%).

EXAMPLE 37

[4-(5-Ethanesulfonyl-thiazol-2-yl)-piperazin-1-yl]-[5-methanesulfonyl-2-(2,2,2-trifluoro-ethoxy)-phenyl]-methanone

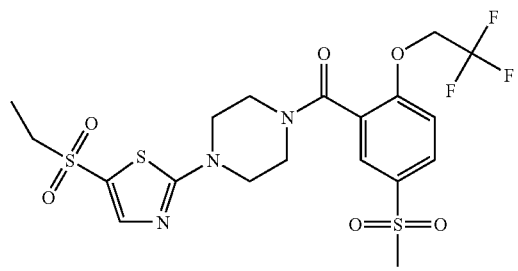

Prepared in analogy to example 1 (b) from 5-methanesulfonyl-2-(2,2,2-trifluoro-ethoxy)-benzoic acid (Example A3) and 1-(5-ethanesulfonyl-thiazol-2-yl)-piperazine hydrochloride (Example 32(c)). The crude material was purified by chromatography (SiO₂, ethyl acetate/heptane) followed by trituration in ether to yield the title compound as a white crystalline solid (yield 72%). MS (m/e): 542.2 (M+H⁺, 100%), 559.3 (M+NH₄⁺, 60%).

EXAMPLE 38

{4-[5-(Butane-1-sulfonyl)-thiazol-2-yl]-piperazin-1-yl}-(2-isopropoxy-5-methanesulfonyl-phenyl)-methanone a) 4-(5-Butylsulfanyl-thiazol-2-yl)-piperazine-1-carboxylic acid tert-butyl ester Prepared in analogy to example 4 (b) from 4-(5-bromo-thiazol-2-yl)-piperazine-1-carboxylic acid tert-butyl ester (Example 4(a)) and dibutyl disulphide. The crude material was purified by chromatography (SiO$_2$, ethyl acetate/heptane) to afford the title compound as a colourless oil (yield 93%). MS (m/e): 358.3 (M+H$^+$, 100%).

b) 4-[5-(Butane-1-sulfonyl)-thiazol-2-yl]-piperazine-1-carboxylic acid tert-butyl ester Prepared in analogy to example 4 (c) from 4-(5-butylsulfanyl-thiazol-2-yl)-piperazine-1-carboxylic acid tert-butyl ester and meta-chloroperbenzoic acid. The title compound was obtained as a yellow crystalline solid (yield 82%). MS (m/e): 390.3 (M+H$^+$, 100%), 407.3 (M+NH$_4^+$, 80%).

c) 1-[5-(Butane-1-sulfonyl)-thiazol-2-yl]-piperazine hydrochloride

Prepared in analogy to example 4 (d) from 4-[5-(butane-1-sulfonyl)-thiazol-2-yl]-piperazine-1-carboxylic acid tert-butyl ester and hydrogen chloride solution. The crude material was purified by recrystallisation from ether to afford the title compound as an off-white crystalline solid (yield 92%). MS (m/e): 290.0 (M+H$^+$, 100%).

d) {4-[5-(Butane-1-sulfonyl)-thiazol-2-yl]-piperazin-1-yl}-(2-isopropoxy-5-methanesulfonyl-phenyl)-methanone

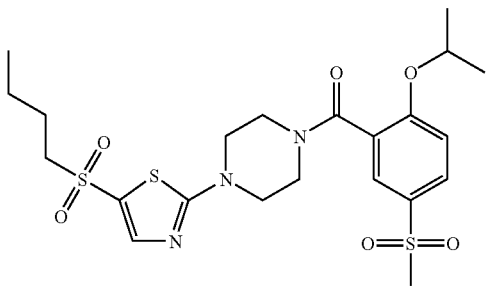

Prepared in analogy to example 1 (b) from 2-isopropoxy-5-methanesulfonyl-benzoic acid (Example A1) and 1-[5-(butane-1-sulfonyl)-thiazol-2-yl]-piperazine hydrochloride. The crude material was purified by chromatography (SiO$_2$, ethyl acetate/heptane) followed by trituration in ether to yield the title compound as a white crystalline solid (yield 54%). MS (m/e): 530.3 (M+H$^+$, 35%), 547.5 (M+NH$_4^+$, 100%).

EXAMPLE 39

{4-[5-(Butane-1-sulfonyl)-thiazol-2-yl]-piperazin-1-yl}-[5-methanesulfonyl-2-(2,2,2-trifluoro-1-methyl-ethoxy)-phenyl]-methanone

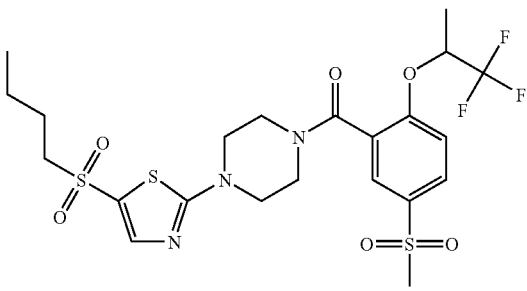

Prepared in analogy to example 1 (b) from 5-methanesulfonyl-2-(2,2,2-trifluoro-1-methyl-ethoxy)-benzoic acid (Example A2) and 1-[5-(butane-1-sulfonyl)-thiazol-2-yl]-piperazine hydrochloride (Example 38(c)). The crude material was purified by chromatography (SiO$_2$, ethyl acetate/ heptane) followed by trituration in ether to yield the title compound as a white crystalline solid (yield 65%). MS (m/e): 584.3 (M+H$^+$, 100%), 601.4 (M+NH$_4^+$, 60%).

EXAMPLE 40

{4-[5-(Butane-1-sulfonyl)-thiazol-2-yl]-piperazin-1-yl}-[5-methanesulfonyl-2-(2,2,2-trifluoro-ethoxy)-phenyl]-methanone

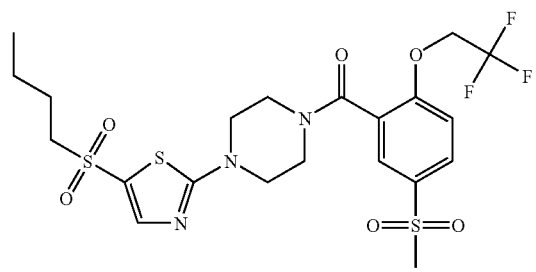

Prepared in analogy to example 1 (b) from 5-methanesulfonyl-2-(2,2,2-trifluoro-ethoxy)-benzoic acid (Example A3) and 1-[5-(butane-1-sulfonyl)-thiazol-2-yl]-piperazine hydrochloride (Example 38(c)). The crude material was purified by chromatography (SiO$_2$, ethyl acetate/heptane) followed by trituration in ether to yield the title compound as a white crystalline solid (yield 63%). MS (m/e): 570.4 (M+H$^+$, 15%), 587.3 (M+NH$_4^+$, 100%).

EXAMPLE 41

{4-[5-(Butane-1-sulfonyl)-thiazol-2-yl]-piperazin-1-yl}-(2-cyclopentyloxy-5-methanesulfonyl-phenyl)-methanone

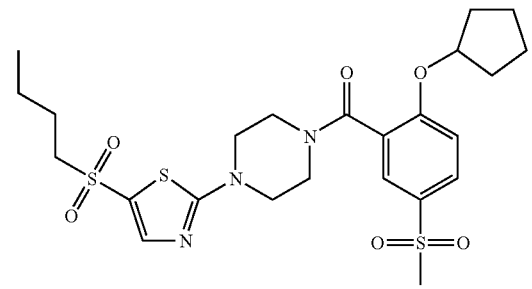

Prepared in analogy to example 1 (b) from 2-cyclopentyloxy-5-methanesulfonyl-benzoic acid (Example A4) and 1-[5-(butane-1-sulfonyl)-thiazol-2-yl]-piperazine hydrochloride (Example 38(c)). The crude material was purified by chromatography (SiO$_2$, ethyl acetate/heptane) followed by trituration in ether to yield the title compound as a white crystalline solid (yield 71%). MS (m/e): 556.3 (M+H$^+$, 35%), 573.5 (M+NH$_4^+$, 100%).

EXAMPLE 42

{4-[5-(Butane-1-sulfonyl)-thiazol-2-yl]-piperazin-1-yl}-[2-(2,2-dimethyl-propoxy)-5-methanesulfonyl-phenyl]-methanone

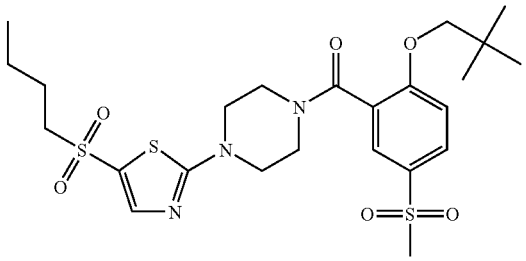

Prepared in analogy to example 1 (b) from 2-(2,2-dimethyl-propoxy)-5-methanesulfonyl-benzoic acid (Example A11) and 1-[5-(butane-1-sulfonyl)-thiazol-2-yl]-piperazine hydrochloride (Example 38(c)). The crude material was purified by chromatography (SiO$_2$, ethyl acetate/heptane) followed by trituration in ether to yield the title compound as a white crystalline solid (yield 69%). MS (m/e): 558.4 (M+H$^+$, 20%), 575.4 (M+NH$_4^+$, 100%).

EXAMPLE 43

{4-[5-(Butane-1-sulfonyl)-thiazol-2-yl]-piperazin-1-yl}-(5-methanesulfonyl-2-morpholin-4-yl-phenyl)-methanone

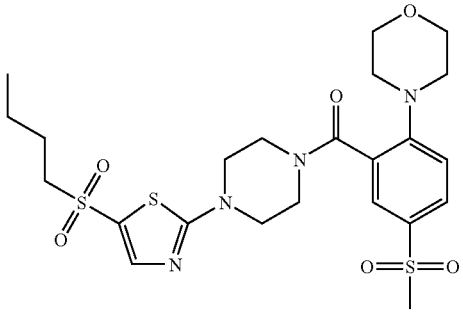

Prepared in analogy to example 1 (b) from 5-Methanesulfonyl-2-morpholin-4-yl-benzoic acid (Example A13) and 1-[5-(butane-1-sulfonyl)-thiazol-2-yl]-piperazine hydrochloride (Example 38(c)). The crude material was purified by chromatography (SiO$_2$, ethyl acetate/heptane) followed by trituration in ether to yield the title compound as a light red crystalline solid (yield 60%). MS (m/e): 557.2 (M+H$^+$, 65%), 574.4 (M+NH$_4^+$, 100%).

EXAMPLE 44

(2-Isopropoxy-5-methanesulfonyl-phenyl)-{4-[5-(propane-2-sulfonyl)-thiazol-2-yl]-piperazin-1-yl}-methanone a) 4-[5-(Propane-2-sulfonyl)-thiazol-2-yl]-piperazine-1-carboxylic acid tert-butyl ester To a solution of 0.83 mmol 4-(5-ethanesulfonyl-thiazol-2-yl)-piperazine-1-carboxylic acid tert-butyl ester (Example 32(b)) in 3 ml tetrahydrofuran at −78° C. was added dropwise 1.08 mmol potassium bis(trimethylsilylamide) solution (0.91 M in tetrahydrofuran). After 3 min, a solution of 1.24 mmol iodomethane in 2 ml tetrahydrofuran was added dropwise and stirring continued for 10 min at −78° C. The reaction mixture was then allowed to warm to room temperature and poured onto tetrahydrofuran/ethyl acetate (1:1). The mixture was washed with brine and the organic phase was dried over sodium sulphate and concentrated in vacuo. Chromatography (SiO$_2$, ethyl acetate/heptane) afforded the title compound as a white crystalline solid (yield 30%). MS (m/e): 376.1 (M+H$^+$, 100%).

b) 1-[5-(Propane-2-sulfonyl)-thiazol-2-yl]-piperazine hydrochloride

Prepared in analogy to example 4 (d) from 4-[5-(propane-2-sulfonyl)-thiazol-2-yl]-piperazine-1-carboxylic acid tert-butyl ester and hydrogen chloride solution. The crude material was purified by recrystallisation from ether to afford the title compound as a white crystalline solid (yield 97%). MS (m/e): 276.4 (M+H$^+$, 100%).

c) (2-Isopropoxy-5-methanesulfonyl-phenyl)-{4-[5-(propane-2-sulfonyl)-thiazol-2-yl]-piperazin-1-yl}-methanone

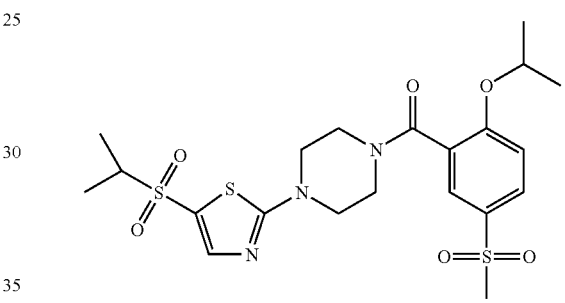

Prepared in analogy to example 1 (b) from 2-isopropoxy-5-methanesulfonyl-benzoic acid (Example A1) and 1-[5-(propane-2-sulfonyl)-thiazol-2-yl]-piperazine hydrochloride. The crude material was purified by chromatography (SiO$_2$, ethyl acetate/heptane) followed by trituration in ether to yield the title compound as a white crystalline solid (yield 67%). MS (m/e): 516.3 (M+H$^+$, 100%), 533.3 (M+NH$_4^+$, 85%).

EXAMPLE 45

(2-Isopropoxy-5-methanesulfonyl-phenyl)-{4-[5-(pyridine-2-sulfonyl)-thiazol-2-yl]-piperazin-1-yl}-methanone a) 4-[5-(Pyridin-2-ylsulfanyl)-thiazol-2-yl]-piperazine-1-carboxylic acid tert-butyl ester Prepared in analogy to example 4 (b) from 4-(5-bromothiazol-2-yl)-piperazine-1-carboxylic acid tert-butyl ester (Example 4(a)) and 2,2'-dithiodipyridine. The crude material was purified by chromatography (SiO$_2$, ethyl acetate/heptane) to afford the title compound as a yellow crystalline solid (yield 94%). MS (m/e): 379.1 (M+H$^+$, 100%).

b) 4-[5-(Pyridine-2-sulfonyl)-thiazol-2-yl]-piperazine-1-carboxylic acid tert-butyl ester Prepared in analogy to example 4 (c) from 4-[5-(pyridin-2-ylsulfanyl)-thiazol-2-yl]-piperazine-1-carboxylic acid tert-butyl ester and meta-chloroperbenzoic acid. The crude material was purified by chromatography (SiO$_2$, ethyl acetate/heptane) to afford the title compound as a white crystalline solid (yield 54%). MS (m/e): 411.3 (M+H$^+$, 100%).

c) 1-[5-(Pyridine-2-sulfonyl)-thiazol-2-yl]-piperazine hydrochloride

Prepared in analogy to example 4 (d) from 4-[5-(pyridine-2-sulfonyl)-thiazol-2-yl]-piperazine-1-carboxylic acid tert-butyl ester and hydrogen chloride solution. The crude material was purified by recrystallisation from ether to afford the title compound as an off-white crystalline solid (yield 99%). MS (m/e): 311.0 (M+H$^+$, 100%).

d) (2-Isopropoxy-5-methanesulfonyl-phenyl)-{4-[5-(pyridine-2-sulfonyl)-thiazol-2-yl]-piperazin-1-yl}-methanone

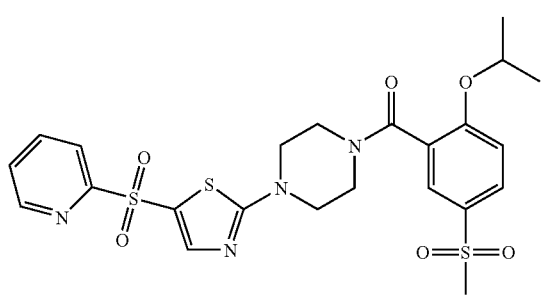

Prepared in analogy to example 1 (b) from 2-isopropoxy-5-methanesulfonyl-benzoic acid (Example A1) and 1-[5-(pyridine-2-sulfonyl)-thiazol-2-yl]-piperazine hydrochloride. The crude material was purified by chromatography (SiO$_2$, ethyl acetate/heptane) followed by trituration in ether to yield the title compound as a white crystalline solid (yield 90%). MS (m/e): 551.2 (M+H$^+$, 100%).

EXAMPLE 46

(2-Isopropoxy-5-methanesulfonyl-phenyl)-{4-[5-(pyridine-3-sulfonyl)-thiazol-2-yl]-piperazin-1-yl}-methanone a) 4-[5-(Pyridin-3-ylsulfanyl)-thiazol-2-yl]-piperazine-1-carboxylic acid tert-butyl ester Prepared in analogy to example 4 (b) from 4-(5-bromo-thiazol-2-yl)-piperazine-1-carboxylic acid tert-butyl ester (Example 4(a)) and 3,3'-dithiodipyridine. The crude material was purified by chromatography (SiO$_2$, ethyl acetate/heptane) to afford the title compound as an orange oil (yield 55%). MS (m/e): 379.1 (M+H$^+$, 100%).

b) 4-[5-(Pyridine-3-sulfonyl)-thiazol-2-yl]-piperazine-1-carboxylic acid tert-butyl ester Prepared in analogy to example 4 (c) from 4-[5-(pyridin-3-ylsulfanyl)-thiazol-2-yl]-piperazine-1-carboxylic acid tert-butyl ester and meta-chloroperbenzoic acid. The crude material was purified by chromatography (SiO$_2$, ethyl acetate/heptane) to afford the title compound as a white crystalline solid (yield 41%). MS (m/e): 411.1 (M+H$^+$, 100%).

c) 1-[5-(Pyridine-3-sulfonyl)-thiazol-2-yl]-piperazine hydrochloride

Prepared in analogy to example 4 (d) from 4-[5-(pyridine-3-sulfonyl)-thiazol-2-yl]-piperazine-1-carboxylic acid tert-butyl ester and hydrogen chloride solution. The crude material was purified by recrystallisation from ether to afford the title compound as an off-white crystalline solid (yield 99%). MS (m/e): 311.0 (M+H$^+$, 100%).

d) (2-Isopropoxy-5-methanesulfonyl-phenyl)-{4-[5-(pyridine-3-sulfonyl)-thiazol-2-yl]-piperazin-1-yl}-methanone

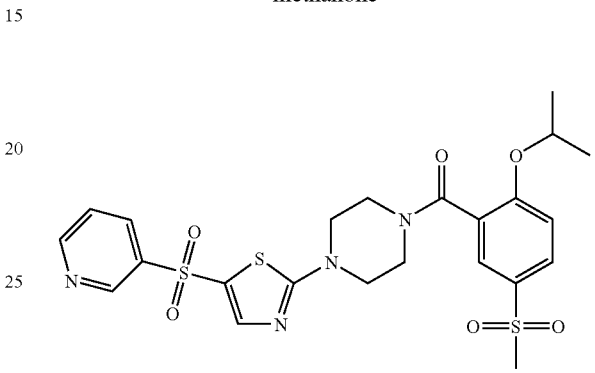

Prepared in analogy to example 1 (b) from 2-isopropoxy-5-methanesulfonyl-benzoic acid (Example A1) and 1-[5-(pyridine-3-sulfonyl)-thiazol-2-yl]-piperazine hydrochloride. The crude material was purified by chromatography (SiO$_2$, ethyl acetate/heptane) followed by trituration in ether to yield the title compound as an off-white crystalline solid (yield 87%). MS (m/e): 551.3 (M+H$^+$, 100%).

EXAMPLE 47

[5-Methanesulfonyl-2-(2,2,2-trifluoro-1-methyl-ethoxy)-phenyl]-{4-[5-(pyridine-2-sulfonyl)-thiazol-2-yl]-piperazin-1-yl}-methanone

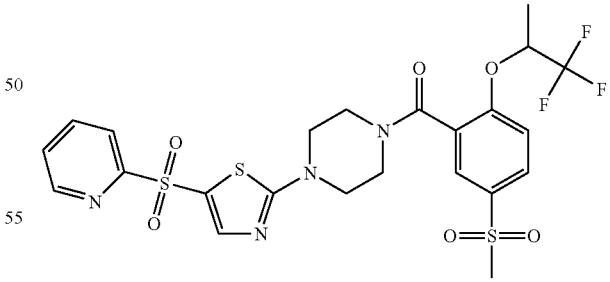

Prepared in analogy to example 1 (b) from 5-methanesulfonyl-2-(2,2,2-trifluoro-1-methyl-ethoxy)-benzoic acid (Example A2) and 1-[5-(pyridine-2-sulfonyl)-thiazol-2-yl]-piperazine hydrochloride (Example 45(c)). The crude material was purified by chromatography (SiO$_2$, ethyl acetate/heptane) followed by trituration in ether to yield the title compound as an off-white crystalline solid (yield 68%). MS (m/e): 605.0 (M+H$^+$, 100%).

EXAMPLE 48

[5-Methanesulfonyl-2-(2,2,2-trifluoro-1-methyl-ethoxy)-phenyl]-{4-[5-(pyridine-3-sulfonyl)-thiazol-2-yl]-piperazin-1-yl}-methanone

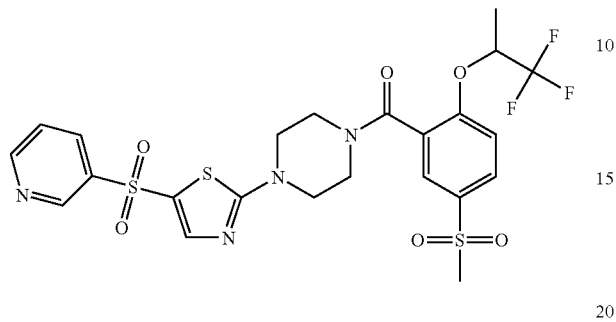

Prepared in analogy to example 1 (b) from 5-methanesulfonyl-2-(2,2,2-trifluoro-1-methyl-ethoxy)-benzoic acid (Example A2) and 1-[5-(pyridine-3-sulfonyl)-thiazol-2-yl]-piperazine hydrochloride (Example 46(c)). The crude material was purified by chromatography (SiO$_2$, ethyl acetate/heptane) followed by trituration in ether to yield the title compound as a light brown crystalline solid (yield 49%). MS (m/e): 605.2 (M+H$^+$, 100%).

EXAMPLE 49

(2-Isopropoxy-5-methanesulfonyl-phenyl)-[4-(4-trifluoromethyl-thiazol-2-yl)-piperazin-1-yl]-methanone a) 1-(4-Trifluoromethyl-thiazol-2-yl)-piperazine To a solution of 6.89 mmol 1-piperazinecarbothioamide in 10 ml ethanol was added 8.26 mmol 3-bromo-1,1,1-trifluoroacetone and the mixture was heated at 70° C. for 2 h. The mixture was then concentrated in vacuo and the residue resuspended in dichloromethane. Insoluble material was removed by filtration and the filtrate was concentrated in vacuo. Chromatography (SiO2, methanol/dichloromethane) afforded the title compound as a yellow crystalline solid (yield 41%). MS (m/e): 238.1 (M+H+, 100%).

b) (2-Isopropoxy-5-methanesulfonyl-phenyl)-[4-(4-trifluoromethyl-thiazol-2-yl)-piperazin-1-yl]-methanone

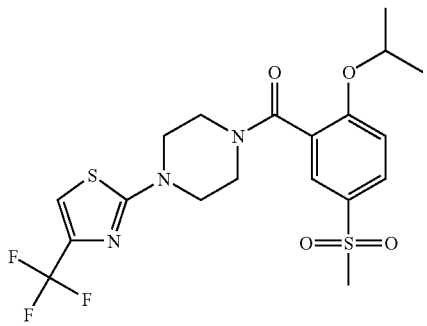

Prepared in analogy to example 1 (b) from 2-isopropoxy-5-methanesulfonyl-benzoic acid (Example A1) and 1-(4-trifluoromethyl-thiazol-2-yl)-piperazine. The crude material was purified by chromatography (SiO$_2$, ethyl acetate/heptane) followed by trituration in pentane to yield the title compound as a crystalline white solid (yield 55%). MS (m/e): 478.0 (M+H$^+$, 100%).

EXAMPLE 50

[5-Methanesulfonyl-2-(2,2,2-trifluoro-1-methyl-ethoxy)-phenyl]-[4-(4-trifluoromethyl-thiazol-2-yl)-piperazin-1-yl]-methanone

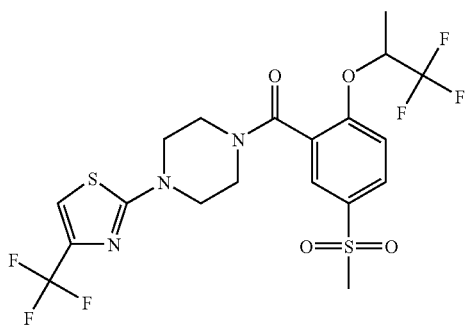

Prepared in analogy to example 1 (b) from 5-methanesulfonyl-2-(2,2,2-trifluoro-1-methyl-ethoxy)-benzoic acid (Example A2) and 1-(4-trifluoromethyl-thiazol-2-yl)-piperazine (Example 49(a)). The crude material was purified by chromatography (SiO$_2$, ethyl acetate/heptane) followed by trituration in pentane to yield the title compound as a crystalline white solid (yield 48%). MS (m/e): 531.8 (M+H$^+$, 100%).

EXAMPLE 51

(2-Cyclopentyloxy-5-methanesulfonyl-phenyl)-[4-(4-trifluoromethyl-thiazol-2-yl)-piperazin-1-yl]-methanone

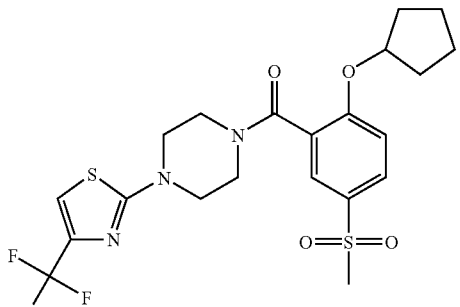

Prepared in analogy to example 1 (b) from 2-cyclopentyloxy-5-methanesulfonyl-benzoic acid (Example A4) and 1-(4-trifluoromethyl-thiazol-2-yl)-piperazine (Example 49(a)). The crude material was purified by chromatography (SiO$_2$, ethyl acetate/heptane) followed by trituration in pentane to yield the title compound as a crystalline white solid (yield 71%). MS (m/e): 504.0 (M+H$^+$, 100%).

EXAMPLE 52

(2-Isopropoxy-5-methanesulfonyl-phenyl)-{4-[5-(pyridine-4-sulfonyl)-thiazol-2-yl]-piperazin-1-yl}-methanone a) 4-[5-(Pyridin-4-ylsulfanyl)-thiazol-2-yl]-piperazine-1-carboxylic acid tert-butyl ester Prepared in analogy to example 4 (b) from 4-(5-bromo-thiazol-2-yl)-piperazine-1-carboxylic acid tert-butyl ester (Example 4(a)) and 4,4'-dithiodipyridine. The crude material was purified by chromatography (SiO$_2$, ethyl acetate/heptane) to afford the title compound as a yellow oil (yield 79%). MS (m/e): 379.3 (M+H$^+$, 100%).

b) 4-[5-(Pyridine-4-sulfonyl)-thiazol-2-yl]-piperazine-1-carboxylic acid tert-butyl ester Prepared in analogy to example 4 (c) from 4-[5-(pyridin-4-ylsulfanyl)-thiazol-2-yl]-piperazine-1-carboxylic acid tert-butyl ester and meta-chloroperbenzoic acid. The crude material was purified by chromatography (SiO$_2$, ethyl acetate/heptane) to afford the title compound as a yellow crystalline solid (yield 37%). MS (m/e): 411.3 (M+H$^+$, 100%).

c) 1-[5-(Pyridine-4-sulfonyl)-thiazol-2-yl]-piperazine hydrochloride

Prepared in analogy to example 4 (d) from 4-[5-(pyridine-4-sulfonyl)-thiazol-2-yl]-piperazine-1-carboxylic acid tert-butyl ester and hydrogen chloride solution. The crude material was purified by recrystallisation from ether to afford the title compound as a light yellow crystalline solid (yield 99%). MS (m/e): 311.0 (M+H$^+$, 100%).

d) (2-Isopropoxy-5-methanesulfonyl-phenyl)-{4-[5-(pyridine-4-sulfonyl)-thiazol-2-yl]-piperazin-1-yl}-methanone

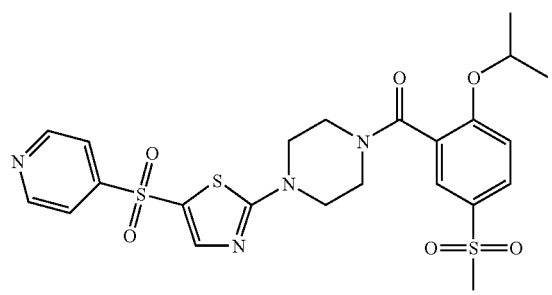

Prepared in analogy to example 1 (b) from 2-isopropoxy-5-methanesulfonyl-benzoic acid (Example A1) and 1-[5-(pyridine-4-sulfonyl)-thiazol-2-yl]-piperazine hydrochloride. The crude material was purified by chromatography (SiO$_2$, ethyl acetate/heptane) followed by trituration in ether to yield the title compound as a light red crystalline solid (yield 32%). MS (m/e): 551.2 (M+H$^+$, 100%).

EXAMPLE 53

[5-Methanesulfonyl-2-(2,2,2-trifluoro-1-methyl-ethoxy)-phenyl]-{4-[5-(pyridine-4-sulfonyl)-thiazol-2-yl]-piperazin-1-yl}-methanone

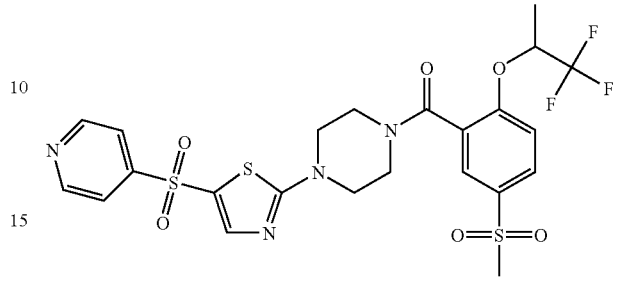

Prepared in analogy to example 1 (b) from 5-methanesulfonyl-2-(2,2,2-trifluoro-1-methyl-ethoxy)-benzoic acid (Example A2) and 1-[5-(pyridine-4-sulfonyl)-thiazol-2-yl]-piperazine hydrochloride (Example 52(c)). The crude material was purified by chromatography (SiO$_2$, ethyl acetate/heptane) followed by trituration in ether to yield the title compound as a light yellow crystalline solid (yield 32%). MS (m/e): 551.2 (M+H$^+$, 100%).

EXAMPLE 54

(2-Isopropoxy-5-methanesulfonyl-phenyl)-[4-(5-methyl-4-trifluoromethyl-thiazol-2-yl)-piperazin-1-yl]-methanone a) 1-(5-Methyl-4-trifluoromethyl-thiazol-2-yl)-piperazine

Prepared in analogy to example 49 (a) from 1-piperazinecarbothioamide and 3-bromo-1,1,1-trifluoro-2-butanone. The crude material was purified by chromatography (SiO$_2$, methanol/dichloromethane) to yield the title compound as a white crystalline solid (yield 25%). MS (m/e): 252.1 (M+H$^+$, 100%).

b) (2-Isopropoxy-5-methanesulfonyl-phenyl)-[4-(5-methyl-4-trifluoromethyl-thiazol-2-yl)-piperazin-1-yl]-methanone

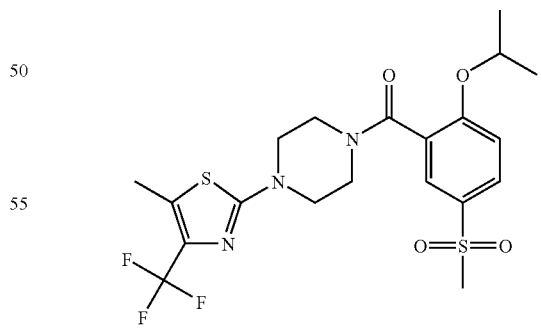

Prepared in analogy to example 1 (b) from 2-isopropoxy-5-methanesulfonyl-benzoic acid (Example A1) and 1-(5-methyl-4-trifluoromethyl-thiazol-2-yl)-piperazine. The crude material was purified by chromatography (SiO$_2$, ethyl acetate/heptane) followed by trituration in ether to yield the title compound as a white crystalline solid (yield 60%). MS (m/e): 492.3 (M+H$^+$, 100%).

EXAMPLE 55

[5-Methanesulfonyl-2-(2,2,2-trifluoro-1-methyl-ethoxy)-phenyl]-[4-(5-methyl-4-trifluoromethyl-thiazol-2-yl)-piperazin-1-yl]-methanone

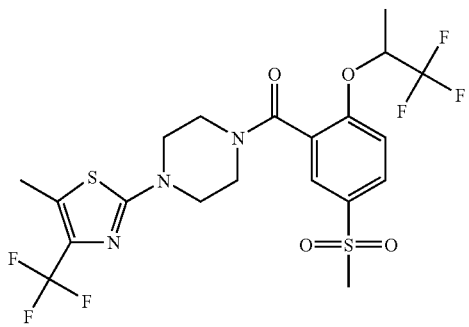

Prepared in analogy to example 1 (b) from 5-methanesulfonyl-2-(2,2,2-trifluoro-1-methyl-ethoxy)-benzoic acid (Example A2) and 1-(5-methyl-4-trifluoromethyl-thiazol-2-yl)-piperazine (Example 54(a)). The crude material was purified by chromatography (SiO$_2$, ethyl acetate/heptane) followed by trituration in pentane to yield the title compound as a white crystalline solid (yield 61%). MS (m/e): 546.3 (M+H$^+$, 100%).

EXAMPLE 56

(2-Isopropoxy-5-methanesulfonyl-phenyl)-{4-[4-(2,2,2-trifluoro-ethyl)-thiazol-2-yl]-piperazin-1-yl}-methanone a) 1-[4-(2,2,2-Trifluoro-ethyl)-thiazol-2-yl]-piperazine

Prepared in analogy to example 49 (a) from 1-piperazinecarbothioamide and 1-bromo-4,4,4-trifluoro-butan-2-one. The crude material was purified by chromatography (SiO$_2$, methanol/dichloromethane) to yield the title compound as a brown oil (yield 24%). MS (m/e): 252.3 (M+H$^+$, 100%).

b) (2-Isopropoxy-5-methanesulfonyl-phenyl)-{4-[4-(2,2,2-trifluoro-ethyl)-thiazol-2-yl]-piperazin-1-yl}-methanone

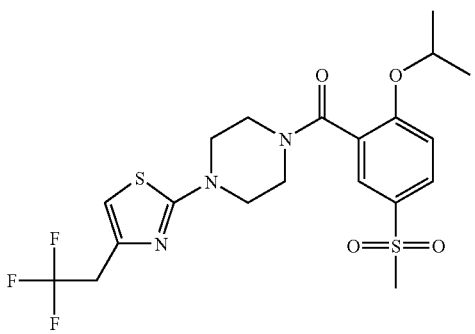

Prepared in analogy to example 1 (b) from 2-isopropoxy-5-methanesulfonyl-benzoic acid (Example A1) and 1-[4-(2,2,2-trifluoro-ethyl)-thiazol-2-yl]-piperazine. The crude material was purified by chromatography (SiO$_2$, ethyl acetate/heptane) followed by trituration in pentane to yield the title compound as a white crystalline solid (yield 28%). MS (m/e): 492.1 (M+H$^+$, 100%).

EXAMPLE 57

[5-Methanesulfonyl-2-(2,2,2-trifluoro-1-methyl-ethoxy)-phenyl]-{4-[4-(2,2,2-trifluoro-ethyl)-thiazol-2-yl]-piperazin-1-yl}-methanone

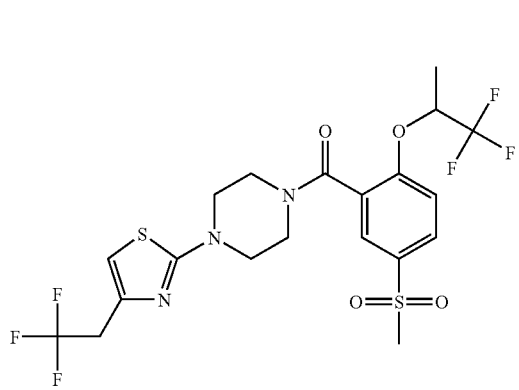

Prepared in analogy to example 1 (b) from 5-methanesulfonyl-2-(2,2,2-trifluoro-1-methyl-ethoxy)-benzoic acid (Example A2) and 1-[4-(2,2,2-trifluoro-ethyl)-thiazol-2-yl]-piperazine (Example 56(a)). The crude material was purified by chromatography (SiO$_2$, ethyl acetate/heptane) followed by trituration in pentane to yield the title compound as a white crystalline solid (yield 29%). MS (m/e): 546.3 (M+H$^+$, 100%).

EXAMPLE 58

(2-Isopropoxy-5-methanesulfonyl-phenyl)-[4-(5-trifluoromethyl-thiazol-2-yl)-piperazin-1-yl]-methanone a) 2-Benzenesulfonyl-3-trifluoromethyl-oxirane

To a solution of 25.4 mmol 3,3,3-trifluoro-1-(phenylsulphonyl)prop-1-ene in 80 ml acetonitrile were added 30.5 mmol peracetic acid (39% solution in acetic acid) and 101 mmol potassium carbonate. The mixture was heated at 60° C. for 4 h. The reaction mixture was then diluted with ethyl acetate/tetrahydrofuran (1:1) and was washed with brine. The organic phase was dried over sodium sulfate and concentrated in vacuo to afford the title compound as a light yellow crystalline solid (yield 90%). EI-MS (m/e): 252.0 (M$^+$, 15%), 125.1 (PhSO$^+$, 100%), 77.2 (Ph$^+$, 37%).

b) 4-(5-Trifluoromethyl-thiazol-2-yl)-piperazine-1-carboxylic acid tert-butyl ester To a solution of 17.5 mmol 2-benzenesulfonyl-3-trifluoromethyl-oxirane in 20 ml N,N-dimethylformamide was added 15.9 mmol 4-thiocarbamoyl-piperazine-1-carboxylic acid tert-butyl ester (prepared from tert-butyl 1-piperazinecarboxylate, 1,1'-thiocarbonyldiimidazole and ammonia according to the procedure of J. Med. Chem. 1998, 41, 5037–5054). The mixture was heated at 90° C. for 10 h. The reaction mixture was then concentrated in vacuo and the residue purified by chromatography (SiO$_2$, ethyl acetate/heptane) to afford the title compound as an orange crystalline solid (yield 26%). MS (m/e): 338.1 (M+H$^+$, 100%).

c) 1-(5-Trifluoromethyl-thiazol-2-yl)-piperazine hydrochloride

To a solution of 3.59 mmol 4-(5-trifluoromethyl-thiazol-2-yl)-piperazine-1-carboxylic acid tert-butyl ester in 20 ml dioxane was added dropwise 53.8 mmol hydrogen chloride solution (4 M in dioxane) and the mixture was stirred at 90° C. for 4 h. The reaction mixture was then cooled to 0° C. and diluted with ether. The resulting crystals were collected by filtration and washed with ether to afford the title compound as an off-white crystalline solid (yield 99%). MS (m/e): 238.1 (M+H+, 100%).

d) (2-Isopropoxy-5-methanesulfonyl-phenyl)-[4-(5-trifluoromethyl-thiazol-2-yl)-piperazin-1-yl]-methanone

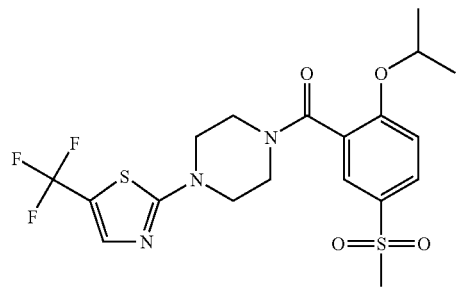

Prepared in analogy to example 1 (b) from 2-isopropoxy-5-methanesulfonyl-benzoic acid (Example A1) and 1-(5-trifluoromethyl-thiazol-2-yl)-piperazine hydrochloride. The crude material was purified by chromatography (SiO$_2$, ethyl acetate/heptane) followed by trituration in pentane to yield the title compound as a white crystalline solid (yield 28%). MS (m/e): 478.3 (M+H$^+$, 100%).

EXAMPLE 59

[5-Methanesulfonyl-2-(2,2,2-trifluoro-1-methyl-ethoxy)-phenyl]-[4-(5-trifluoromethyl-thiazol-2-yl)-piperazin-1-yl]-methanone

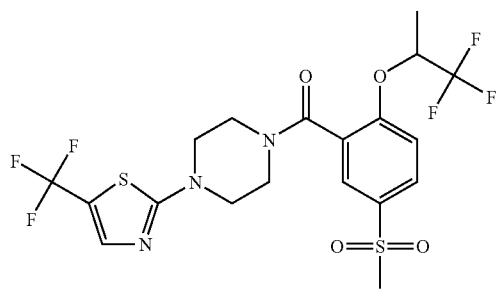

Prepared in analogy to example 1 (b) from 5-methanesulfonyl-2-(2,2,2-trifluoro-1-methyl-ethoxy)-benzoic acid (Example A2) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the title compound as an off-white crystalline solid (yield 64%). MS (m/e): 532.0 (M+H$^+$, 100%).

EXAMPLE 60

(5-Methanesulfonyl-2-morpholin-4-yl-phenyl)-[4-(5-trifluoromethyl-thiazol-2-yl)-piperazin-1-yl]-methanone

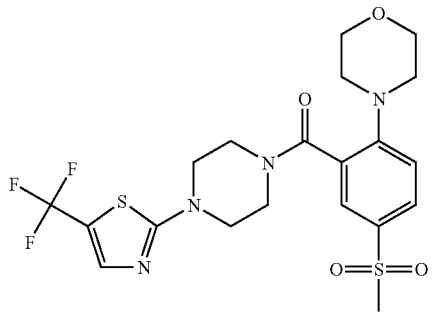

Prepared in analogy to example 1 (b) from 5-methanesulfonyl-2-morpholin-4-yl-benzoic acid (Example A13) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the title compound as an off-white crystalline solid (yield 71%). MS (m/e): 505.3 (M+H$^+$, 100%).

EXAMPLE 61

(2-Cyclopropylmethoxy-5-methanesulfonyl-phenyl)-[4-(5-trifluoromethyl-thiazol-2-yl)-piperazin-1-yl]-methanone

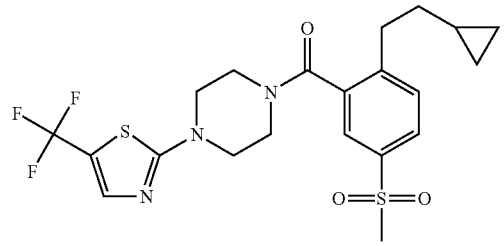

Prepared in analogy to example 1 (b) from 2-cyclopropylmethoxy-5-methanesulfonyl-benzoic acid (Example A5) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the title compound as a white crystalline solid (yield 22%). MS (m/e): 490.3 (M+H$^+$, 100%).

EXAMPLE 62

(2-Isopropoxy-5-methanesulfonyl-phenyl)-[4-(5-trifluoromethyl-[1,3,4]thiadiazol-2-yl)-piperazin-1-yl]-methanone a) 4-(5-Trifluoromethyl-[1,3,4]thiadiazol-2-yl)-piperazine-1-carboxylic acid tert-butyl ester A mixture of 2.2 mmol 2-bromo-5-trifluoromethyl-[1,3,4]thiadiazole (CA 37461-6-3; prepared according to DE2533605), 2.3 mmol piperazine-1-carboxylic acid tert-butyl ester and 4.3 mmol potassium carbonate in 10 ml acetonitrile was refluxed for 4 hours. The reaction mixture was cooled, poured into water and extracted 3 times with ethyl acetate. Concentration and recrystallisation of the crude material from diethyl ether yielded the title compound as a colorless solid. MS (m/e): 397.2 ([M+CH$_3$COO]$^{31}$, 100%).

b) 1-(5-Trifluoromethyl-[1,3,4]thiadiazol-2-yl)-piperazine trifluoroacetate 0.83 mmol 4-(5-trifluoromethyl-[1,3,4]thiadiazol-2-yl)-piperazine-1-carboxylic acid tert-butyl ester in 10 ml of dichloromethane was treated with 6.6 mmol trifluoroacetic acid and stirred for 2 hours at room temperature. The reaction mixture is concentrated to give the title compound as yellowish gum. MS (m/e): 239.1 (M+H$^+$, 100%).

c) (2-Isopropoxy-5-methanesulfonyl-phenyl)-[4-(5-trifluoromethyl-[1,3,4]thiadiazol-2-yl)-piperazin-1-yl]-methanone

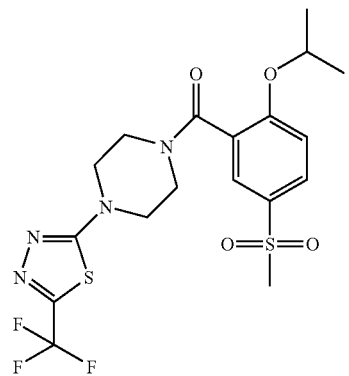

Prepared in analogy to example 1 (b) from 2-isopropoxy-5-methanesulfonyl-benzoic acid (Example A1) and 1-(5-trifluoromethyl-[1,3,4]thiadiazol-2-yl)-piperazine trifluoroacetate. The crude material was purified by chromatography (SiO2, dichloromethane/methanol 99:1) to yield the title compound as a colorless solid. MS (m/e): 479.2 (M+H$^+$, 100%).

EXAMPLE 63

(2-Cyclopropylmethoxy-5-methanesulfonyl-phenyl)-[4-(5-trifluoromethyl-[1,3,4]thiadiazol-2-yl)-piperazin-1-yl]-methanone

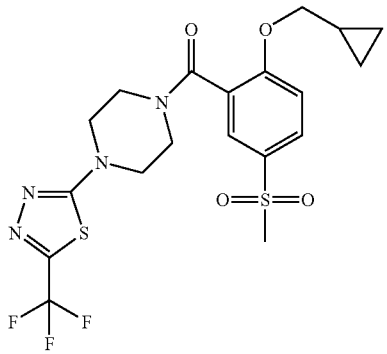

Prepared in analogy to example 1 (b) from 2-cyclopropylmethoxy-5-methanesulfonyl-benzoic acid (Example A5) and 1-(5-trifluoromethyl-[1,3,4]thiadiazol-2-yl)-piperazine trifluoroacetate (Example 62(b)). The crude material was purified by chromatography (SiO2, dichloromethane/methanol 98:2) to yield the title compound as a colorless solid. MS (m/e): 491.2 (M+H+, 100%).

EXAMPLE 64

(2-Isobutoxy-5-methanesulfonyl-phenyl)-[4-(5-trifluoromethyl-[1,3,4]thiadiazol-2-yl)-piperazin-1-yl]-methanone

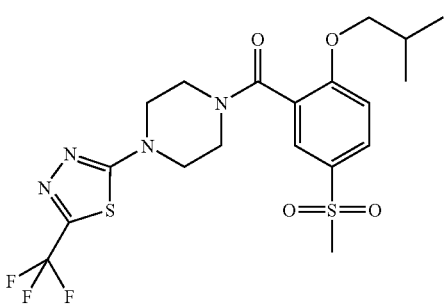

Prepared in analogy to example 1 (b) from 2-isobutoxy-5-methanesulfonyl-benzoic acid (Example A8) and 1-(5-trifluoromethyl-[1,3,4]thiadiazol-2-yl)-piperazine trifluoroacetate (Example 62(b)). The crude material was purified by chromatography (SiO2, dichloromethane/methanol 98:2) to yield the title compound as a colorless solid. MS (m/e): 493.4 (M+H$^+$, 100%).

EXAMPLE 65

(5-Methanesulfonyl-2-morpholin-4-yl-phenyl)-[4-(5-trifluoromethyl-[1,3,4]thiadiazol-2-yl)-piperazin-1-yl]-methanone

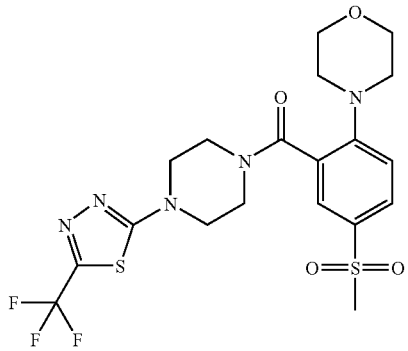

Prepared in analogy to example 1 (b) from 5-methanesulfonyl-2-morpholin-4-yl-benzoic acid (Example A13) and 1-(5-trifluoromethyl-[1,3,4]thiadiazol-2-yl)-piperazine trifluoroacetate (Example 62(b)). The crude material was purified by chromatography (SiO2, dichloromethane/methanol 99:1) to yield the title compound as a colorless solid. MS (m/e): 506.3 (M+H$^+$, 100%).

EXAMPLE 66

[5-Methanesulfonyl-2-(2,2,2-trifluoro-1,1-dimethyl-ethoxy)-phenyl]-[4-(5-trifluoromethyl-thiazol-2-yl)-piperazin-1-yl]-methanone

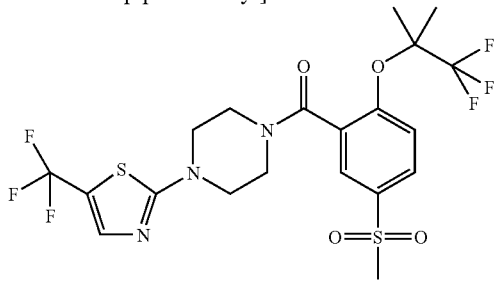

Prepared in analogy to example 1 (b) from 5-methanesulfonyl-2-(2,2,2-trifluoro-1,1-dimethyl-ethoxy)-benzoic acid (Example A14) and 1-(5-trifluoromethyl-thiazol-2-yl)-piperazine hydrochloride (Example 58(c)). The crude material was purified by chromatography (ethyl acetate/heptane) to yield the title compound as a white solid (yield 52%). MS (m/e): 546.3 (M+H$^+$, 100%). B.p.=182–183° C.

EXAMPLE 67

[5-Methanesulfonyl-2-((S)-2,2,2-trifluoro-1-methyl-ethoxy)-phenyl]-[4-(5-trifluoromethyl-thiazol-2-yl)-piperazin-1-yl]-methanone

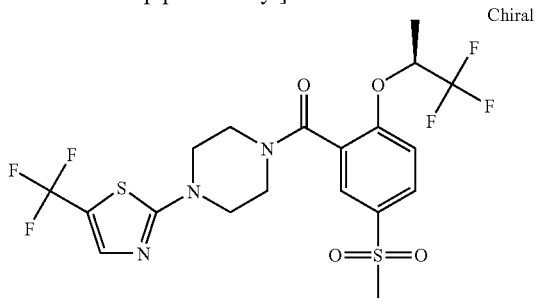

Prepared in analogy to example 1 (b) from 5-methanesulfonyl-2-((S)-2,2,2-trifluoro-1-methyl-ethoxy)-benzoic acid (Example A15) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the title compound as an off-white crystalline solid (yield 52%). MS (m/e): 532.3 (M+H$^+$, 100%).

EXAMPLE 68

[5-Methanesulfonyl-2-((R)-2,2,2-trifluoro-1-methyl-ethoxy)-phenyl]-[4-(5-trifluoromethyl-thiazol-2-yl)-piperazin-1-yl]-methanone

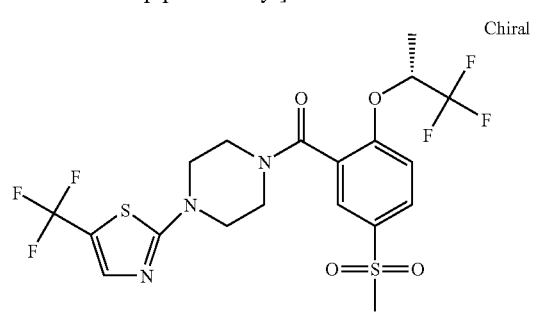

Prepared in analogy to example 1 (b) from 5-methanesulfonyl-2-((R)-2,2,2-trifluoro-1-methyl-ethoxy)-benzoic acid (Example A16) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the title compound as an off-white crystalline solid (yield 57%). MS (m/e): 532.0 (M+H$^+$, 100%).

EXAMPLE 69

[5-Methanesulfonyl-2-(2,2,2-trifluoro-1-methyl-ethoxy)-phenyl]-{4-[5-(2,2,2-trifluoro-ethyl)-thiazol-2-yl]-piperazin-1-yl}-methanone a) 4-(5-Hydroxymethyl-thiazol-2-yl)-piperazine-1-carboxylic acid tert-butyl ester To a solution of 179 mmol 30% aqueous hydrogen peroxide in 60 ml water was added 1 N aqueous sodium hydroxide solution until the pH was 9. The reaction mixture was then cooled to 10° C. and 163 mmol acrolein was added dropwise. Further amounts of 1 N aqueous sodium hydroxide solution were added during the addition in order to maintain the pH of the reaction mixture between pH 8 and 9. The mixture was stirred for 30 min at 0° C. and then 40.8 mmol thiocarbamoyl-piperazine-1-carboxylic acid tert-butyl ester (prepared from tert-butyl 1-piperazinecarboxylate, 1,1'-thiocarbonyldiimidazole and ammonia according to the procedure of J. Med. Chem. 1998, 41, 5037–5054) was added. To the resulting suspension was added 25 ml ethanol and the mixture was heated at 80° C. for 30 min. The resulting solution was diluted with ethyl acetate/tetrahydrofuran (1:1) and the mixture was washed twice with brine. The organic phase was dried over sodium sulphate and concentrated in vacuo to afford the title compound as a yellow oil (yield 99%). MS (m/e): 300.3 (M+H$^+$, 100%).

b) 4-(5-Formyl-thiazol-2-yl)-piperazine-1-carboxylic acid tert-butyl ester

To a solution of 40.0 mmol 4-(5-hydroxymethyl-thiazol-2-yl)-piperazine-1-carboxylic acid tert-butyl ester in 300 ml dichloromethane was added 289 mmol manganese(IV) oxide and the mixture was heated at reflux for 3 h. The mixture was then filtered and the filtrate was concentrated in vacuo. The residue was purified by chromatography (SiO$_2$, ethyl acetate/heptane) to afford the title compound as a light brown crystalline solid (yield 40%). MS (m/e): 298.3 (M+H$^+$, 100%).

c) 4-[5-(2,2-Difluoro-vinyl)-thiazol-2-yl]-piperazine-1-carboxylic acid tert-butyl ester To a solution of 6.73 mmol triphenylphosphine in 13 ml N,N-dimethylformamide was added 6.73 mmol dibromodifluoromethane and the mixture was stirred at room temperature for 1 h. 3.36 mmol 4-(5-formyl-thiazol-2-yl)-piperazine-1-carboxylic acid tert-butyl ester was added and the mixture was then cooled to 0° C. 6.73 mmol zinc dust was added in small portions and stirring continued for 10 min at 0° C. The mixture was then allowed to warm to room temperature and stirring continued for a further 2 h. The reaction mixture was then filtered and the filtrate was concentrated in vacuo. The residue was purified by chromatography (SiO$_2$, ethyl acetate/heptane) to afford the title compound as a white crystalline solid (yield 19%). MS (m/e): 332.3 (M+H$^+$, 10%), 276.0 ([M+2H−$^t$Bu]$^+$, 100%).

d) 4-[5-(2,2,2-Trifluoro-ethyl)-thiazol-2-yl]-piperazine-1-carboxylic acid tert-butyl ester To a solution of 1.03 mmol 4-[5-(2,2-difluoro-vinyl)-thiazol-2-yl]-piperazine-1-carboxylic acid tert-butyl ester in 7.5 dimethylsulphoxide and 0.3 ml water was added 7.18 mmol potassium fluoride and the mixture was heated at 120° C. for 2 h. The mixture was then diluted with ethyl acetate and washed sequentially with water and brine. The organic phase was dried over sodium sulphate and concentrated in vacuo. The residue was purified by chromatography (SiO$_2$, ethyl acetate/heptane) to afford the title compound as a yellow crystalline solid (yield 90%). MS (m/e): 352.3 (M+H$^+$, 100%).

e) 1-[5-(2,2,2-Trifluoro-ethyl)-thiazol-2-yl]-piperazine hydrochloride

To a solution of 0.91 mmol 4-[5-(2,2,2-trifluoro-ethyl)-thiazol-2-yl]-piperazine-1-carboxylic acid tert-butyl ester in 30 ml dioxane was added dropwise 18.2 mmol hydrogen chloride solution (4 M in dioxane) and the mixture was stirred at 90° C. for 90 min. The reaction mixture was then cooled to 0° C. and diluted with ether. The resulting crystals were collected by filtration and washed with ether to afford the title compound as a light brown crystalline solid (yield 73%). MS (m/e): 252.3 (M+H+, 100%).

f) [5-Methanesulfonyl-2-(2,2,2-trifluoro-1-methyl-ethoxy)-phenyl]-{4-[5-(2,2,2-trifluoro-ethyl)-thiazol-2-yl]-piperazin-1-yl}-methanone

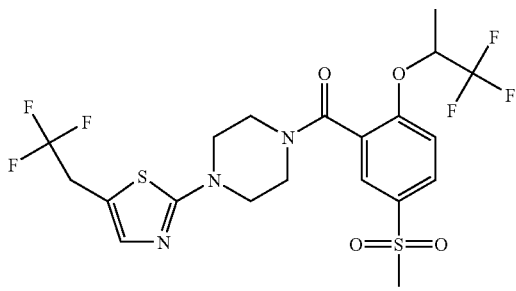

Prepared in analogy to example 1 (b) from 5-methanesulfonyl-2-(2,2,2-trifluoro-1-methyl-ethoxy)-benzoic acid (Example A2) and 1-[5-(2,2,2-trifluoro-ethyl)-thiazol-2-yl]-piperazine hydrochloride. The crude material was purified by chromatography (SiO$_2$, methanol/dichloromethane) to yield the title compound as a white crystalline solid (yield 32%). MS (m/e): 546.3 (M+H$^+$, 100%).

EXAMPLE 70

[5-Methanesulfonyl-2-((S)-2,2,2-trifluoro-1-methyl-ethoxy)-phenyl]-{4-[5-(2,2,2-trifluoro-ethyl)-thiazol-2-yl]-piperazin-1-yl}-methanone

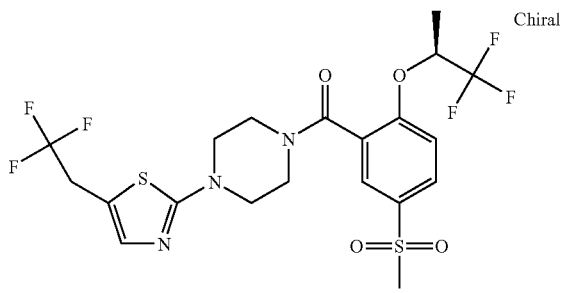

Prepared in analogy to example 1 (b) from 5-methanesulfonyl-2-((S)-2,2,2-trifluoro-1-methyl-ethoxy)-benzoic acid (Example A15) and 1-[5-(2,2,2-trifluoro-ethyl)-thiazol-2-yl]-piperazine hydrochloride (Example 69(e)). The crude material was purified by chromatography (SiO$_2$, methanol/dichloromethane) to yield the title compound as a white crystalline solid (yield 54%). MS (m/e): 546.3 (M+H$^+$, 100%).

EXAMPLE 71

[5-Methanesulfonyl-2-((R)-2,2,2-trifluoro-1-methyl-ethoxy)-phenyl]-{4-[5-(2,2,2-trifluoro-ethyl)-thiazol-2-yl]-piperazin-1-yl}-methanone

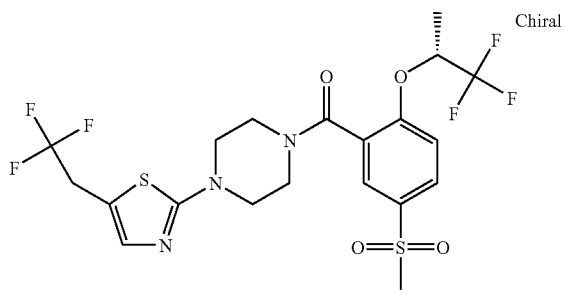

Prepared in analogy to example 1 (b) from 5-methanesulfonyl-2-((R)-2,2,2-trifluoro-1-methyl-ethoxy)-benzoic acid (Example A16) and 1-[5-(2,2,2-trifluoro-ethyl)-thiazol-2-yl]-piperazine hydrochloride (Example 69(e)). The crude material was purified by chromatography (SiO$_2$, methanol/dichloromethane) to yield the title compound as a white crystalline solid (yield 41%). MS (m/e): 546.3 (M+H$^+$, 100%).

EXAMPLE 72

(2-Isopropoxy-5-methanesulfonyl-phenyl)-{4-[5-(2,2,2-trifluoro-ethyl)-thiazol-2-yl]-piperazin-1-yl}-methanone

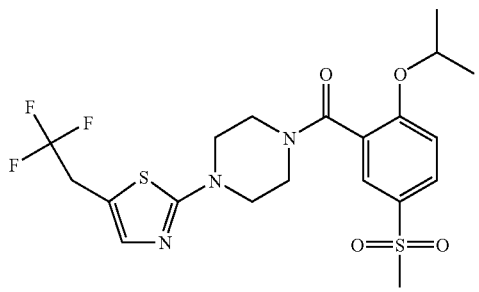

Prepared in analogy to example 1 (b) from 2-isopropoxy-5-methanesulfonyl-benzoic acid (Example A1) and 1-[5-(2,2,2-trifluoro-ethyl)-thiazol-2-yl]-piperazine hydrochloride (Example 69(e)). The crude material was purified by chromatography (SiO$_2$, ethyl acetate/heptane) to yield the title compound as a white crystalline solid (yield 36%). MS (m/e): 492.4 (M+H$^+$, 100%).

EXAMPLE 73

[5-Methanesulfonyl-2-(2,2,2-trifluoro-1,1-dimethyl-ethoxy)-phenyl]-{4-[5-(2,2,2-trifluoro-ethyl)-thiazol-2-yl]-piperazin-1-yl}-methanone

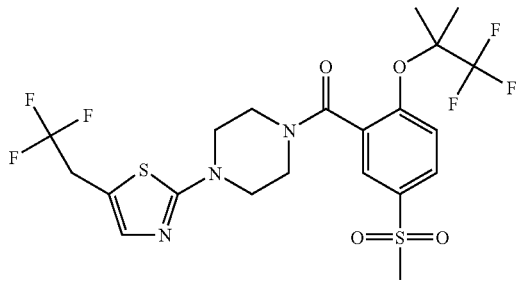

Prepared in analogy to example 1 (b) from 5-methanesulfonyl-2-(2,2,2-trifluoro-1,1-dimethyl-ethoxy)-benzoic

EXAMPLE 74

[5-Ethanesulfonyl-2-(2,2,2-trifluoro-1-methyl-ethoxy)-phenyl]-[4-(5-trifluoromethyl-thiazol-2-yl)-piperazin-1-yl]-methanone

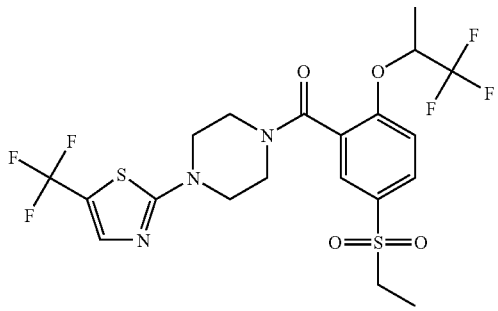

Prepared in analogy to example 1 (b) from 5-ethanesulfonyl-2-(2,2,2-trifluoro-1-methyl-ethoxy)-benzoic acid (Example A17) and 1-(5-trifluoromethyl-thiazol-2-yl)-piperazine hydrochloride (Example 58(c)). The crude material was purified by reversed phase HPLC (acetonitrile/water) followed by trituration in ether to yield the title compound as an off-white crystalline solid (yield 82%). MS (m/e): 546.4 (M+H+, 100%).

EXAMPLE 75

(5-Ethanesulfonyl-2-isopropoxy-phenyl)-[4-(5-trifluoromethyl-thiazol-2-yl)-piperazin-1-yl]-methanone

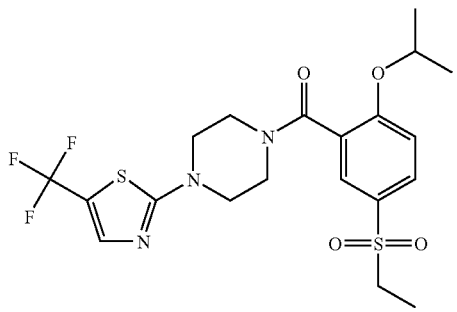

Prepared in analogy to example 1 (b) from 5-ethanesulfonyl-2-isopropoxy-benzoic acid (Example A18) and 1-(5-trifluoromethyl-thiazol-2-yl)-piperazine hydrochloride (Example 58(c)). The crude material was purified by reversed phase HPLC (acetonitrile/water) followed by trituration in ether to yield the title compound as an off-white crystalline solid (yield 21%). MS (m/e): 492.1 (M+H+, 100%).

EXAMPLE 76

[5-Methanesulfonyl-2-(1-trifluoromethyl-propoxy)-phenyl]-[4-(5-trifluoromethyl-thiazol-2-yl)-piperazin-1-yl]-methanone

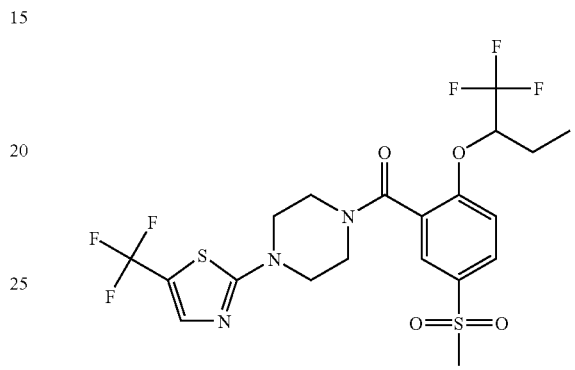

Prepared in analogy to example 1 (b) from 5-methanesulfonyl-2-(1-trifluoromethyl-propoxy)-benzoic acid (Example A19) and 1-(5-trifluoromethyl-thiazol-2-yl)-piperazine hydrochloride (Example 58(c)). The crude material was purified by reversed phase HPLC (acetonitrile/water) followed by trituration in ether to yield the title compound as an off-white crystalline solid (yield 11%). MS (m/e): 546.3 (M+H+, 100%).

EXAMPLE 77

(2-((R)-sec-Butoxy)-5-methanesulfonyl-phenyl)-[4-(5-trifluoromethyl-thiazol-2-yl)-piperazin-1-yl]-methanone

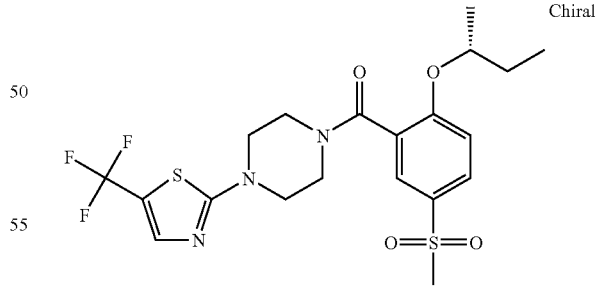

Prepared in analogy to example 1 (b) from 2-((R)-sec-butoxy)-5-methanesulfonyl-benzoic acid (Example A20) and 1-(5-trifluoromethyl-thiazol-2-yl)-piperazine hydrochloride (Example 58(c)). The crude material was purified by reversed phase HPLC (acetonitrile/water) followed by trituration in ether to yield the title compound as an off-white crystalline solid (yield 10%). MS (m/e): 492.4 (M+H+, 100%).

EXAMPLE 78

(2-((S)-sec-Butoxy)-5-methanesulfonyl-phenyl)-[4-(5-trifluoromethyl-thiazol-2-yl)-piperazin-1-yl]-methanone

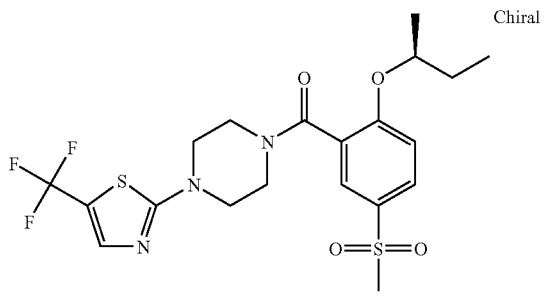

Prepared in analogy to example 1 (b) from 2-((S)-sec-butoxy)-5-methanesulfonyl-benzoic acid (Example A21) and 1-(5-trifluoromethyl-thiazol-2-yl)-piperazine hydrochloride (Example 58(c)). The crude material was purified by reversed phase HPLC (acetonitrile/water) followed by trituration in ether to yield the title compound as an off-white crystalline solid (yield 13%). MS (m/e): 492.4 (M+H$^+$, 100%).

EXAMPLE 79

(2-Isopropoxy-5-methanesulfonyl-phenyl)-[4-(4-methyl-5-trifluoromethyl-thiazol-2-yl)-piperazin-1-yl]-methanone a) Rac-(3,3,3-Trifluoro-1-methyl-propylsulfanyl)-benzene To a solution of 54.9 mmol 3-iodo-1,1,1-trifluorobutane in 50 ml N,N-dimethylformamide were added 49.9 mmol thiophenol and 74.9 mmol potassium carbonate. The mixture was ultrasonicated at room temperature for 90 min. The reaction mixture was then diluted with ether and was washed three times with water. The organic phase was dried over sodium sulfate and concentrated in vacuo to afford the title compound as a colourless oil (yield 79%). MS (m/e): 221.3 (M$^+$, 15%).

b) Rac-(4,4,4-Trifluoro-butane-2-sulfonyl)-benzene

To a solution of 39.5 mmol rac-(3,3,3-trifluoro-1-methyl-propylsulfanyl)-benzene in 80 ml dichloromethane was added 178 mmol trifluoroacetic acid. 148 mmol urea hydrogen peroxide was then added in small portions and the mixture was subsequently heated at reflux for 4 h. The reaction mixture was then diluted with dichloromethane and was washed sequentially with water, 1 N aqueous sodium hydroxide, and again with water. The organic phase was then dried over sodium sulfate and concentrated in vacuo to afford the title compound as a colourless oil (yield 80%). EI-MS (m/e): 252.1 (M$^+$, 3%), 142.1 (PhSO$_2$H$^+$, 100%), 91.1 (H$_3$CCH=CHCF$_3^+$, 20%; 78.2 (PhH$^+$, 74%), 77.2 (Ph$^+$, 45%).

c) Rac-(4,4,4-Trifluoro-2-iodo-butane-2-sulfonyl)-benzene

To a solution of 28.5 mmol diisopropylamine in 18 ml tetrahydrofuran at −78° C. was added dropwise 28.5 mmol n-butyllithium solution (1.6 M in hexane) and the mixture was then warmed to room temperature. The resulting solution was then added dropwise over 50 min to a solution of 19.0 mmol rac-(4,4,4-trifluoro-butane-2-sulfonyl)-benzene in 30 ml tetrahydrofuran at −78° C. and stirring continued for a further 15 min at −78° C. Finally, a solution of 20.9 mol iodine in 15 ml tetrahydrofuran was added dropwise over 15 min and stirring continued for a further 15 min at −78° C. and then the reaction mixture was allowed to warm to −20° C. The reaction mixture was quenched by addition of 1 M hydrochloric acid and the mixture was extracted three times with ethyl acetate. The combined organic phases were washed sequentially with aqueous sodium thiosulfite solution and with brine and then dried over sodium sulphate and concentrated in vacuo to afford the title compound as a yellow oil (yield 87%). EI-MS (m/e): 377.9 (M$^+$, 4%), 237.0 ([M−PhSO$_2$]$^+$, 40%), 142.0 (PhSO$_2$H$^+$, 100%), 125.1 (PhSO$^+$, 93%), 78.2 (PhH$^+$, 40%), 77.2 (Ph$^+$, 31%).

d) ((E)-4,4,4-Trifluoro-but-2-ene-2-sulfonyl)-benzene

To a solution of 14.0 mmol rac-(4,4,4-trifluoro-2-iodo-butane-2-sulfonyl)-benzene in 25 ml tetrahydrofuran and 2.5 ml water were added 42.1 mmol triethylamine and 42.1 mmol potassium carbonate. The mixture was heated at 70° C. for 6 h. The reaction mixture was then diluted with ethyl acetate and was washed sequentially with 1 N hydrochloric acid and brine. The organic phase was dried over sodium sulfate and concentrated in vacuo. The residue was purified by chromatography (SiO$_2$, ethyl acetate/heptane) to afford the title compound as a yellow oil (yield 72%). EI-MS (m/e): 250.1 (M$^+$, 15%), 186.1 ([M−SO$_2$]$^+$, 38%), 125.0 (PhSO$^+$, 100%), 77.1 (Ph$^+$, 38%).

e) Rac-2-Benzenesulfonyl-2-methyl-3-trifluoromethyl-oxirane

To a solution of 15.2 mmol n-butyllithium solution (1.6 M in hexane) in 20 ml tetrahydrofuran at −78° C. was added dropwise 15.2 mmol tert-butyl hydroperoxide solution (5.5 M in nonane) and the mixture was stirred at −78° C. for 10 min, then warmed to −50° C. and re-cooled to −78° C. A solution of 10.1 mmol ((E)-4,4,4-trifluoro-but-2-ene-2-sulfonyl)-benzene in 6 ml tetrahydrofuran was then added dropwise and stirring continued for a further 30 min at −78° C. and then the reaction mixture was allowed to warm to room temperature. The reaction mixture was diluted with ethyl acetate and washed sequentially with 1 M hydrochloric acid and with brine. The organic phase was then dried over sodium sulphate and concentrated in vacuo. The residue was purified by chromatography (SiO$_2$, ethyl acetate/heptane) to afford the title compound as a colourless oil (yield 49%). EI-MS (m/e): 251.1 ([M−CH$_3$]$^+$, 6%), 250.1 ([M−O]$^+$, 20%), 126.1 (PhSOH$^+$, 61%), 125.0 ([M−PhSO$_2$]$^+$, 100%), 78.2 (PhH$^+$, 21%), 77.2 (Ph$^+$, 44%), 43.3 (CH$_3$CHCH$_3^+$, 73%).

f) 4-(4-Methyl-5-trifluoromethyl-thiazol-2-yl)-piperazine-1-carboxylic acid tert-butyl ester A mixture of 4.92 mmol rac-2-benzenesulfonyl-2-methyl-3-trifluoromethyl-oxirane and 5.41 mmol 4-thiocarbamoyl-piperazine-1-carboxylic acid tert-butyl ester (prepared from tert-butyl 1-piperazinecarboxylate, 1,1'-thiocarbonyldiimidazole and ammonia according to the procedure of J. Med. Chem. 1998, 41, 5037–5054) in 15 ml N,N-dimethylformamide was heated at 100° C. for 4.5 h. The reaction mixture was then concentrated in vacuo and the residue purified by chromatography (SiO$_2$, ethyl acetate/heptane) to afford the title compound as a yellow crystalline solid (yield 30%). MS (m/e): 352.3 (M+H$^+$, 100%).

g) 1-(4-Methyl-5-trifluoromethyl-thiazol-2-yl)-piperazine hydrochloride

To a solution of 1.45 mmol 4-(4-methyl-5-trifluoromethyl-thiazol-2-yl)-piperazine-1-carboxylic acid tert-butyl ester in 10 ml dioxane was added dropwise 21.8 mmol hydrogen chloride solution (4 M in dioxane) and the mixture was stirred at 90° C. for 2 h. The reaction mixture was then cooled to 0° C. and diluted with ether. The resulting crystals were collected by filtration and washed with ether to afford the title compound as a white crystalline solid (yield 68%). MS (m/e): 252.3 (M+H+, 100%).

h) (2-Isopropoxy-5-methanesulfonyl-phenyl)-[4-(4-methyl-5-trifluoromethyl-thiazol-2-yl)-piperazin-1-yl]-methanone

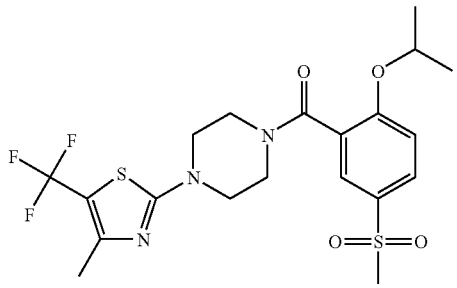

Prepared in analogy to example 1 (b) from 2-isopropoxy-5-methanesulfonyl-benzoic acid (Example A1) and 1-(4-methyl-5-trifluoromethyl-thiazol-2-yl)-piperazine hydrochloride. The crude material was purified by chromatography (SiO$_2$, ethyl acetate/heptane) to yield the title compound as a white foam (yield 52%). MS (m/e): 492.0 (M+H$^+$, 100%).

EXAMPLE 80

[5-Methanesulfonyl-2-((S)-2,2,2-trifluoro-1-methyl-ethoxy)-phenyl]-[4-(4-methyl-5-trifluoromethyl-thiazol-2-yl)-piperazin-1-yl]-methanone

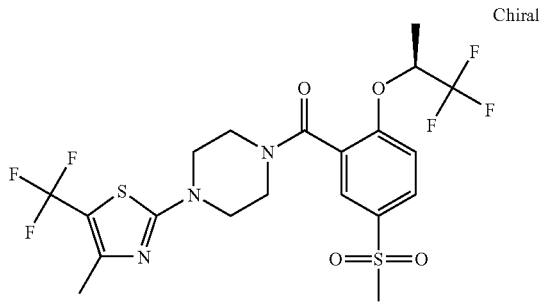

Prepared in analogy to example 1 (b) from 5-methanesulfonyl-2-((S)-2,2,2-trifluoro-1-methyl-ethoxy)-benzoic acid (Example A15) and 1-(4-methyl-5-trifluoromethyl-thiazol-2-yl)-piperazine hydrochloride (Example 79(g)). The crude material was purified by chromatography (SiO$_2$, ethyl acetate/heptane) to yield the title compound as a white crystalline solid (yield 56%). MS (m/e): 546.0 (M+H$^+$, 100%).

EXAMPLE 81

[5-Methanesulfonyl-2-((R)-2,2,2-trifluoro-1-methyl-ethoxy)-phenyl]-[4-(4-methyl-5-trifluoromethyl-thiazol-2-yl)-piperazin-1-yl]-methanone

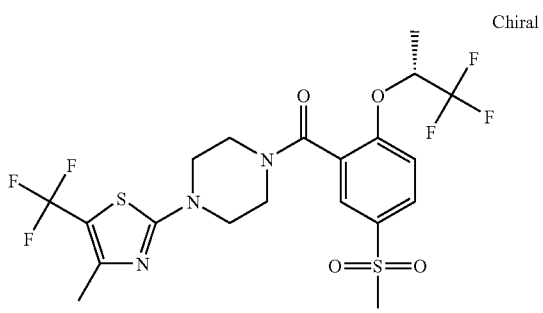

Prepared in analogy to example 1 (b) from 5-methanesulfonyl-2-((R)-2,2,2-trifluoro-1-methyl-ethoxy)-benzoic acid (Example A16) and 1-(4-methyl-5-trifluoromethyl-thiazol-2-yl)-piperazine hydrochloride (Example 79(g)). The crude material was purified by chromatography (SiO$_2$, ethyl acetate/heptane) to yield the title compound as a white crystalline solid (yield 57%). MS (m/e): 546.0 (M+H$^+$, 100%).

EXAMPLE 82

1-{2-[4-(2-Isopropoxy-5-methanesulfonyl-benzoyl)-piperazin-1-yl]-thiazol-5-yl}-propan-1-one a) 4-(Dimethylaminomethylene-thiocarbamoyl)-piperazine-1-carboxylic acid tert-butyl ester A mixture of 122 mmol N,N-dimethylformamide dimethyl acetal and 6.11 mmol 4-thiocarbamoyl-piperazine-1-carboxylic acid tert-butyl ester (prepared from tert-butyl 1-piperazinecarboxylate, 1,1'-thiocarbonyldiimidazole and ammonia according to the procedure of J. Med. Chem. 1998, 41, 5037–5054) was heated at 110° C. for 3 h. The reaction mixture was then concentrated in vacuo and the residue was resuspended in ethyl acetate/tetrahydrofuran (1:1) and washed with brine. The organic phase was dried over sodium sulphate and concentrated in vacuo to afford the title compound as a light yellow crystalline solid (yield 95%). MS (m/e): 301.4 (M+H$^+$, 100%).

b) 4-(5-Propionyl-thiazol-2-yl)-piperazine-1-carboxylic acid tert-butyl ester To a solution of 0.83 mmol 4-(dimethylaminomethylene-thiocarbamoyl)-piperazine-1-carboxylic acid tert-butyl ester in 6 ml ethanol were added 2.50 mmol triethylamine and 1.00 mmol 1-bromo-2-butanone. The mixture was heated at 90° C. for 16 h. The reaction mixture was then concentrated in vacuo and the residue was purified by chromatography (SiO$_2$, ethyl acetate/heptane) to afford the title compound as a white crystalline solid (yield 72%). MS (m/e): 326.1 (M+H$^+$, 100%).

c) 1-(2-piperazin-1-yl-thiazol-5-yl)-propan-1-one hydrochloride

To a solution of 0.58 mmol 4-(5-propionyl-thiazol-2-yl)-piperazine-1-carboxylic acid tert-butyl ester in 6 ml dioxane was added dropwise 8.76 mmol hydrogen chloride solution (4 M in dioxane) and the mixture was stirred at 90° C. for 90 min. The reaction mixture was then cooled to 0° C. and diluted with ether. The resulting crystals were collected by filtration and washed with ether to afford the title compound as a white crystalline solid (yield 99%). MS (m/e): 226.4 (M+H$^+$, 100%).

d) 1-{2-[4-(2-Isopropoxy-5-methanesulfonyl-benzoyl)-piperazin-1-yl]-thiazol-5-yl}-propan-1-one

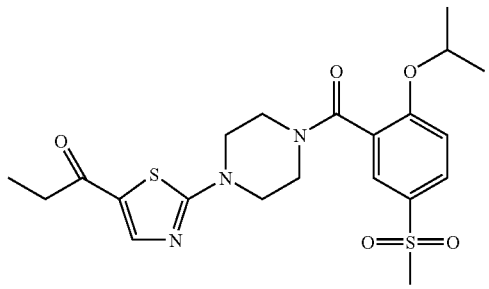

Prepared in analogy to example 1 (b) from 2-isopropoxy-5-methanesulfonyl-benzoic acid (Example A1) and 1-(2-piperazin-1-yl-thiazol-5-yl)-propan-1-one hydrochloride. The crude material was purified by chromatography (SiO$_2$, methanol/dichloromethane) to yield the title compound as a light brown crystalline solid (yield 24%). MS (m/e): 466.0 (M+H$^+$, 100%).

EXAMPLE 83

1-{2-[4-(2-Isopropoxy-5-methanesulfonyl-benzoyl)-piperazin-1-yl]-thiazol-5-yl}-2,2-dimethyl-propan-1-one a) 4-[5-(2,2-Dimethyl-propionyl)-thiazol-2-yl]-piperazine-1-carboxylic acid tert-butyl ester Prepared in analogy to example 82 (b) from 4-(dimethylaminomethylene-thiocarbamoyl)-piperazine-1-carboxylic acid tert-butyl ester (Example 82(a)) and 1-bromo-pinacolone. The crude material was purified by chromatography (SiO$_2$, ethyl acetate/heptane) to afford the title compound as a white crystalline solid (yield 87%). MS (m/e): 354.3 (M+H$^+$, 100%).

b) 2,2-Dimethyl-1-(2-piperazin-1-yl-thiazol-5-yl)-propan-1-one hydrochloride

Prepared in analogy to example 82 (c) from 4-[5-(2,2-dimethyl-propionyl)-thiazol-2-yl]-piperazine-1-carboxylic acid tert-butyl. The crude material was purified by recrystallisation from ether to afford the title compound as a white crystalline solid (yield 93%). MS (m/e): 254.4 (M+H$^+$, 100%).

c) 1-{2-[4-(2-Isopropoxy-5-methanesulfonyl-benzoyl)-piperazin-1-yl]-thiazol-5-yl}-2,2-dimethyl-propan-1-one

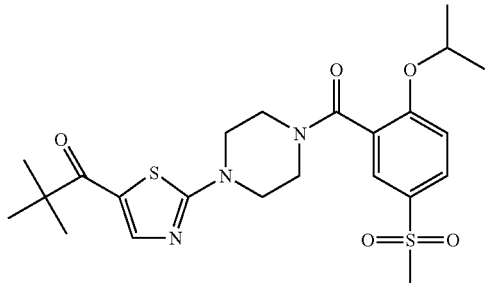

Prepared in analogy to example 1 (b) from 2-isopropoxy-5-methanesulfonyl-benzoic acid (Example A1) and 2,2-dimethyl-1-(2-piperazin-1-yl-thiazol-5-yl)-propan-1-one hydrochloride. The crude material was purified by chromatography (SiO$_2$, methanol/dichloromethane) to yield the title compound as a light brown crystalline solid (yield 28%). MS (m/e): 494.1 (M+H+, 100%).

EXAMPLE 84

(2-Isopropylsulfanyl-5-methanesulfonyl-phenyl)-[4-(5-trifluoromethyl-thiazol-2-yl)-piperazin-1-yl]-methanone

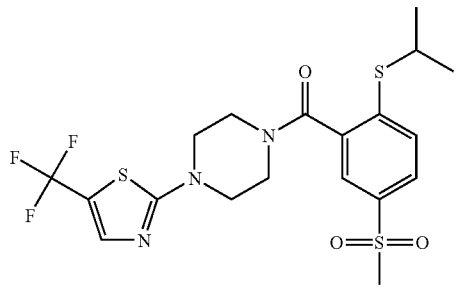

Prepared in analogy to example 1 (b) from 2-isopropyl-sulfanyl-5-methanesulfonyl-benzoic acid (Example A22) and 1-(5-trifluoromethyl-thiazol-2-yl)-piperazine hydrochloride (Example 58(c)). The crude material was purified by chromatography (SiO$_2$, ethyl acetate/heptane) followed by trituration in pentane to yield the tide compound as a white foam (yield 50%). MS (m/e): 494.4 (M+H$^+$, 100%).

EXAMPLE 85

(2-Ethylsulfanyl-5-methanesulfonyl-phenyl)-[4-(5-trifluoromethyl-thiazol-2-yl)-piperazin-1-yl]-methanone

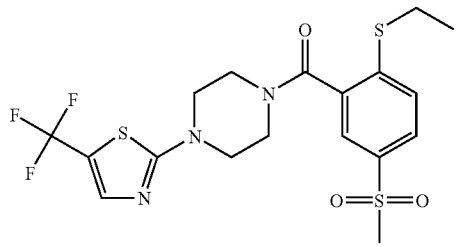

Prepared in analogy to example 1 (b) from 2-ethylsulfanyl-5-methanesulfonyl-benzoic acid (Example A23) and 1-(5-trifluoromethyl-thiazol-2-yl)-piperazine hydrochloride (Example 58(c)). The crude material was purified by chromatography (SiO$_2$, ethyl acetate/heptane) to yield the title compound as a white foam (yield 41%). MS (m/e): 479.8 (M+H$^+$, 100%).

EXAMPLE 86

[5-Methanesulfonyl-2-(2,2,2-trifluoro-ethylsulfanyl)-phenyl]-[4-(5-trifluoromethyl-thiazol-2-yl)-piperazin-1-yl]-methanone

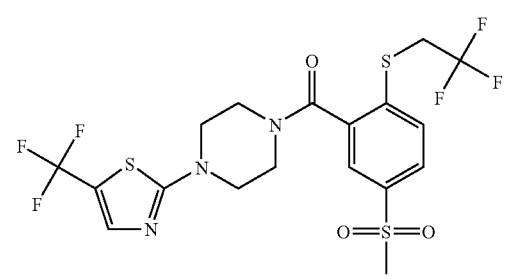

Prepared in analogy to example 1 (b) from 5-methanesulfonyl-2-(2,2,2-trifluoro-ethylsulfanyl)-benzoic acid (Example A24) and 1-(5-trifluoromethyl-thiazol-2-yl)-piperazine hydrochloride (Example 58(c)). The crude material was purified by chromatography (SiO$_2$, ethyl acetate/heptane) to yield the title compound as a light yellow solid (yield 49%). MS (m/e): 534.0 (M+H$^+$, 100%).

EXAMPLE 87

(2-Isobutylsulfanyl-5-methanesulfonyl-phenyl)-[4-(5-trifluoromethyl-thiazol-2-yl)-piperazin-1-yl]-methanone

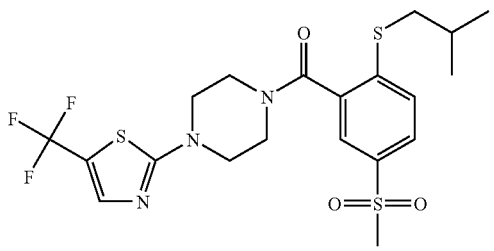

Prepared in analogy to example 1 (b) from 2-isobutylsulfanyl-5-methanesulfonyl-benzoic acid (Example A25) and 1-(5-trifluoromethyl-thiazol-2-yl)-piperazine hydrochloride (Example 58(c)). The crude material was purified by chromatography (SiO$_2$, ethyl acetate/heptane) to yield the title compound as a light yellow solid (yield 88%). MS (m/e): 508.3 (M+H$^+$, 100%).

EXAMPLE 88

(5-Methanesulfonyl-2-methylsulfanyl-phenyl)-[4-(5-trifluoromethyl-thiazol-2-yl)-piperazin-1-yl]-methanone

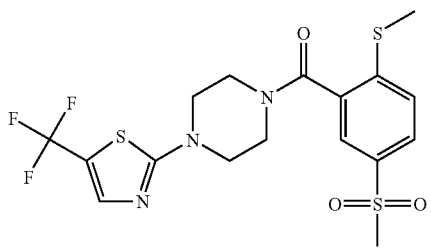

Prepared in analogy to example 1 (b) from 5-methanesulfonyl-2-methylsulfanyl-benzoic acid (Example A26) and 1-(5-trifluoromethyl-thiazol-2-yl)-piperazine hydrochloride (Example 58(c)). The crude material was purified by chromatography (SiO$_2$, ethyl acetate/heptane) to yield the title compound as a light brown solid (yield 18%). MS (m/e): 466.0 (M+H$^+$, 100%).

EXAMPLE 89

(2-Morpholin-4-yl-5-nitro-phenyl)-[4-(5-trifluoromethyl-[1,3,4]thiadiazol-2-yl)-piperazin-1-yl]-methanone

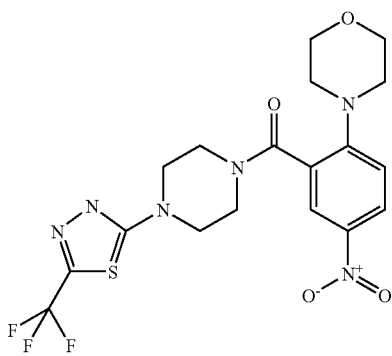

Prepared in analogy to example 1 (b) from 2-morpholin-4-yl-5-nitro-benzoic acid (Example A27) and 1-(5-trifluoromethyl-[1,3,4]thiadiazol-2-yl)-piperazine trifluoroacetate (Example 62(b)). The crude material was purified by chromatography (SiO$_2$, methanol/dichloromethane) to yield the title compound as a brown solid (yield 34%). MS (m/e): 473.4 (M+H$^+$, 100%).

EXAMPLE 90

(2-Isopropylsulfanyl-5-methanesulfonyl-phenyl)-[4-(5-trifluoromethyl-[1,3,4]thiadiazol-2-yl)-piperazin-1-yl]-methanone

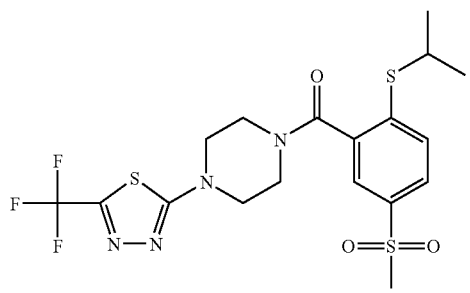

Prepared in analogy to example 1 (b) from 2-isopropylsulfanyl-5-methanesulfonyl-benzoic acid (Example A22) and 1-(5-trifluoromethyl-[1,3,4]thiadiazol-2-yl)-piperazine trifluoroacetate (Example 62(b)). The crude material was purified by chromatography (SiO$_2$, ethyl acetate/heptane) to yield the title compound as a white solid (yield 34%). MS (m/e): 495.0 (M+H$^+$, 100%).

EXAMPLE 91

(2-Isopropylsulfanyl-5-methanesulfonyl-phenyl)-[4-(3-phenyl-[1,2,4]thiadiazol-5-yl)-piperazin-1-yl]-methanone

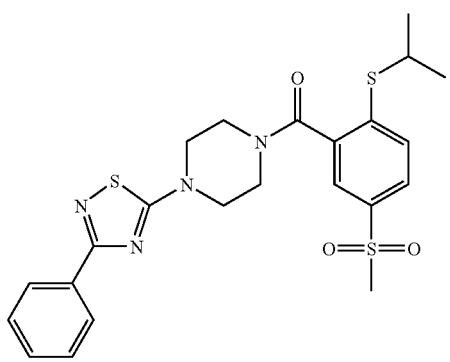

Prepared in analogy to example 1 (b) from 2-isopropylsulfanyl-5-methanesulfonyl-benzoic acid (Example A22) and 3-phenyl-5-piperazino-1,2,4-thiadiazole. The crude material was purified by chromatography (SiO$_2$, ethyl acetate/heptane) to yield the title compound as an off-white solid (yield 83%). MS (m/e): 503.1 (M+H$^+$, 100%).

EXAMPLE 92

[5-Methanesulfonyl-2-((S)-2,2,2-trifluoro-1-methyl-ethoxy)-phenyl]-[4-(3-phenyl-[1,3,4]thiadiazol-5-yl)-piperazin-1-yl]-methanone

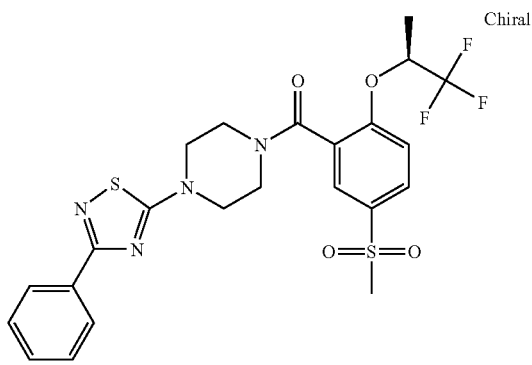

Prepared in analogy to example 1 (b) from 5-methanesulfonyl-2-((S)-2,2,2-trifluoro-1-methyl-ethoxy)-benzoic acid (Example A15) and 3-phenyl-5-piperazino-1,2,4-thiadiazole. The crude material was purified by chromatography (SiO$_2$, ethyl acetate/heptane) to yield the title compound as a light brown solid (yield 60%). MS (m/e): 541.3 (M+H$^+$, 100%).

EXAMPLE 93

[5-Methanesulfonyl-2-((S)-2,2,2-trifluoro-1-methyl-ethoxy)-phenyl]-[4-(5-trifluoromethyl-[1,3,4]thiadiazol-2-yl)-piperazin-1-yl]-methanone

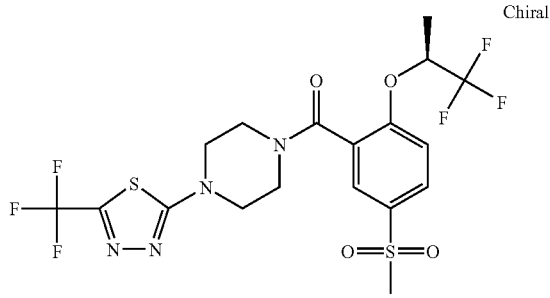

Prepared in analogy to example 1 (b) from 5-methanesulfonyl-2-((S)-2,2,2-trifluoro-1-methyl-ethoxy)-benzoic acid (Example A15) and 1-(5-trifluoromethyl-[1,3,4]thiadiazol-2-yl)-piperazine trifluoroacetate (Example 62(b)). The crude material was purified by chromatography (SiO$_2$, ethyl acetate/heptane) to yield the title compound as an off-white solid (yield 52%). MS (m/e): 533.0 (M+H$^+$, 100%).

EXAMPLE 94

4-Isopropoxy-3-[4-(3-phenyl-[1,2,4]thiadiazol-5-yl)-piperazine-1-carbonyl]-benzonitrile

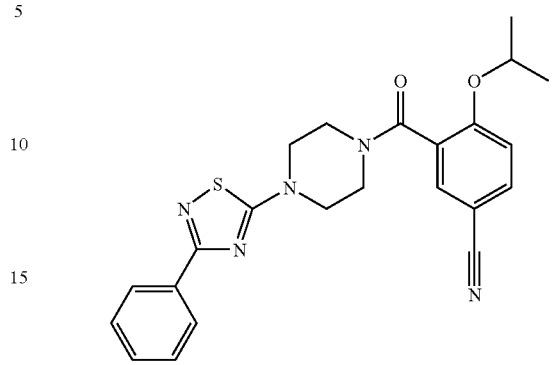

Prepared in analogy to example 1 (b) from 5-cyano-2-isopropoxy-benzoic acid (Example A28) and 3-phenyl-5-piperazino-1,2,4-thiadiazole. The crude material was purified by chromatography (SiO$_2$, ethyl acetate/heptane) to yield the title compound as a white solid (yield 74%). MS (m/e): 434.1 (M+H$^+$, 100%).

EXAMPLE 95

4-Isopropoxy-3-[4-(5-trifluoromethyl-[1,3,4]thiadiazol-2-yl)-piperazine-1-carbonyl]-benzonitrile

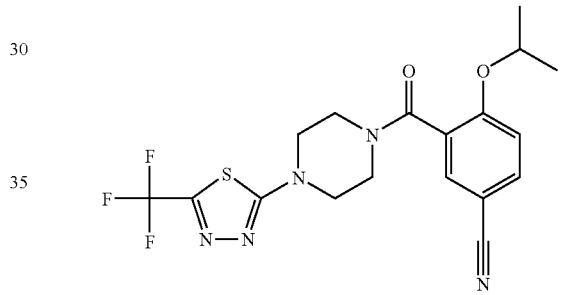

Prepared in analogy to example 1 (b) from 5-cyano-2-isopropoxy-benzoic acid (Example A28) and 1-(5-trifluoromethyl-[1,3,4]thiadiazol-2-yl)-piperazine trifluoroacetate (Example 62(b)). The crude material was purified by chromatography (SiO$_2$, ethyl acetate/heptane) to yield the title compound as a white solid (yield 80%). MS (m/e): 426.0 (M+H$^+$, 100%).

EXAMPLE 96

2-[4-(5-Cyano-2-isopropoxy-benzoyl)-piperazin-1-yl]-thiazole-5-carbonitrile

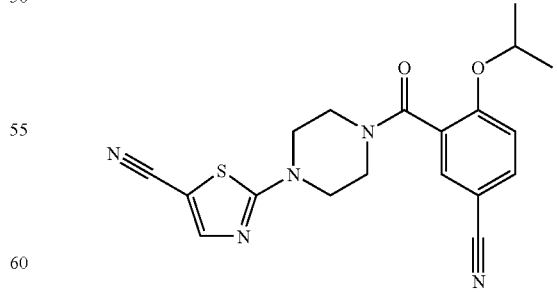

Prepared in analogy to example 1 (b) from 5-cyano-2-isopropoxy-benzoic acid (Example A28) and 2-piperazin-1-yl-thiazole-5-carbonitrile (Example 6(a)). The crude material was purified by chromatography (SiO$_2$, ethyl acetate/heptane) to yield the title compound as a white solid (yield 70%). MS (m/e): 382.3 (M+H$^+$, 100%).

EXAMPLE 97

2-[4-(2-Morpholin-4-yl-5-nitro-benzoyl)-piperazin-1-yl]-thiazole-5-carbonitrile

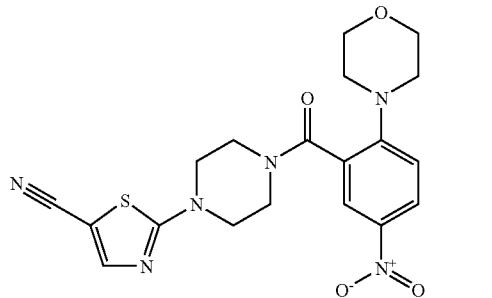

Prepared in analogy to example 1 (b) from 2-morpholin-4-yl-5-nitro-benzoic acid (Example A27) and 2-piperazin-1-yl-thiazole-5-carbonitrile (Example 6(a)). The crude material was purified by chromatography (SiO$_2$, methanol/dichloromethane) to yield the title compound as a yellow solid (yield 24%). MS (m/e): 429.5 (M+H$^+$, 100%).

EXAMPLE 98

(2-Morpholin-4-yl-5-nitro-phenyl)-[4-(3-phenyl-[1,2,4]thiadiazol-5-yl)-piperazin-1-yl]-methanone

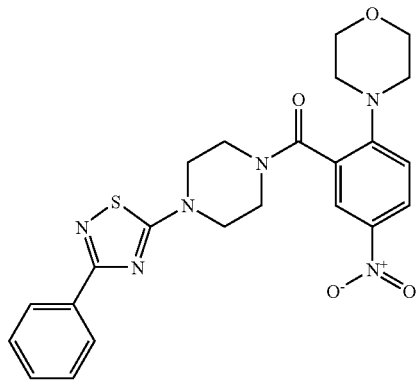

Prepared in analogy to example 1 (b) from 2-morpholin-4-yl-5-nitro-benzoic acid (Example A27) and 3-phenyl-5-piperazino-1,2,4-thiadiazole. The crude material was purified by chromatography (SiO$_2$, ethyl acetate/heptane) to yield the title compound as a yellow solid (yield 18%). MS (m/e): 481.0 (M+H$^+$, 100%).

EXAMPLE 99

3-[4-(5-Cyano-thiazol-2-yl)-piperazine-1-carbonyl]-4-cyclopentyloxy-N-methyl-benzenesulfonamide

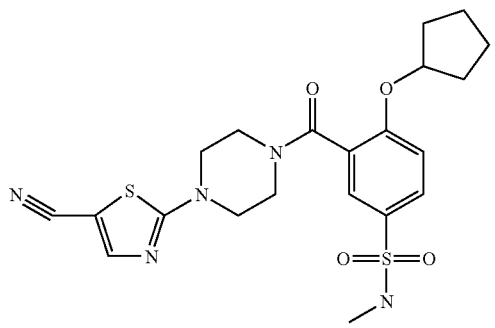

Prepared in analogy to example 1 (b) from 2-cyclopentyloxy-5-methylsulfamoyl-benzoic acid (Example A29) and 1-(5-trifluoromethyl-thiazol-2-yl)-piperazine hydrochloride (Example 58(c)). The crude material was purified by chromatography (SiO$_2$, methanol/dichloromethane) to yield the title compound as a white solid (yield 48%). MS (m/e): 476.3 (M+H$^+$, 100%).

EXAMPLE 100

4-Cyclopentyloxy-N-methyl-3-[4-(3-phenyl-[1,2,4]thiadiazol-5-yl)-piperazine-1-carbonyl]-benzenesulfonamide

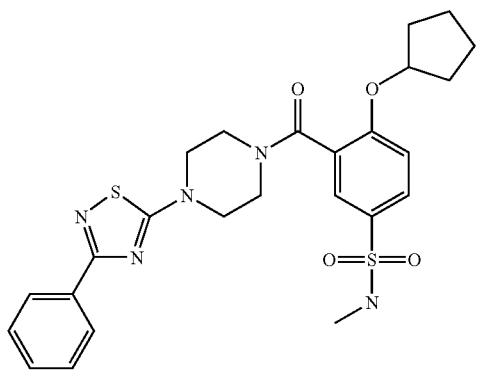

Prepared in analogy to example 1 (b) from 2-cyclopentyloxy-5-methylsulfamoyl-benzoic acid (Example A29) and 3-phenyl-5-piperazino-1,2,4-thiadiazole. The crude material was purified by chromatography (SiO$_2$, methanol/dichloromethane) to yield the title compound as an off-white solid (yield 72%). MS (m/e): 528.5 (M+H$^+$, 100%).

EXAMPLE 101

4-Cyclopentyloxy-N-methyl-3-[4-(5-trifluoromethyl-[1,3,4]thiadiazol-2-yl)-piperazine-1-carbonyl]-benzenesulfonamide

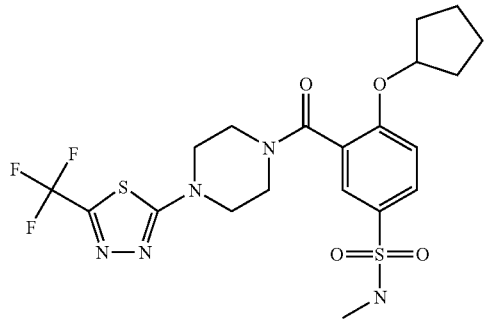

Prepared in analogy to example 1 (b) from 2-cyclopentyloxy-5-methylsulfamoyl-benzoic acid (Example A29) and 1-(5-trifluoromethyl-[1,3,4]thiadiazol-2-yl)-piperazine trifluoroacetate (Example 62(b)). The crude material was purified by chromatography (SiO$_2$, ethyl acetate/heptane) to yield the title compound as a white solid (yield 46%). MS (m/e): 520.3 (M+H$^+$, 100%).

EXAMPLE 102

[5-Methanesulfonyl-2-(2,2,3,3,3-pentafluoro-propoxy)-phenyl]-[4-(5-trifluoromethyl-[1,3,4]thiadiazol-2-yl)-piperazin-1-yl]-methanone

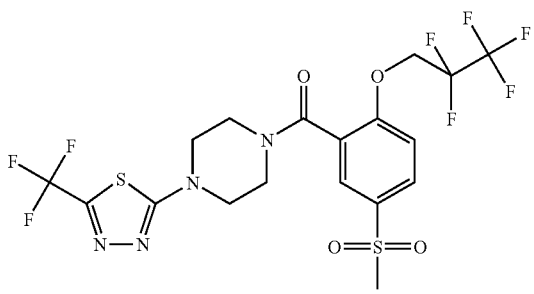

Prepared in analogy to example 1 (b) from 5-methanesulfonyl-2-(2,2,3,3,3-pentafluoro-propoxy)-benzoic acid (Example A30) and 1-(5-trifluoromethyl-[1,3,4]thiadiazol-2-yl)-piperazine trifluoroacetate (Example 62(b)). The crude material was purified by chromatography (SiO$_2$, methanol/dichloromethane) to yield the title compound as an off-white solid (yield 56%). MS (m/e): 569.3 (M+H$^+$, 100%).

EXAMPLE 103

[5-Methanesulfonyl-2-(2,2,3,3,3-pentafluoro-propoxy)-phenyl]-[4-(5-trifluoromethyl-thiazol-2-yl)-piperazin-1-yl]-methanone

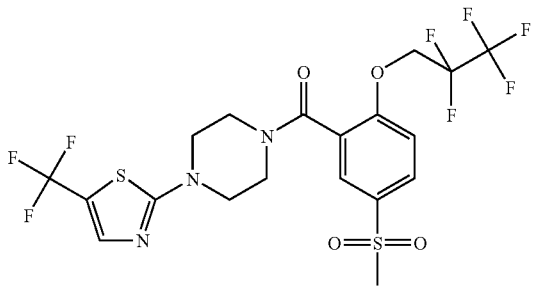

Prepared in analogy to example 1 (b) from 5-methanesulfonyl-2-(2,2,3,3,3-pentafluoro-propoxy)-benzoic acid (Example A30) and 1-(5-trifluoromethyl-thiazol-2-yl)-piperazine hydrochloride (Example 58(c)). The crude material was purified by chromatography (SiO$_2$, ethyl acetate/heptane) to yield the title compound as a brown solid (yield 68%). MS (m/e): 568.2 (M+H$^+$, 100%).

The invention claimed is:
1. A compound of formula I

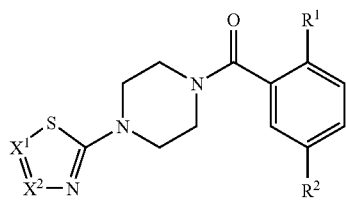

wherein
$R^1$ is —OR$^{1'}$, —SR$^{1'}$, or morpholino;
$R^{1'}$ is lower alkyl, lower alkyl substituted by halogen, or —(CH$_2$)$_n$-cycloalkyl;
$R^2$ is —S(O)$_2$-lower alkyl, —S(O)$_2$NH-lower alkyl, NO$_2$, or CN;
$X^1$ is CR$^3$ or N;
$X^2$ is CR$^{3'}$ or N;
$R^3$ and $R^{3'}$ are each independently hydrogen, halogen, lower alkyl, CN, NO$_2$, —S(O)$_2$-phenyl, —S(O)$_2$-lower alkyl, —S(O)$_2$-pyridin-2, 3 or 4-yl, phenyl optionally substituted by one or two substituents selected from the group consisting of NO$_2$ and halogen, lower alkyl substituted by halogen, or —C(O)-lower alkyl;
n is 0, 1, or 2;
or a pharmaceutically acceptable acid addition salt thereof.

2. A compound of claim 1

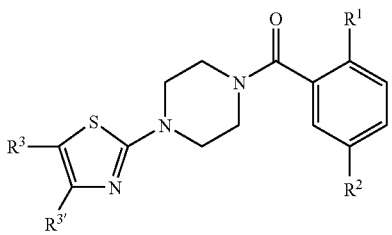

wherein
$R^1$ is —OR$^{1'}$, —SR$^{1'}$, or morpholino;
$R^{1'}$ is lower alkyl, lower alkyl substituted by halogen, or —(CH$_2$)$_n$-cycloalkyl;
$R^2$ is —S(O)$_2$-lower alkyl, —S(O)$_2$NH-lower alkyl, NO$_2$, or CN;
$R^3$ and $R^{3'}$ are each independently hydrogen, halogen, lower alkyl, CN, NO$_2$, —S(O)$_2$-phenyl, —S(O)$_2$-lower alkyl, —S(O)$_2$-pyridin-2, 3 or 4-yl, phenyl optionally substituted by one or two substituents selected from the group consisting of NO$_2$ and halogen, lower alkyl substituted by halogen, or —C(O)-lower alkyl;
n is 0, 1, or 2;
or a pharmaceutically acceptable acid addition salt thereof.

3. A compound of claim 2, wherein $R^1$ is OR$^{1'}$.
4. A compound of claim 3, wherein $R^{1'}$ is lower alkyl.
5. A compound of claim 4, selected from the group consisting of
[4-(5-benzenesulfonyl-thiazol-2-yl)-piperazin-1-yl]-(2-isopropoxy-5-methanesulfonyl-phenyl)-methanone,
2-[4-(2-isobutoxy-5-methanesulfonyl-benzoyl)-piperazin-1-yl]-thiazole-5-carbonitrile,
2-{4-[2-(2,2-dimethyl-propoxy)-5-methanesulfonyl-benzoyl]-piperazin-1-yl}-thiazole-5-carbonitrile,
[4-(5-benzenesulfonyl-thiazol-2-yl)-piperazin-1-yl]-[2-(2,2-dimethyl-propoxy)-5-methanesulfonyl-phenyl]-methanone,
[4-(5-benzenesulfonyl-thiazol-2-yl)-piperazin-1-yl]-(2-isobutoxy-5-methanesulfonyl-phenyl)-methanone,
{4-[5-(butane-1-sulfonyl)-thiazol-2-yl]-piperazin-1-yl}-[2-(2,2-dimethyl-propoxy)-5-methanesulfonyl-phenyl]-methanone,
(2-((R)-sec-butoxy)-5-methanesulfonyl-phenyl)-[4-(5-trifluoromethyl-thiazol-2-yl)-piperazin-1-yl]-methanone,
(2-((S)-sec-butoxy)-5-methanesulfonyl-phenyl)-[4-(5-trifluoromethyl-thiazol-2-yl)-piperazin-1-yl]-methanone and
(2-isopropoxy-5-methanesulfonyl-phenyl)-[4-(4-methyl-5-trifluoromethyl-thiazol-2-yl)-piperazin-1-yl]-methanone.

6. A compound of claim 3, wherein $R^{1'}$ is lower alkyl substituted by halogen.

7. A compound of claim 6, selected from the group consisting of
2-{4-[5-methanesulfonyl-2-(2,2,2-trifluoro-1-methyl-ethoxy)-benzoyl]-piperazin-1-yl}-thiazole-5-carbonitrile,
{4-[5-(butane-1-sulfonyl)-thiazol-2-yl]-piperazin-1-yl}-[5-methanesulfonyl-2-(2,2,2-trifluoro-1-methyl-ethoxy)-phenyl]-methanone,
[5-methanesulfonyl-2-(2,2,2-trifluoro-1-methyl-ethoxy)-phenyl]-[4-(5-methyl-4-trifluoromethyl-thiazol-2-yl)-piperazin-1-yl]-methanone,
[5-methanesulfonyl-2-(2,2,2-trifluoro-1-methyl-ethoxy)-phenyl]-[4-(5-trifluoromethyl-thiazol-2-yl)-piperazin-1-yl]-methanone,
[5-methanesulfonyl-2-(2,2,2-trifluoro-1,1-dimethyl-ethoxy)-phenyl]-[4-(5-trifluoromethyl-thiazol-2-yl)-piperazin-1-yl]-methanone,
[5-methanesulfonyl-2-((S)-2,2,2-trifluoro-1-methyl-ethoxy)-phenyl]-[4-(5-trifluoromethyl-thiazol-2-yl)-piperazin-1-yl]-methanone, and
[5-methanesulfonyl-2-((R)-2,2,2-trifluoro-1-methyl-ethoxy)-phenyl]-[4-(5-trifluoromethyl-thiazol-2-yl)-piperazin-1-yl]-methanone.

8. A compound of claim 6, selected from the group consisting of
[5-methanesulfonyl-2-(2,2,2-trifluoro-1-methyl-ethoxy)-phenyl]-{4-[5-(2,2,2-trifluoro-ethyl)-thiazol-2-yl]-piperazin-1-yl}-methanone,
[5-methanesulfonyl-2-((S)-2,2,2-trifluoro-1-methyl-ethoxy)-phenyl]-{4-[5-(2,2,2-trifluoro-ethyl)-thiazol-2-yl]-piperazin-1-yl}-methanone,
[5-methanesulfonyl-2-((R)-2,2,2-trifluoro-1-methyl-ethoxy)-phenyl]-{4-[5-(2,2,2-trifluoro-ethyl)-thiazol-2-yl]-piperazin-1-yl}-methanone,
[5-ethanesulfonyl-2-(2,2,2-trifluoro-1-methyl-ethoxy)-phenyl]-[4-(5-trifluoromethyl-thiazol-2-yl)-piperazin-1-yl]-methanone,
[5-methanesulfonyl-2-((S)-2,2,2-trifluoro-1-methyl-ethoxy)-phenyl]-[4-(4-methyl-5-trifluoromethyl-thiazol-2-yl)-piperazin-1-yl]-methanone,
[5-methanesulfonyl-2-((R)-2,2,2-trifluoro-1-methyl-ethoxy)-phenyl]-[4-(4-methyl-5-trifluoromethyl-thiazol-2-yl)-piperazin-1-yl]-methanone and
[5-methanesulfonyl-2-(2,2,3,3,3-pentafluoro-propoxy)-phenyl]-[4-(5-trifluoromethyl-thiazol-2-yl)-piperazin-1-yl]-methanone.

9. A compound of claim 3, wherein $R^{1'}$ is $-(CH_2)_n$-cycloalkyl.

10. A compound of claim 1, selected from the group consisting of
2-[4-(2-cyclobutylmethoxy-5-methanesulfonyl-benzoyl)-piperazin-1-yl]-thiazole-5-carbonitrile,
[4-(5-benzenesulfonyl-thiazol-2-yl)-piperazin-1-yl]-(2-cyclopentyloxy-5-methanesulfonyl-phenyl)-methanone,
{4-[5-(butane-1-sulfonyl)-thiazol-2-yl]-piperazin-1-yl}-(2-cyclopentyloxy-5-methanesulfonyl-phenyl)-methanone,
3-[4-(5-cyano-thiazol-2-yl)-piperazine-1-carbonyl]-4-cyclopentyloxy-N-methyl-benzenesulfonamide or
4-cyclopentyloxy-N-methyl-3-[4-(5-trifluoromethyl-[1,3,4]thiadiazol-2-yl)-piperazine-1-carbonyl]-benzenesulfonamide.

11. A compound of claim 2, wherein $R^1$ is $SR^{1'}$.

12. A compound of claim 11, which is
(2-isopropylsulfanyl-5-methanesulfonyl-phenyl)-[4-(5-trifluoromethyl-thiazol-2-yl)-piperazin-1-yl]-methanone.

13. A compound of claim 1

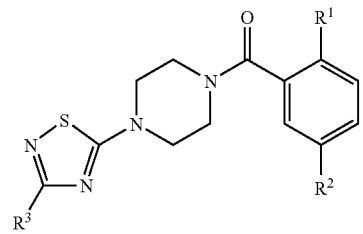

IB wherein
$R^1$ is $-OR^{1'}$, $-SR^{1'}$, or morpholio;
$R^{1'}$ is lower alkyl, lower alkyl substituted by halogen, or $-(CH_2)_n$-cycloalkyl;
$R^2$ is $-S(O)_2$-lower alkyl, $-S(O)_2NH$-lower alkyl, $NO_2$, or CN;
$R^3$ is hydrogen, halogen, lower alkyl, CN, $NO_2$, $-S(O)_2$-phenyl, $-S(O)_2$-lower alkyl, $-S(O)_2$-pyridin-2, 3 or 4-yl, phenyl optionally substituted by one or two substituents selected from the group consisting of $NO_2$ and halogen, lower alkyl substituted by halogen, or $-C(O)$-lower alkyl;
n is 0, 1, or 2;
or a pharmaceutically acceptable acid addition salt thereof.

14. A compound of claim 13, wherein $R^1$ is $OR^{1'}$.

15. A compound of claim 14, wherein $R^{1'}$ is lower alkyl.

16. A compound of claim 15, which is
(2-isopropoxy-5-methanesulfonyl-phenyl)-[4-(3-phenyl-[1,2,4]thiadiazol-5-yl)-piperazin-1-yl]-methanone.

17. A compound of claim 14, wherein $R^{1'}$ is $-(CH_2)_n$-cycloalkyl.

18. A compound of claim 17, which is
4-cyclopentyloxy-N-methyl-3-[4-(3-phenyl-[1,2,4]thiadiazol-5-yl)-piperazine-1-carbonyl]-benzenesulfonamide.

19. A compound of claim 1

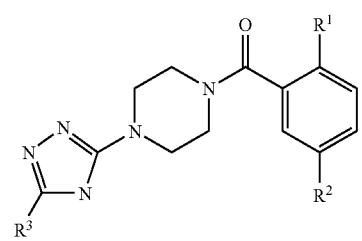

IC wherein
$R^1$ is $-OR^{1'}$, $-SR^{1'}$, or morpholino;
$R^{1'}$ is lower alkyl, lower alkyl substituted by halogen, or $-(CH_2)_n$-cycloalkyl;
$R^2$ is $-S(O)_2$-lower alkyl, $-S(O)_2NH$-lower alkyl, $NO_2$, or CN;
$R^3$ is hydrogen, halogen, lower alkyl, CN, $NO_2$, $-S(O)_2$-phenyl, $-S(O)_2$-lower alkyl, $-S(O)_2$-pyridin-2, 3 or 4-yl, phenyl optionally substituted by one or two substituents selected from the group consisting of $NO_2$ and halogen, lower alkyl substituted by halogen, or $-C(O)$-lower alkyl;

n is 0, 1, or 2;

or a pharmaceutically acceptable acid addition salt thereof.

20. A compound of claim 19, wherein $R^1$ is $OR^{1'}$.

21. A compound of claim 20, selected from the group consisting of (2-isopropoxy-5-methanesulfonyl-phenyl)-[4-(5-trifluoromethyl-[1,3,4]thiadiazol-2-yl)-piperazin-1-yl]-methanone, (2-cyclopropylmethoxy-5-methanesulfonyl-phenyl)-[4-(5-trifluoromethyl-[1,3,4]thiadiazol-2-yl)-piperazin-1-yl]-methanone, (2-isobutoxy-5-methanesulfonyl-phenyl)-[4-(5-trifluoromethyl-[1,3,4]thiadiazol-2-yl)-piperazin-1-yl]-methanone, (5-methanesulfonyl-2-morpholin-4-yl-phenyl)-[4-(5-trifluoromethyl-[1,3,4]thiadiazol-2-yl)-piperazin-1-yl]-methanone and

[5-methanesulfonyl-2-((S)-2,2,2-trifluoro-1-methyl-ethoxy)-phenyl]-[4-(5-trifluoromethyl-[1,3,4]thiadiazol-2-yl)-piperazin-1-yl]-methanone.

22. A pharmaceutical composition comprising a therapeutically effective amount of a compound of formula I

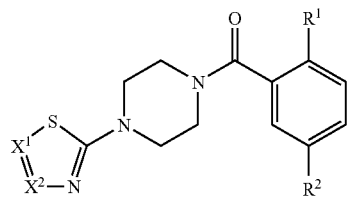

wherein
$R^1$ is $-OR^{1'}$, $-SR^{1'}$, or morpholino;
$R^{1'}$ is lower alkyl, lower alkyl substituted by halogen, or $-(CH_2)_n$-cycloalkyl;
$R^2$ is $-S(O)_2$-lower alkyl, $-S(O)_2NH$-lower alkyl, $NO_2$, or CN;
$X^1$ is $CR^3$ or N;
$X^2$ is $CR^{3'}$ or N;
$R^3$ and $R^{3'}$ are each independently hydrogen, halogen, lower alkyl, CN, $NO_2$, $-S(O)_2$-phenyl, $-S(O)_2$-lower alkyl, $-S(O)_2$-pyridin-2, 3 or 4-yl, phenyl optionally substituted by one or two substituents selected from the group consisting of $NO_2$ and halogen, lower alkyl substituted by halogen, or $-C(O)$-lower alkyl;
n is 0, 1, or 2;
or a pharmaceutically acceptable acid addition salt thereof and a pharmaceutically acceptable carrier.

* * * * *

UNITED STATES PATENT AND TRADEMARK OFFICE
CERTIFICATE OF CORRECTION

PATENT NO.        : 7,220,744 B2  
APPLICATION NO. : 11/324990  
DATED             : May 22, 2007  
INVENTOR(S)       : Jolidon et al.

It is certified that error appears in the above-identified patent and that said Letters Patent is hereby corrected as shown below:

TITLE PAGE:

Item 73
The Assignee information reads "Hoffman-La Roche Inc., Nutley, NJ (US)". The Assignee information should read --Hoffmann-La Roche Inc., Nutley, NJ (US)--.

Item 30
The Foreign Application Priority Data reads "Jan. 7, 2005 (EP).........051100077". The Foreign Application Priority Data should read --Jan. 7, 2005 (EP)........05100077--.

Signed and Sealed this

Seventh Day of August, 2007

JON W. DUDAS
*Director of the United States Patent and Trademark Office*